(12) United States Patent
Thomson et al.

(10) Patent No.: US 11,278,201 B2
(45) Date of Patent: Mar. 22, 2022

(54) APPARATUS FOR COUPLING TO COMPUTING DEVICES AND MEASURING PHYSIOLOGICAL DATA

(71) Applicant: AliveCor, Inc.

(72) Inventors: Euan Thomson, Los Gatos, CA (US); David E. Albert, San Francisco, CA (US); Bruce Richard Satchwell, San Francisco, CA (US); Nupur Srivastava, San Francisco, CA (US); Iman Abuzeid, San Francisco, CA (US)

(73) Assignee: AliveCor, Inc., Mountain View, CA (US)

( * ) Notice: Subject to any disclaimer, the term of this patent is extended or adjusted under 35 U.S.C. 154(b) by 19 days.

(21) Appl. No.: 16/003,448

(22) Filed: Jun. 8, 2018

(65) Prior Publication Data

US 2019/0117068 A1 Apr. 25, 2019

Related U.S. Application Data

(63) Continuation of application No. 14/328,962, filed on Jul. 11, 2014, now abandoned.

(60) Provisional application No. 61/982,002, filed on Apr. 21, 2014, provisional application No. 61/872,555, filed on Aug. 30, 2013, provisional application No. 61/845,254, filed on Jul. 11, 2013.

(51) Int. Cl.
*A61B 5/00* (2006.01)
*A61B 5/332* (2021.01)

(52) U.S. Cl.
CPC ............ *A61B 5/0006* (2013.01); *A61B 5/332* (2021.01); *A61B 5/6898* (2013.01); *A61B 5/681* (2013.01); *A61B 2560/0443* (2013.01)

(58) Field of Classification Search
CPC ... A61B 5/0006; A61B 5/0404; A61B 5/6898; A61B 2560/0443; A61B 5/681; A61B 5/332
See application file for complete search history.

(56) References Cited

U.S. PATENT DOCUMENTS

| | | | | |
|---|---|---|---|---|
| 4,850,370 A | * | 7/1989 | Dower | A61B 5/04011 |
| | | | | 600/512 |
| 5,511,553 A | * | 4/1996 | Segalowitz | A61B 5/282 |
| | | | | 600/508 |

(Continued)

*Primary Examiner* — Catherine M Voorhees
(74) *Attorney, Agent, or Firm* — Womble Bond Dickinson (US) LLP

(57) ABSTRACT

Devices, systems, and methods for measuring and monitoring biometric or physiological parameters in a user-friendly and convenient manner are disclosed. Relevant physiological parameters of the user may be measured as the user normally operates a computing device or other hand-operated or hand-held device. These parameters are measured using an accessory of the device such as a laptop case, a tablet computer case, a smartphone case, or a smart watch or smart armband. The accessory may include at least two or three electrodes for taking an electrocardiogram or other physiological parameters. The measured parameters are transmitted to the computing device. The computing device can be normally used while a physiological parameter monitoring and measurement application loaded onto the computing device operates in the background to receive the measured parameters.

25 Claims, 33 Drawing Sheets

(56) References Cited

U.S. PATENT DOCUMENTS

| | | | | |
|---|---|---|---|---|
| 6,950,695 B2* | 9/2005 | Chen | ............ | A61B 5/02438 600/509 |
| 2009/0043217 A1* | 2/2009 | Hui | ............ | A61B 5/02438 600/509 |
| 2010/0076331 A1* | 3/2010 | Chan | ............ | A61B 5/681 600/522 |
| 2011/0105928 A1* | 5/2011 | Bojovic | ............ | A61B 5/0006 600/515 |
| 2011/0257546 A1* | 10/2011 | Gozzini | ............ | A61B 5/0404 600/509 |
| 2011/0301435 A1* | 12/2011 | Albert | ............ | A61B 5/0404 600/301 |
| 2012/0156933 A1* | 6/2012 | Kreger | ............ | A61B 5/0245 439/625 |
| 2012/0203124 A1* | 8/2012 | Lim | ............ | A61B 5/0404 600/523 |
| 2015/0289820 A1* | 10/2015 | Miller | ............ | A61B 5/1495 600/300 |

* cited by examiner

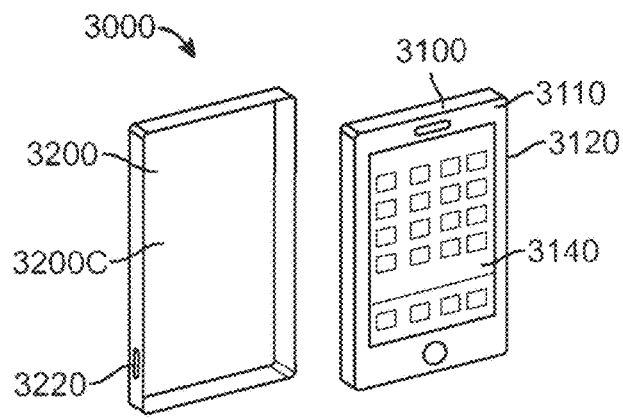
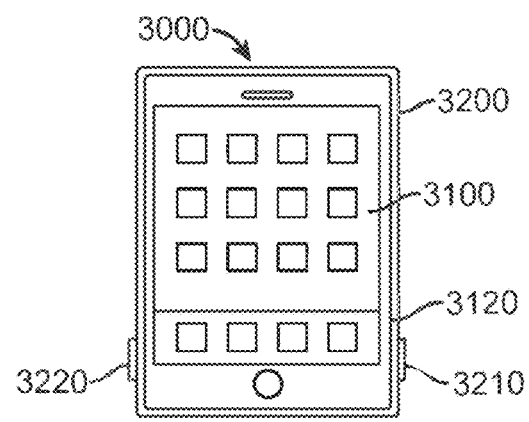
FIG. 3A
FIG. 3B
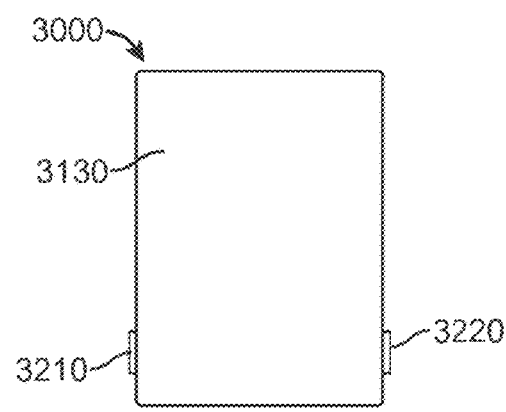
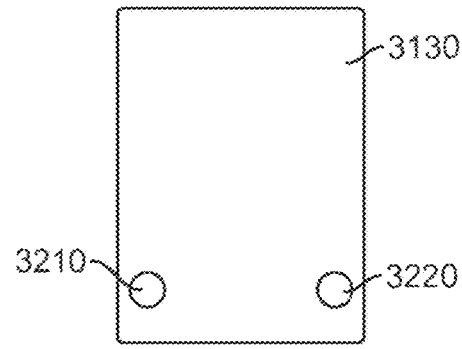
FIG. 3C
FIG. 3D
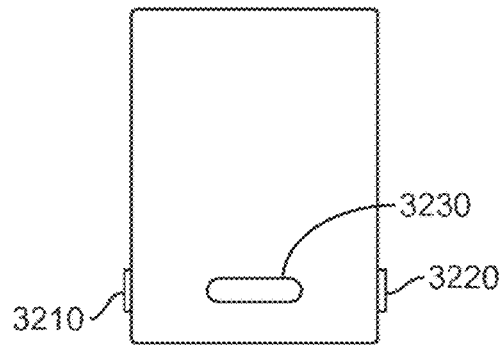
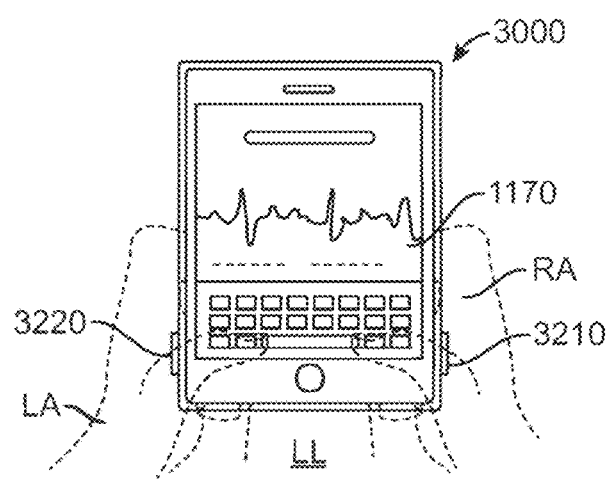
FIG. 3E
FIG. 3F

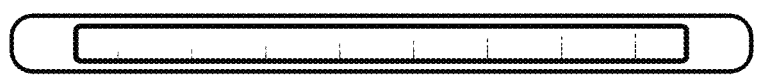
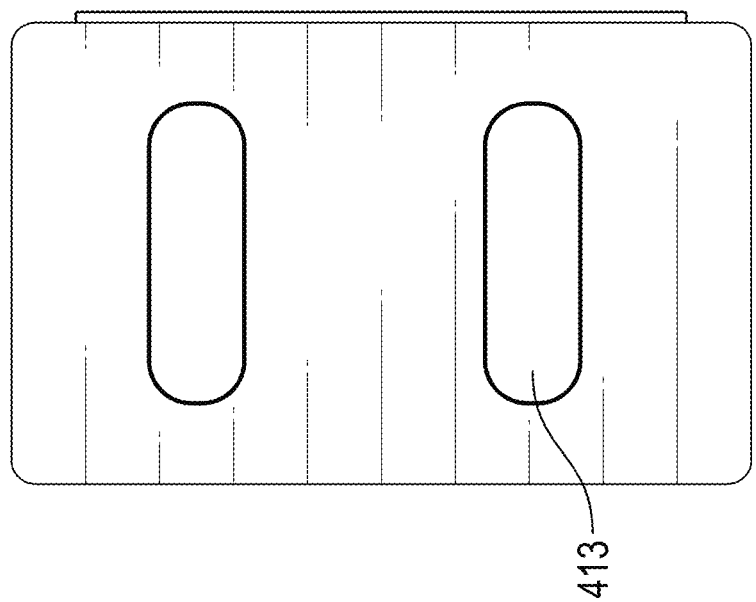
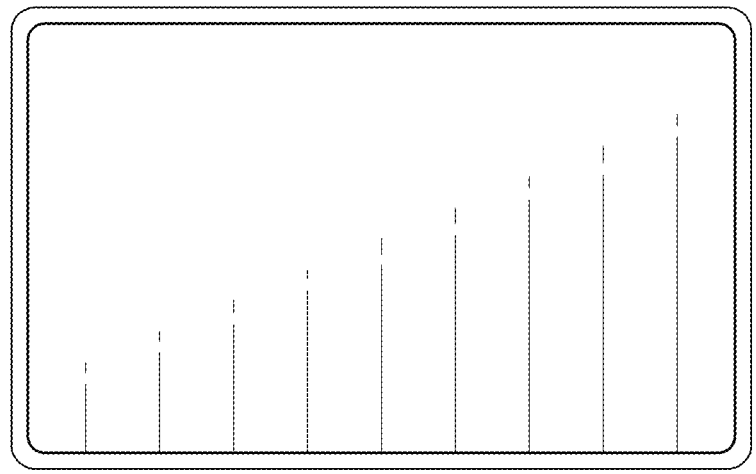

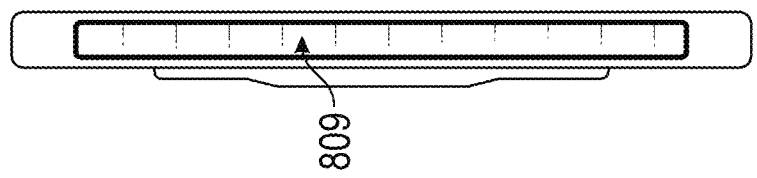
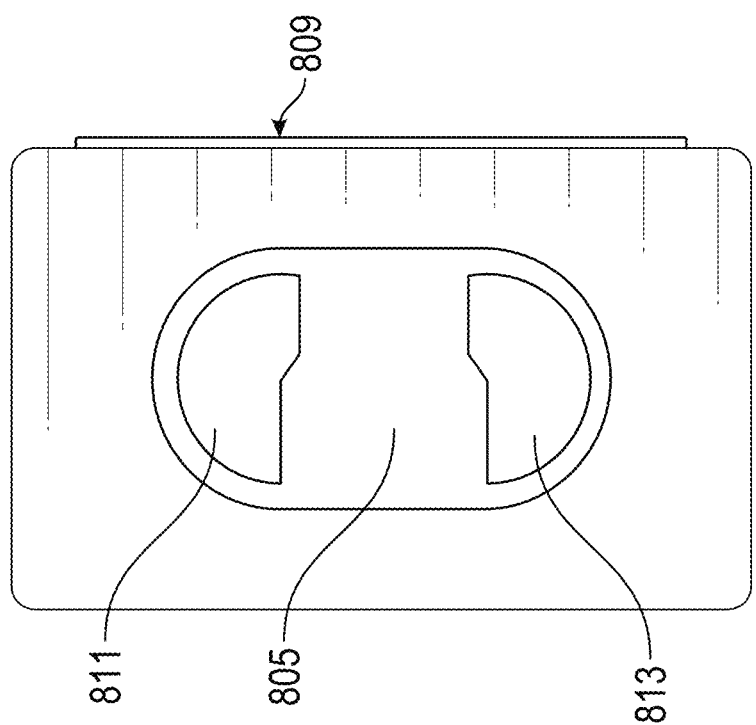
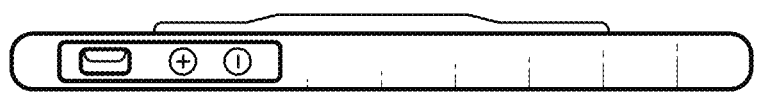

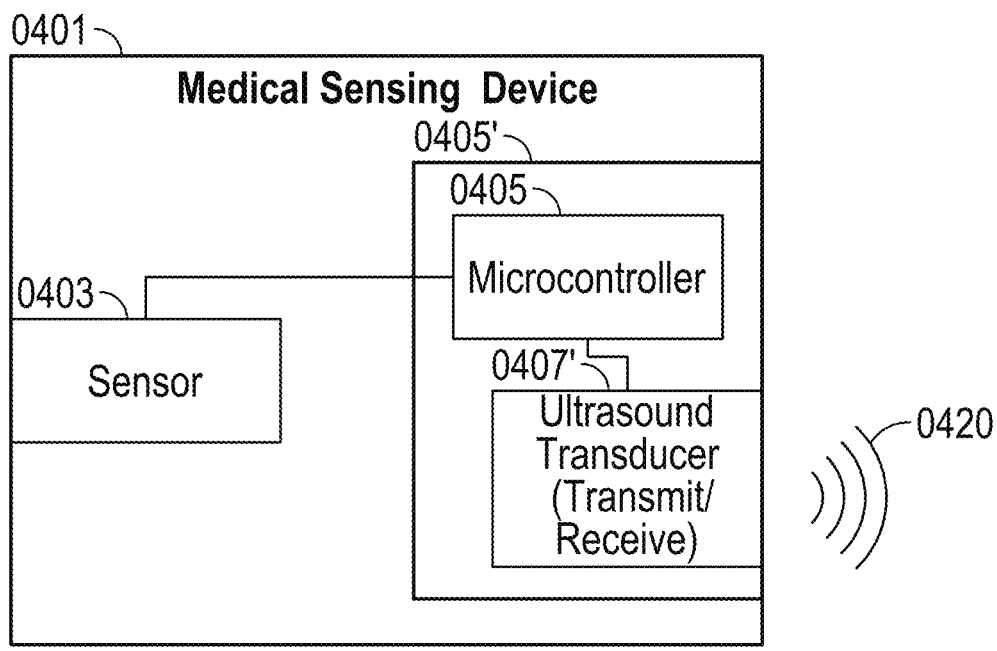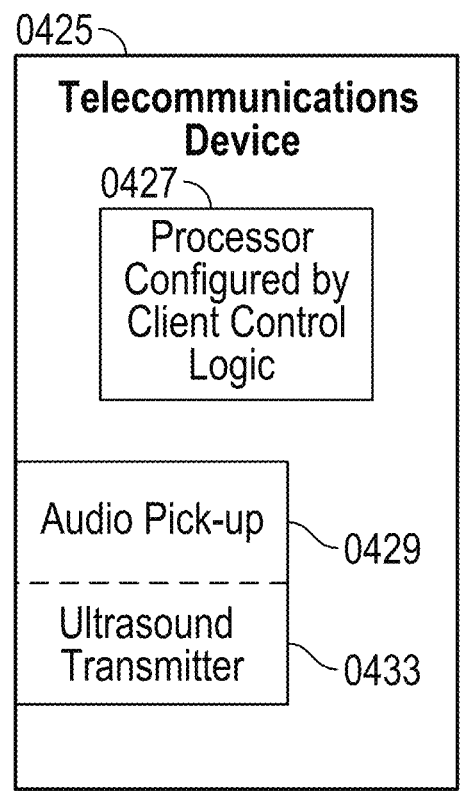
FIG. 21C

APPARATUS FOR COUPLING TO COMPUTING DEVICES AND MEASURING PHYSIOLOGICAL DATA

CROSS-REFERENCE

The present application is a continuation of U.S. application Ser. No. 14/328,962, filed Jul. 11, 2014, which claims the benefit of U.S. Provisional Applications Nos. 61/845,254, filed Jul. 11, 2013 and entitled "Three-Electrode Wireless ECG Apparatus," 61/872,555, filed Aug. 30, 2013 and entitled "Ultrasonic Transmission of Signals from an ECG Sensing Wristlet," and 61/982,002, filed Apr. 21, 2014 and entitled "Methods and Systems for Cardiac Monitoring with Mobile Devices and Accessories," the full contents of which are incorporated herein by reference.

BACKGROUND

The present disclosure relates to consumer and medical devices, systems, and methods. In particular, the present disclosure relates to personal physiology monitoring devices and related systems and methods and more particular to such devices, systems, and methods for providing ECG, heart rate, and cardiac arrhythmia monitoring utilizing a computing device such as a personal computer, a laptop computer, a tablet computer, a smartphone, a wearable computing device or the like.

Cardiovascular diseases are the leading cause of death in the world. In 2008, 30% of all global death can be attributed to cardiovascular diseases. It is also estimated that by 2030, over 23 million people will die from cardiovascular diseases annually. Cardiovascular diseases are prevalent in the populations of high-income and low-income countries alike.

Arrhythmia is a cardiac condition in which the electrical activity of the heart is irregular or is faster (tachycardia) or slower (bardycardia) than normal. Although many arrhythmias are not life-threatening, some can cause cardiac arrest and even sudden cardiac death. Indeed, cardiac arrhythmias are one of the most common causes of death when travelling to a hospital.

Atrial fibrillation (A-fib) is the most common cardiac arrhythmia. In A-fib, electrical conduction through the ventricles of heart is irregular and disorganized. While A-fib may cause no symptoms, it is often associated with palpitations, shortness of breath, fainting, chest, pain or congestive heart failure and also increases the risk of stroke. A-fib is usually diagnosed by taking an electrocardiogram (ECG) of a subject. To treat A-fib, a patient may take medications to slow heart rate or modify the rhythm of the heart. Patients may also take anticoagulants to prevent stroke or may even undergo surgical intervention including cardiac ablation to treat A-fib.

Often, a patient with arrhythmia or A-fib is monitored for extended periods of time to manage the disease. For example, a patient may be provided with a Holter monitor or other ambulatory electrocardiography device to continuously monitor for at least 24 hours the electrical activity of the cardiovascular system.

Electrocardiography is used to study the electrical activity of the heart, and may be used for both diagnosis and treatment. Electrocardiograms (ECG) can be recorded or taken using electrodes placed on the skin of the patient in multiple locations. The electrical signals recorded between electrode pairs are referred to as leads. Varying numbers of leads can be used to take the ECG, and different combinations of electrodes can be used to form the various leads. Examples of leads used for taking ECGs are 3, 5, and 12 leads. For a 12-lead ECG 10 electrodes are used with six on the chest and one on each of the patient's arms and legs.

There are different "standard" configurations for electrode placement that can be used to place the electrodes on the patient. For example, the arm and leg electrodes can be placed closer to the chest or closer to the extremity of the arm/leg. The varying placement of the electrodes on the arms and legs can affect the ECG and make it more difficult to compare to a standard ECG.

The standard or conventional 12-lead ECG configuration uses 10 electrodes. FIG. 7 illustrates a pictorial representation of the 10 electrodes, with 6 electrodes on the patient's chest and one electrode on each of the patient's arms and legs. The electrode placed on the right arm can be referred to as RA. The electrode placed on the left arm can be referred to as LA. The RA and LA electrodes are placed at the same location on the left and right arms, preferably near the wrist. The leg electrodes can be referred to as RL for the right leg and LL for the left leg. The RL and LL electrodes are placed on the same location for the left and right legs, preferably near the ankle.

FIGS. 7 and 8 illustrates the placement of the six electrodes on the chest, labeled V1, V2, V3, V4, V5, and V6. V1 is placed in the fourth intercostal space, for example between ribs 4 and 5, just to the right of the sternum. V2 is placed in the fourth intercostal space, for example between ribs 4 and 5, just to the left of the sternum. V3 is placed between electrodes V2 and V4. V4 is placed in the fifth intercostal space between ribs 5 and 6 in the mid-clavicular line. V5 is placed horizontally even with V4 in the left anterior axillary line. V6 is placed horizontally even with V4 and V5 in the mid-axillary line.

Lead I is typically the voltage between the left arm (LA) and right arm (RA), e.g. I=LA−RA. Lead II is typically the voltage between the left leg (LL) and right arm (RA), e.g. II=LL−RA. Lead III is the typically voltage between the left leg (LL) and left arm (LA), e.g. III=LL−LA. Wilson's central terminal (WCT or VW) can be calculated by (RA+LA+LL)/3.

Augmented limb leads can also be determined from RA, RL, LL, and LA. The augmented vector right (aVR) is equal to RA−(LA+LL)/2 or −(I+II)/2. The augmented vector left (aVL) is equal to LA−(RA+LL)/2 or I−II/2. The augmented vector foot (aVF) is equal to LL−(RA+LA)/2 or II−I/2.

I, II, III, aVR, aVL, and aVF can all be represented on a hexaxial system. Incorrect or shifted electrode placement can shift the results of the ECG on the hexaxial system.

Current ambulatory electrocardiography devices such as Holter monitors, however, are typically bulky and difficult for subjects to administer without the aid of a medical professional. For example, the use of Holter monitors requires a patient to wear a bulky device on their chest and precisely place a plurality of electrode leads on precise locations on their chest. These requirements can impede the activities of the subject, including their natural movement, bathing, and showering. Once a full disclosure ECG is generated, the ECG is sent to the patient's physician who then analyzes the ECG and then provides a diagnosis and other recommendations. Currently, this process often must be performed through hospital administrators and health management organizations and many patients do not receive feedback in an expedient manner.

A number of handheld ECG measurement devices are known, including devices that may adapt existing mobile telecommunications device (e.g., smartphones) so that they can be used to record ECS. However, such devices either require the use of external (e.g., plug-in) electrodes, or include electrodes in a housing that are difficult to properly hold and apply to the body.

Wearable monitors for detecting one or more biometric parameter (including subject motion, heart rate, temperature, ECG, etc.) typically must communicate wirelessly to a monitoring, analysis or recording station ("monitoring station"). Typically, the transmission of information has been performed by short wavelength radio transmission (e.g., "Bluetooth"). Unfortunately, this transmission technique has a substantial power requirement, limiting the battery life, or requiring large, bulky devices that are not readily wearable. Thus, in situations in which the device is desired to be lightweight so that it can be comfortably worn during normal daily activity or exercise, many producers have opted for recording data rather than transmitting it, and downloading it periodically by direct connection to a monitoring station. It would be advantageous to provide a monitoring device that may be worn by the subject on the wrist (e.g., wristlet) or other body region that is capable of reliable and low-energy wireless transmission of data.

For example, cardiac monitoring devices such as those described in U.S. Pat. Nos. 4,221,223, 4,295,472 and 4,230,127 describe wristwatch-sized wearable monitors that can detect ECG signals from a patient wearing the device; these signals may be displayed on the device. These signals are not transmitted. Other similar devices are described in U.S. Pat. No. 4,938,228. U.S. Pat. Nos. 5,351,695, 5,333,616, 5,317,269 and 5,289,824 (all to Mils) describes an improvement of this device which includes an integral hearing-aid type speaker for transmitting an ECG signal over telephone lines using sound over a voice channel of a phone, using audible sound (e.g., between 1 kHz and 3 kHz). The ECG signal is typically digitized and frequency modulated (e.g., as a frequency-shift keyed signal). Unfortunately such devices are literally noisy, producing audible signals, require a great deal of power to generate and transmit, and are not capable of two-way communication, particularly with mobile telecommunications devices.

The following patent references may also be relevant: U.S. Pat. Nos. 5,735,285, 6,264,614, 6,685,633, 6,790,178, 8,301,232, 8,509,882, and 8,615,290 and U.S. Pub. No. 2011/0015496.

Ultrasonic transmission shares many similarities with electrical transmission, but there are also substantial differences, including differences previously considered drawbacks. Further, although techniques such as frequency-shift keying for digitizing information are known, it has been difficult and impractical to implement such technique in a time scale that make such techniques practical for using in medical (e.g., ECG) monitoring. In particular, the transmission of ultrasonic data has, to date, been somewhat limited in the informational content. For example, digital encoding of information by ultrasound has been limited in the amount and content of the information transmitted. There is not yet any standard for transmission or encoding of ultrasonic transmission. Further, such ultrasonic signals are not routinely encrypted.

Thus, it would be advantageous to provide systems, devices and methods for encoding or arranging information sent by ultrasonic transmission. In particular, it would be advantageous to encode information in a manner that circumvents the limits of ultrasonic (as opposed to electromagnetic or audible) transmission. In addition, it would be helpful to provide methods, devices and systems for securely transmitting (e.g., encrypting and/or decrypting) ultrasonic transmission. For example, it would be helpful to dynamically pair a device that ultrasonically transmits ECG information (e.g., a wristlet) with one or more receiving device.

Described herein are methods, devices, and systems for using (or adapting for use) one or more widely available telecommunications devices (including mobile telecommunications devices), such as smart phones, tablet computers, portable computers or desktop computers, to receive and send information (including but not limited to digital health information) that has been encoded by an application device into an ultrasonic signal that can be heard by the telecommunications device and then stored, transmitted and/or analyzed by the telecommunications device. In particular, described herein are methods, devices and systems for encoding this information so that it may be interpreted only by a telecommunications device that has been provided a key. The system, devices and methods (including executable logic) may include techniques for readily providing the key using a different modality (e.g., optical) than the ultrasonic transmission.

U.S. patent application Ser. No. 12/796,188, filed Jun. 8, 2010, titled "HEART MONITORING SYSTEM USABLE WITH A SMART PHONE OR COMPUTER," now U.S. Pat. No. 8,509,882 and U.S. patent application Ser. No. 13/108,738, filed May 16, 2011, titled "WIRELESS, ULTRASONIC PERSONAL HEALTH MONITORING SYSTEM," now U.S. Patent Application Publication No. US/2011/0301439-A1, describe ECG monitors that convert ECG data into ultrasound signals that can be received by a telecommunications device such as a smartphone and then stored, analyzed, and/or displayed. The instant application extends and adapts this teaching and may be used with any of the systems, methods and devices described herein.

There are therefore needs for improved cardiac disease and/or rhythm management and monitoring devices, systems, and methods to address one or more of the above challenges.

SUMMARY

Devices, systems, and methods for measuring and monitoring biometric or physiological parameters in a user-friendly and convenient manner are disclosed. In particular, relevant physiological parameters of the user may be measured as the user normally operates a computing device or other hand-operated or hand-held device. For instance, a system of the present disclosure may enable one or more physiological parameters of the user to be measured as the user normally operates a computing device such as a laptop, a tablet computer, or a smartphone. The one or more physiological parameters may be measured using an accessory of the computing device such as a laptop case, a tablet computer case, a smartphone case, or the like. The normal use of the computing device may include web browsing, reading and writing e-mails or text messages, playing games, or otherwise using other common applications such as book or text readers. A physiological parameter monitoring and measurement application of the present disclosure may operate in the background while the computing device is normally used.

Aspects of the present disclosure provide a system for measuring a cardiac parameter of a user. The system may comprise an apparatus configured to couple to a computing device and a first application loaded onto the computing device. The apparatus may comprise a sensor for measuring the cardiac parameter. The first application may be configured for receiving the measured cardiac parameter from the sensor. The sensor may measure the cardiac parameter and the first application may receive the measured cardiac parameter concurrently with a second application being loaded onto the computing device and being manipulated by the user.

The cardiac parameter may comprises one or more of a heart rate, a heart rate variability, a blood pressure, a blood pressure variability, an arrhythmia, a seisomocardiogram (SCG), an SCG parameter, an electrocardiogram (ECG), or an ECG parameter. In many embodiments, the cardiac parameter comprises an electrocardiogram (ECG) or an ECG parameter.

The computing device may comprise one or more of a personal computer, a laptop computer, a tablet computer, a personal digital assistant (PDA), a smartphone, or a wearable computing device. In many embodiments, the computing device comprises a tablet computer or a smartphone. The apparatus may be configured to removably couple to the computing device and may comprise a cover for covering the computing device, such as a tablet computer case or a smartphone case or cover.

The sensor for measuring the cardiac parameter may comprise first and second electrode leads configured to generate a signal comprising the cardiac parameter upon contact with the user. For example, the first electrode lead may be configured to contact a right arm of the user and the second electrode lead may be configured to contact a left arm of the user to generate a Lead I ECG. Alternatively or in combination, the first electrode lead may be configured to contact the right arm of the user and the second electrode lead may be configured to contact a left leg of the user to generate a Lead II ECG. Alternatively or in combination, the first electrode lead may be configured to contact a left arm of the user and the second electrode lead may be configured to contact the left leg of the user to generate a Lead III ECG. The sensor may further comprise a third electrode lead for contact configured to generate a signal comprising the cardiac parameter upon contact with the user. The first, second, and third electrode leads may be used concurrently to generate one or more of a Lead I, a Lead II, or a Lead III ECG for example. The first electrode lead may be configured to contact a right arm of the user, the second electrode lead may be configured to contact a left arm of the user, and the third electrode lead may be configured to contact a left leg of the user.

The first application may be further configured to display the measured cardiac parameter, for example, on a display of the computing device. The cardiac parameter may be displayed in real-time. The first application may be further configured for storing the measured cardiac parameter in a memory of the computing device. The first application may be further configured for sending the measured cardiac parameter to a remote computing device such as a remote server. The remote computing device may store the cardiac or other physiological parameter data and allow access to such data by medical specialists and other professionals for data analysis, interpretation, and/or diagnosis. The analysis and diagnosis may be sent back to the user through remote computing device and the user's computing device or through other channels such as e-mail, text messaging, or other electronic alerts. Alternatively or in combination, one or more of the first application loaded onto the computing device, another application loaded on the remote server, or another application used by the medical specialist or professional may automatically generate such data analysis, interpretation, or/and diagnosis.

Manipulation of the second application may include one or more of typing on a keyboard of the second application, scrolling on the second application, zooming in or out in the second application, otherwise entering data into the second application, or the like. By allowing the user to manipulate the second application loaded on the computing device while the first application measures and monitors the cardiac and other health parameter of the user, embodiments of the present disclosure allow user-friendly, convenient, and less invasive and disruptive measurement and monitoring of cardiac and other health parameters. For example, the user may hold and normally operate the computing device to check e-mail, web browsing, or operate a mobile application while the first application and the computing device cover measures and/or monitors the users ECG or other cardiac and physiological parameters in the background.

Aspects of the present disclosure also provide a method of measuring a cardiac parameter of a user. An apparatus comprising a sensor for the cardiac parameter may be coupled to a computing device. The cardiac parameter of the user may be measured with the sensor. The measured cardiac parameter may be sent, with the apparatus, to a first application loaded on the computing device. The cardiac parameter may be measured and the first application may receive the sent measured cardiac parameter concurrently with the user manipulating a second application loaded onto the computing device.

The cardiac parameter may comprise one or more of a heart rate, a heart rate variability, a blood pressure, a blood pressure variability, an arrhythmia, a seisomocardiogram (SCG), an SCG parameter, an electrocardiogram (ECG), or an ECG parameter. In many embodiments, the cardiac parameter comprises an electrocardiogram (ECG) or an ECG parameter.

The computing device may comprise one or more of a personal computer, a laptop computer, a tablet computer, a personal digital assistant (PDA), a smartphone, or a wearable computing device. In many embodiments, the computing device comprises a tablet computer or a smartphone. The apparatus may be coupled to the computing device by removably attaching the apparatus to the computing device. For example, the apparatus may comprise a cover for covering the computing device such as a tablet computer case or a smartphone or cover. And, the method may comprise at least partially enclosing the computing device, such as a tablet computer or smartphone, with the case or cover.

The cardiac parameter may be measured with the sensor by measuring the cardiac parameter with first and second electrode leads of the sensor. The first and second electrode leads may be configured to generate a signal comprising the cardiac parameter upon contact with the user. For example, the first electrode lead may be configured to contact a right arm of the user and the second electrode lead may be configured to contact a left arm of the user to generate a Lead I ECG. Alternatively or in combination, the first electrode lead may be configured to contact the right arm of the user and the second electrode lead may be configured to contact a left leg of the user to generate a Lead II ECG. Alternatively or in combination, the first electrode lead may be configured to contact a left arm of the user and the second electrode lead may be configured to contact the left leg of the user to generate a Lead III ECG. The cardiac parameter may also be measured with a third electrode lead of the sensor, the third electrode lead being configured to generate a signal comprising the cardiac parameter upon contact with the user. The first, second, and third electrode leads may be used concurrently to generate one or more of a Lead I, a Lead II, or a Lead III ECG for example. The first electrode lead may be configured to contact a right arm of the user, the second electrode lead may be configured to contact a left arm of the user, and the third electrode lead may be configured to contact a left leg of the user.

Furthermore, the received measured cardiac parameter may be displayed on with a display of the computing device. The cardiac parameter may be displayed in real-time. Also, the measured cardiac parameter may be stored in a memory of the computing device. The measured cardiac parameter may also be sent to a remote computing device such as a remote server. The remote computing device may store the cardiac or other physiological parameter data and allow access to such data by medical specialists and other professionals for data analysis, interpretation, and/or diagnosis. The analysis and diagnosis may be sent back to the user through remote computing device and the user's computing device or through other channels such as e-mail, text messaging, or other electronic alerts. Alternatively or in combination, one or more of the first application loaded onto the computing device, another application loaded on the remote server, or another application used by the medical specialist or professional may automatically generate such data analysis, interpretation, or/or diagnosis.

Manipulation of the second application may include one or more of typing on a keyboard of the second application, scrolling on the second application, zooming in or out in the second application, otherwise entering data into the second application, or the like. By allowing the user to manipulate the second application loaded on the computing device while the first application measures and monitors the cardiac and other health parameter(s) of the user, embodiments of the present disclosure allow user-friendly, convenient, and less invasive and disruptive measurement and monitoring of cardiac and other health parameters. For example, the user may hold and normally operate the computing device to check e-mail, web browse, or operate a mobile application while the first application and the computing device cover measures and/or monitors the users ECG or other cardiac and physiological parameters in the background. In some embodiments, the first application may cause the computing device to alert the user if the health parameter sensor is incorrectly positioned such that proper measurements cannot or should not be taken (i.e., a pop-up may show in the second application).

Aspects of the present disclosure also provide a system for measuring a cardiac parameter of a user. The system may comprise a cover configured to removably attached to a portable computing device. The portable computing device may comprise a front face, a back face, and edges therebetween. The cover may comprise a plurality of sensor electrode leads configured for measuring the cardiac parameter and disposed over the edges of the portable computing device when the cover is attached to the portable computing device. In many embodiments, the plurality of sensor electrode leads is disposed only over the edges of the portable computing device. The portable computing device may comprise a laptop computer, a tablet computer, a personal digital assistant (PDA), or a smartphone.

The cardiac parameter may comprise one or more of a heart rate, a heart rate variability, a blood pressure, a blood pressure variability, an arrhythmia, a seisomocardiogram (SCG), an SCG parameter, an electrocardiogram (ECG), or an ECG parameter. In many embodiments, the cardiac parameter comprises an electrocardiogram (ECG) or an ECG parameter.

The plurality of sensor electrode leads may comprise a first sensor electrode lead and a second sensor electrode lead. The first sensor electrode lead and the second sensor electrode lead may be configured to generate a signal comprising the cardiac parameter upon contact with a first limb and a second limb of the user, respectively. For example, the first electrode lead may be configured to contact a right arm of the user and the second electrode lead may be configured to contact a left arm of the user to generate a Lead I ECG. Alternatively or in combination, the first electrode lead may be configured to contact the right arm of the user and the second electrode lead may be configured to contact a left leg of the user to generate a Lead II ECG. Alternatively or in combination, the first electrode lead may be configured to contact a left arm of the user and the second electrode lead may be configured to contact the left leg of the user to generate a Lead III ECG. The plurality of sensor electrode leads may further comprise a third sensor electrode lead configured to generate a signal comprising the cardiac parameter upon contact with a third limb of the user. The cardiac parameter may also be measured with a third electrode lead of the sensor, the third electrode lead being configured to generate a signal comprising the cardiac parameter upon contact with the user. The first, second, and third electrode leads may be used concurrently to generate one or more of a Lead I, a Lead II, or a Lead III ECG for example.

The system may further comprise a first application loaded onto the portable computing device. The first application may be configured for receiving the measured cardiac parameter from the plurality of sensor electrode leads. The first application may receive the measured cardiac parameter concurrently with a second application being loaded onto the portable computing device and being manipulated by the user. Manipulation of the second application may include one or more of typing on a keyboard of the second application, scrolling on the second application, zooming in or out in the second application, otherwise entering data into the second application, or the like. By allowing the user to manipulate the second application loaded on the computing device while the first application measures and monitors the cardiac and other health parameter of the user, embodiments of the present disclosure allow user-friendly, convenient, and less invasive and disruptive measurement and monitoring of cardiac and other health parameters. For example, the user may hold and normally operate the computing device to check e-mail, web browse, or operate a mobile application while the first application and the computing device cover measures and/or monitors the users ECG or other cardiac and physiological parameters in the background.

The first application may be configured to display the received cardiac parameter on a display of the portable computing device. The received cardiac parameter may be displayed in real-time. The first application may be further configured for storing the measured cardiac parameter in a memory of the portable computing device. The first application may be further configured for sending the measured cardiac parameter to a remote computing device such as a remote server. The remote computing device may store the cardiac or other physiological parameter data and allow access to such data by medical specialists and other professionals for data analysis, interpretation, and/or diagnosis. The analysis and diagnosis may be sent back to the user through remote computing device and the user's computing device or through other channels such as e-mail, text messaging, or other electronic alerts. Alternatively or in combination, one or more of the first application loaded onto the computing device, another application loaded on the remote server, or another application used by the medical specialist or professional may automatically generate such data analysis, interpretation, or/and diagnosis.

Aspects of the present disclosure also provide a method for measuring a cardiac parameter of the user. A cover may be removably attached to a portable computing device. The portable computing device may comprise a front face, a back face, and edges therebetween. First and second electrode leads of the cover may be contacted to first and second limbs of the user, respectively, to generate a signal comprising the cardiac parameter. The first and second electrode leads of the cover may be disposed over the edges of the portable computing device. In many embodiments, the plurality of sensor electrode leads may be disposed only over the edges of portable computing device. The portable computing device may comprise a laptop computer, a tablet computer, a personal digital assistant (PDA), or a smartphone.

The cardiac parameter may comprise one or more of a heart rate, a heart rate variability, a blood pressure, a blood pressure variability, an arrhythmia, a seisomocardiogram (SCG), an SCG parameter, an electrocardiogram (ECG), or an ECG parameter. In many embodiments, the cardiac parameter comprises an electrocardiogram (ECG) or an ECG parameter.

A third electrode lead may be contacted to a third limb of the user to generate the signal comprising the cardiac parameter. The first limb may comprise a right arm, the second limb may comprise a left arm, and the third limb may comprise the left leg. These three limbs may be contacted concurrently with the first, second, and third electrode leads respectively to concurrently generate a Lead I ECG, a Lead II ECG, and a Lead III ECG. Alternatively, the first and second electrode leads may be used to generate a Lead I ECG, a Lead II ECG, or a Lead III ECG. For example, the first electrode lead may be configured to contact a right arm of the user and the second electrode lead may be configured to contact a left arm of the user to generate a Lead I ECG. Alternatively or in combination, the first electrode lead may be configured to contact the right arm of the user and the second electrode lead may be configured to contact a left leg of the user to generate a Lead II ECG. Alternatively or in combination, the first electrode lead may be configured to contact a left arm of the user and the second electrode lead may be configured to contact the left leg of the user to generate a Lead III ECG.

A first application may be loaded onto tablet computer or smartphone. The first application may be configured for receiving the measured cardiac parameter from the plurality of sensor electrode leads. The first application may receive the measured cardiac parameter concurrently with a second application being loaded onto the computing device and being manipulated by the user. Manipulation of the second application may include one or more of typing on a keyboard of the second application, scrolling on the second application, zooming in or out in the second application, otherwise entering data into the second application, or the like. By allowing the user to manipulate the second application loaded on the computing device while the first application measures and monitors the cardiac and other health parameter of the user, embodiments of the present disclosure allow user-friendly, convenient, and less invasive and disruptive measurement and monitoring of cardiac and other health parameters. For example, the user may hold and normally operate the computing device to check e-mail, web browse, or operate a mobile application while the first application and the computing device cover measures and/or monitors the users ECG or other cardiac and physiological parameters in the background.

The received cardiac parameter may be displayed, with the first application, on a display of the tablet computer or smartphone. The received cardiac parameter may be displayed in real-time. The measured cardiac parameter may be stored in a memory of the computing device. The measured cardiac parameter may be sent to a remote computing device such as a remote server. The remote computing device may store the cardiac or other physiological parameter data and allow access to such data by medical specialists and other professionals for data analysis, interpretation, and/or diagnosis. The analysis and diagnosis may be sent back to the user through remote computing device and the user's computing device or through other channels such as e-mail, text messaging, or other electronic alerts. Alternatively or in combination, one or more of the first application loaded onto the computing device, another application loaded on the remote server, or another application used by the medical specialist or professional may automatically generate such data analysis, interpretation, or/and diagnosis.

Aspects of the present disclosure also provide a system for measuring a cardiac parameter of a user. The system may comprise a sensor apparatus and an application. The apparatus may be configured for coupling to a keyboard of a computing device, a steering wheel of a motorized vehicle, or a handle bar of a bicycle, a motorcycle, an exercise machine such as a treadmill or an elliptical machine or a weight-lifting machine, a seat, a chair, a set of eyeglasses, clothing, etc. The apparatus may comprise a sensor for measuring the cardiac parameter. The apparatus may be configured to receive the measured cardiac parameter from the sensor as the keyboard of the computing device, the steering wheel of the motorized vehicle, the handle bar of the bicycle, the motorcycle, or the exercise machine is being contacted, held, or manipulated. Further methodologies and systems for conveniently, non-invasively, and non-disruptively measuring and monitoring cardiac and other physiological parameters while a user normally operates a computing or other device in contact with the body of the user are also contemplated.

The present disclosure also describes apparatus, including systems, software, and devices, as well as methods (including method for using these apparatus) to take Electrocardiogram (ECG) information from a subject using an interface that is compatible with a mobile telecommunications device having three electrodes. Described herein are apparatus for detecting ECGs that may address the problems, including but not limited to those identified above, with currently available ECG sensing systems.

In general, the apparatuses (including devices and systems) and methods described herein are for use in detecting biological signals such as electrocardiograms (ECGs). In particular, described herein are apparatuses for use with a mobile telecommunications device so that the mobile telecommunications device may receive biological signals measured directly from a patient. The apparatus typically include three or more electrodes (or exactly three electrodes) for receiving a signal, such as a voltage or current, from the patient's body. The apparatus may also include a housing. The housing may be configured to hold or connect directly to the mobile telecommunications device, such as a "case." The one or more electrodes may be positioned directly on an outer surface of the housing. The apparatus may also include one or more transmitter for communication sensed signals, including modified/processed versions of the sensed signals, from the electrodes to a mobile telecommunications device. The mobile telecommunications device may be connected to the housing, e.g., within a case formed by the housing, or nearby. In some variations, the apparatus may include one or more processors for processing the signals detected on the electrodes.

Any appropriate transmitter may be used, including wireless transmitters. In some variations, the wireless transmitter is an ultrasound transmitter that may use inaudible ultrasound (e.g., >10 kHz, >12 kHz, >15 kHz, >18 kHz, >19 kHz) that can be received by a microphone on the mobile telecommunications device and transmitted and/or further processed by the mobile telecommunications device. Examples of such systems are described in U.S. Pat. No. 8,301,232, and U.S. Patent Applications Publications Nos: US/2011/0301435 and US/2011/0301439, and by PCT Application Publication No. PCT/US2013/023370, each of which is herein incorporated by reference in its entirety.

The apparatuses described herein may be configured so that they can be held by a patient against the patient's leg (e.g., left leg or right leg) using both hands, to measure six of "leads" (leads I-II, and augmented leads aVR, aVL, aVF) from the patient. In some variations, the apparatus may be configured so that the patient can see easily the screen of the mobile telecommunications device while holding the apparatus (enclosing a mobile telecommunications device) with both hands against the leg (right or left) to record isolated signals from each of the right arm, left arm and right or left leg. This will allow the patient to receive immediate visual feedback from the apparatus as the measurement is made, including providing guidance (using the mobile telecommunications device screen or audio output) to adjust or correct the contact or position of the electrodes, and/or to display one or more ECG signals. Thus, the apparatus may be configured as described herein so that it can be easily held to allow electrically distinct readings from each arm (right, left) and leg (left or right), while still allowing the subject holding the device to observe the screen of a mobile telecommunications device coupled to the device.

In general, a patient (as used herein) may be a human or non-human patient, including, but not limited to animals (dogs, cats, horses, etc.). Thus, any of the apparatuses or methods described herein may be used for veterinary use or configured as veterinary products.

In general, a mobile telecommunications device may include any mobile telecommunications device such as, but not limited to, a mobile (e.g., cellular) phone or equivalent, including an iPhone™, Droid™, or the like. A mobile telecommunications device typically may include a processor or other computing module/device which may rim software, hardware of the like, including machine readable code configured to operate the device to receive and/or send information from the apparatus described herein. Such code may be provided with, or separately from, the apparatus described. A mobile telecommunications device may be referred to (and includes) a cell or cellular phone or telephone, a mobile phone or telephone, a smartphone, an handheld computer, tablet, a wearable computer, or the like. Code may be referred to a software, or application software ("app" or "application") and may be downloaded from a remote location onto the mobile telecommunications device.

For example, described herein are electrocardiogram (ECG) detection apparatuses for use with a wireless telecommunications device. In some variations, an apparatus includes: a case configured to fit over the telecommunications device, the case having an outer back surface, at least two outer side surfaces perpendicular to the back surface, and a front region through which a screen of the telecommunications device held in the case may be viewed; a first electrode on or adjacent to one of the at least two outer side surfaces; a second electrode on the outer back surface, the second electrode having an outer contact surface; and a third electrode on the outer back surface, the third electrode having an outer contact surface, wherein the outer contact surfaces of the second and third electrodes are recessed relative to at least a portion of the outer back surface so that the outer contact surfaces of the second and third electrodes do not contact a table surface when the case is placed on the table surface with the outer back surface facing the table surface, and further wherein the second and third electrodes are arranged so that a patient can touch the outer contact surface of the second electrode with just a left hand and the outer contact surface of the third electrode with just a right hand, while holding the first electrode against a leg and can view the screen of the telecommunications device held in the case.

When the apparatus is configured as a case, the case may be configured to hold a mobile telecommunications device within a cavity, or to otherwise be applied over the mobile telecommunications device. The case may therefore include an inner surface or surfaces for holding the mobile telecommunications device, and may have a front region through which the screen and/or any controls of the mobile telecommunications device may be seen and/or manipulated. For example, the case may include a cut-out region or a transparent covering though which the mobile telecommunications device may be seen. The electrodes may be mounted on the case. The case may also include one or more other openings for accessing controls, inputs, outputs, or connection regions (e.g., jacks, plug-in receptacles, etc.) of the mobile telecommunications device. In general, the electrodes are arranged on the case so that (1) they are protected from contacting a surface, particularly a metal surface, when the device is not in used, and (2) they can be easily contacted by a patient holding the apparatus against a leg to simultaneously record from both arms (via the hands) and the leg, while still easily viewing the screen. The case may also house additional components such as a transmitter as mentioned above, a power supply (e.g., battery, solar power supply, etc.) and/or a processor or other circuitry for conditioning, amplifying, filtering, or otherwise modifying the signal(s) received by the electrodes. In some variations, the apparatus may be configured so that one of the electrodes (e.g., the second or third electrode) may act as a reference electrode to the other two (or in some cases more) electrodes.

In variations, where the case may include one or more attachment regions for one or more of the electrodes. For example, the may include an opening on the back for interfacing with an electrode unit that can be used with cases having different configurations (e.g., for fitting different sized mobile telecommunications devices). All three electrodes may be part of the same electrode unit, or multiple electrode units may be used. The electrode unit may include additional hardware such as the processors mentioned, and may also include the power supply or other electronic components.

The second and third electrodes are typically configured so that they can be each by easily contacted by a patient's hands. For example, the second electrode may be positioned and sized so that the patient can touch it with his/her left hand when the patient is also touching the appropriately shaped and sized third electrode with his/her right hand. For example, in some variations the second and third electrodes are entirely on the outer back surface. The second electrode may be on the upper/left half of the back of the case (relative to the mobile telecommunications device) while the third electrode is positioned on the bottom/right half of the back of the case. The second and third electrodes may be separated by a gap sized and/or shaped to prevent overlap between the contact with the left and right hands. In general, the patient should only touch each electrode with a single hand.

The second and third electrode may be formed of any appropriate conductive material (including metal, alloys, etc.) and may be sized so that they can be easily contacted by one or more fingers (or the palm) of a patient holding the device. In some variations, the second and third electrodes are symmetrically positioned relative to each other from the center of the outer back surface.

The first electrode may be configured so that it can be easily held against the patient's leg while holding the case, and touching the second and third electrodes with left and right hands, respectively. Thus, in some variations, the first electrode is entirely positioned on the side of the case (e.g., on one of the at least two outer side surfaces). Alternatively, the first electrode may be on the back surface of the case, but extending along the edge, so that it can be held against the leg when the edge of the case held against the leg. Thus, the first electrode may be on the back surface but abutting or immediately adjacent to the side surface (one of the at least two outer side surfaces). In some variations, the first electrode bends over the edge of the case from the back surface to a side of the case, e.g., along the edge of the case. Thus, the first electrode may extend over an edge between the outer back surface and the one of the outer side surfaces. Any of these configurations may allow the case of the mobile telecommunications device to be held at an angle relative to the patient's leg so that the patient can make good contact with the leg while still holding the case with both hands, contacting the second and third electrodes, and viewing the screen of the mobile telecommunications device.

Thus, in general, the first electrode may extend along all or part (e.g., >half) the length of one side of the case. If the first electrode is on or near the edge of the case, and extends along all or a substantial portion (e.g., between about 100% and about 50%, between about 90% and about 60%, about 75%) of the edge of the case, it may be easy to hold the case against the leg and make contact as described and shown herein. For example, the outer side surfaces of the case may be generally rectangular; the first electrode may be centered between two short edges of one of the outer side surfaces and extend longitudinally in the direction of a long edge of one of the outer side surfaces. As mentioned, the first electrode may extend on or adjacent to the outer side surface for more than half the length of the outer side surface.

In some variations, the apparatus has only three electrodes on an outer surface of the case (e.g., the first, second, and third electrodes).

In general, the apparatus may be configured so that the electrodes do not contact a table surface when the apparatus is set down on the table with the electrodes (first and/or second and third) facing the table. This permits the device to be placed down on a metal surface, as is often found in hospital or other medical settings, without creating a conductive pathway between the electrodes and thereby potentially discharging (and/or draining power from the apparatus). In some variations, the electrodes are recessed relative to the outer back surface. For example, the electrodes may be recessed within a material forming the case. Alternatively or additionally, the case may include one or more projections on which the case may rest when placed back-surface down, preventing one or more electrodes from contacting the surface. For example, the outer back surface of the case may include one or more "spacers" configured to extend a portion of the outer back surface relative to the outer contact surfaces of the first and second surfaces so that the outer contact surfaces are recessed relative to an outer surface of the one or more spacers. In general, a spacer may refer to projection from the back surface having a height greater than the height of the electrode(s), relative to the back surface of the device. For example, a spacer may be a bump, island, bar, piece, tab, etc., extending from the back surface, in some variations around (e.g., all or partially surrounding) the electrodes.

In general, the electrodes may be of sufficient surface area for easily making reliable contact with the patient's hands and/or leg. The first (leg) electrode may be of a different shape or size than the second and third electrodes. In some variations, the surface area of the three electrodes is approximately the same. In some variations the surface area of the second or third (reference) electrode is larger than the other electrodes.

As mentioned, any of the apparatuses described herein may include a transmitter for communicating with a wireless telecommunications device. The transmitter may generally be wireless or it may be directly connected (plugged into) the wireless telecommunications device. Electromagnetic transmitters (including near field transmitters, radio (RF) transmission, etc.), optical transmitters, or any other transmission type may be used. In particular, described herein are ultrasound transmitters that may be integrated into the apparatus.

For example, described herein are electrocardiogram (ECG) detection apparatuses for use with a wireless telecommunications device, the apparatuses comprising: a case configured to fit over the telecommunications device, the case having an outer back surface, at least two outer side surfaces perpendicular to the back surface, and a front region through which a screen of the telecommunications device held in the case may be viewed; a first electrode on or adjacent to one of the at least two outer side surfaces; a second electrode on the outer back surface, the second electrode having an outer contact surface; a third electrode on the outer back surface, the third electrode having an outer contact surface; and an ultrasonic transmitter configured to ultrasonically transmit signals sensed from the first, second and third electrodes to a wireless telecommunications device, wherein the outer contact surfaces of the second and third electrodes are recessed relative to at least a portion of the outer back surface so that the outer contact surfaces of the second and third electrodes do not contact a table surface when the case is placed on the table surface with the outer back surface facing the table surface.

Also described herein are methods of using any of the apparatuses described. For example, described herein are methods of generating an electrocardiogram (ECG) from a patient using a hand-held wireless telecommunications device case having three electrodes on an outer surface of the case, the method comprising: instructing the patient to hold the a first electrode extending along a side of the case against a leg while concurrently touching a second electrode on the back of the case with a right hand and a third electrode on the back of the case with a left hand, so that the patient contacts no more than three electrodes on the case; detecting a first lead signal (lead I) of an ECG between the third electrode and the second electrode; detecting a second lead signal (lead II) of an ECG between the second electrode and the first electrode; and detecting a third lead signal (lead III) of an ECG between the first electrode and the third electrode.

Also described herein are methods of generating an electrocardiogram (ECG) from a patient using a hand-held wireless telecommunications device case having three electrodes on an outer surface of the case, the method comprising: instructing the patient to hold the a first electrode of the case against a leg while concurrently touching a second electrode with a right hand and a third electrode with a left hand, so that the patient contacts no more than three electrodes on the case; detecting a first lead signal (lead I) of an ECG between the third electrode and the second electrode; detecting a second lead signal (lead II) of an ECG between the second electrode and the first electrode; detecting a third lead signal (lead III) of an ECG between the first electrode and the third electrode; and ultrasonically transmitting the lead signals from the case to a telecommunications device.

Aspects of the present disclosure also provide an electrocardiogram (ECG) detection apparatus for use with a wireless telecommunications device. The apparatus may comprise a case configured to fit over the telecommunications device. The case may have an outer back surface, at least two outer side surfaces perpendicular to the back surface, and a front region through which a screen of the telecommunications device held in the case may be viewed. The apparatus may further comprise a first electrode on or adjacent to one of the at least two outer side surfaces, a second electrode on the outer back surface and having an outer contact surface, and a third electrode on the outer back surface and having an outer contact surface. The outer contact surfaces of the second and third electrodes may be recessed relative to at least a portion of the outer back surface so that the outer contact surfaces of the second and third electrodes do not contact a table surface when the case is placed on the table surface with the outer back surface facing the table surface. Further, the second and third electrodes may be arranged so that a patient can touch the outer contact surface of the second electrode with just a left hand and the outer contact surface of the third electrode with just a right hand, while holding the first electrode against a leg and can view the screen of the telecommunications device held in the case.

The second and third electrodes may be entirely on the outer back surface. The first electrode may be entirely positioned on one of the at least two outer side surfaces. The first electrode may be on the outer back surface immediately adjacent to one of the at least two outer side surfaces. The first electrode may extend over an edge between the outer back surface and the one of the outer side surfaces. The outer side surfaces may each be rectangular and the first electrode may be centered between two short edges of one of the outer side surfaces and may extend longitudinally in the direction of a long edge of one of the outer side surfaces. The first electrode may extend on or adjacent to the outer side surface for more than half the length of the outer side surface. The second and third electrodes may be symmetrically positioned relative to each other from the center of the outer back surface. The second and third electrodes may be part of an electrode unit that fits within an opening in the outer back surface of the case. The first electrode may have a surface area approximately the same as the surface area of the second or third electrodes.

The apparatus may comprise only three electrodes on an outer surface of the case. The outer back surface of the case may comprise one or more spacers configured to extend a portion of the outer back surface relative to the outer contact surfaces of the first and second surfaces so that the outer contact surfaces are recessed relative to an outer surface of the one or more spacers.

The apparatus may further comprise an ultrasonic transmitter configured to ultrasonically transmit signals sensed from the first, second and third electrodes to a wireless telecommunications device.

Aspects of the present disclosure also provide an electrocardiogram (ECG) detection apparatus for use with a wireless telecommunications device. The apparatus may comprise a case configured to fit over the telecommunications device. The case may have an outer back surface, at least two outer side surfaces perpendicular to the back surface, and a front region through which a screen of the telecommunications device held in the case may be viewed. The apparatus may further comprise a first electrode on or adjacent to one of the at least two outer side surfaces; a second electrode on the outer back surface and having an outer contact surface, a third electrode on the outer back surface and having an outer contact surface, and an ultrasonic transmitter configured to wirelessly (e.g., ultrasonically) transmit signals sensed from the first, second and third electrodes to a wireless telecommunications device. The outer contact surfaces of the second and third electrodes may be recessed relative to at least a portion of the outer back surface so that the outer contact surfaces of the second and third electrodes do not contact a table surface when the case is placed on the table surface with the outer back surface facing the table surface.

Aspects of the present disclosure also provide a method of generating an electrocardiogram (ECG) from a patient using a hand-held wireless telecommunications device case having three electrodes on an outer surface of the case. The patient may be instructed to hold the first electrode extending along a side of the case against a leg while concurrently touching a second electrode on the back of the case with a right hand and a third electrode on the back of the case with a left hand, so that the patient contacts no more than three electrodes on the case. A first lead signal (lead I) of an ECG may be detected between the third electrode and the second electrode. A second lead signal (lead II) of an ECG may be detected between the second electrode and the first electrode. A third lead signal (lead III) of an ECG may be detected between the first electrode and the third electrode.

Aspects of the present disclosure also provide a method of generating an electrocardiogram (ECG) from a patient using a hand-held wireless telecommunications device case having three electrodes on an outer surface of the case. The patient may be instructed to hold the first electrode of the case against a leg while concurrently touching a second electrode with a right hand and a third electrode with a left hand, so that the patient contacts no more than three electrodes on the case. A first lead signal (lead I) of an ECG may be detected between the third electrode and the second electrode. A second lead signal (lead II) of an ECG may be detected between the second electrode and the first electrode. A third lead signal (lead III) of an ECG may be detected between the first electrode and the third electrode. The lead signals may be wirelessly (e.g., ultrasonically) transmitted from the case to a telecommunications device.

Also described herein are wearable wristlet devices that may reliably and conveniently transfer information (e.g., ECG information) recorded from a user using ultrasound. Also described are monitoring stations, including control logic for configuring and operating a mobile computing/telecommunications device as a monitoring station competent to securely and reliably receive this ultrasound data.

In general, described herein are devices, systems and methods for ultrasonically transmitting digital and/or analog data from (and in some cases to) a wearable (e.g., wristlet) device having one or more sensors, a microprocessor, and a transducer capable of delivering ultrasonic frequencies (i.e., piezo speaker). The digitally transmitted data may be received by a receiving device having a microphone, such as a telecommunications device (e.g., a personal telecommunications device, phone such as an iPhone, DROID, or other smartphone, iPad or other personal computers, PDAs, or the like), where the microphone is competent to receive audio in the ultrasound frequency range (e.g., greater than 17 kHz, greater than 18 kHz, between about 16 kHz to about 22 kHz, between about 17 kHz to about 30 kHz, between about 18 kHz and 32 kHz, between about 17 kHz and 42 kHz, etc.). The digital information transmitted may be encoded and/or encrypted as described in greater detail below. In addition, the information may be compressed (data compressed) before encryption.

Both one-way (e.g., from wristlet to device) and two-way communication are contemplated, including various methods for performing simple two-way communication between the wearable device and the monitoring station (e.g., smartphone).

Also described herein are ultrasonic digital modems and digital modem protocols and logic for securely transmitting digital information ultrasonically from a wearable device such as a wristlet, to a telecommunications device configured as a receiver.

Described herein are wristlet devices that include one or more sensors for sensing activity and/or health information about the wearer that include a microcontroller configured as an ultrasonic modem. In some variations, the microcontrollers include logic (e.g., hardware, software, firmware, or some combination thereof) that permits the device to drive ultrasonic transmission of data from a speaker (e.g., piezoelectric speaker element). Methods of configuring or adapting a microcontroller to operate as an ultrasonic modem are also described. For example, in some variations a microcontroller may be programmed to operate as an ultrasonic modem. The ultrasonic modem may be configured to format the information to be transferred as a hybrid digital and analog format. In some variations, the ultrasonic modem may be an ultrasonic modem component that encrypts the information using an encryption key.

Also described herein are receivers configured to receive ultrasonic digital data acoustically transmitted by an ultrasonic digital modem. In general, a telecommunications device (e.g., smartphone) may be configured to act as a receiver to receive ultrasonic digital data. Thus, a telecommunications device may include hardware, software, and/or firmware configured to receive, decode, interpret, display, analyze, store and/or transmit data sent by ultrasonic transmission from a digital ultrasonic modem. In some variations, logic (e.g., client software and/or firmware, applications, etc.) may be executed on the telecommunications device so that it may act as a receiver for the digital ultrasound data. Thus, described herein is executable logic for receiving and interpreting (e.g., decoding) data transmitted by digital ultrasonic modem, and devices including executable logic for receiving and interpreting (e.g., decoding) data transmitted by digital ultrasonic modem executable logic.

Further described herein are specific devices and system configured to include digital ultrasonic modems. Any of these devices may include a source of the digital information (e.g., device such as a medical sensor or device (e.g., thermometer, pulse oximeter, etc.), a sound transducer (e.g., a speaker capable of emitting ultrasound signals) and a controller (e.g., microcontroller) configured to encode digital information from the source of digital information as an ultrasound signal to be transmitted by the sound transducer. In some variations, the sound transducer is configured to emit both audible (e.g., lower than ultrasound) sounds (to buzz, beep and the like within normal human hearing range) as well as emitting in the ultrasound frequency (e.g., greater than 17 KHz).

In an example, described herein a Texas Instrument's AFE4110 digital thermometer has been modified as described to encode and transmit the temperature data ultrasonically to a telecommunications device (e.g., a smartphone) located some distance from the thermometer. The microcontroller of the device (an MSP430 type controller from Texas Instruments) has been configured to include an ultrasonic modem for transmission of ultrasonic digital data by encoding (via the microprocessor) the data signal for transmission on a connected piezoelectric speaker. The speaker may be the same speaker that is preset in the thermometer and used for audibly (e.g., with the normal audible range for humans) notifying the user that the temperature is stable. Thus, the thermometer may be retrofitted to include the digital ultrasound modem at very low cost by executing control logic in the microcontroller to process data from the thermometer and transmit the encoded signal on the piezoelectric speaker in the ultrasonic frequency range (e.g., >17 KHz). The thermometer may include a security key (e.g., bar code, QR code, etc.) printed on the outside of the device that may be read by the receiving telecommunications device (e.g., smartphone).

For example, in some variations, described herein are medical sensing devices and systems including such devices that use ultrasound to digitally transmit biological parameters received by the medical sensing device to one or more telecommunications devices (e.g., a smartphone) where the information can be further processed and/or transmitted on. The executable logic may also be referred to as an adapter for adapting medical sensing devices so that they may ultrasonically transmit biological parameter information to a telecommunications device for further processing. Also described are systems and/or subsystems for use with a telecommunications device so that the telecommunications device can receive and translate an ultrasonically encoded health metric information signal. These subsystems may include client software (e.g., applications) to be run on the telecommunications device (e.g., phone) to translate the ultrasonic health information (or biological parameter) signal into a digital signal that can be uploaded, stored, and/or analyzed by the telecommunications device.

A medical sensing device may be any device for receiving biological parameters, such as patient vitals. The biological parameters may also be referred to as biometric data. For example, a medical sensing device may be a thermometer, blood pressure transducer, glucose monitor, pulse oximeter, pulse rate meter, pedometer, activity monitor, hydration monitor, etc. The medical sensing devices or systems referred to herein are typically digital systems because they may display a numeric (e.g., digital) representation of the biological parameter. For example, the devices may convert analog biological parameters (e.g., temperature, blood sugar, blood pressure, or any other health metric information) into digital signals that may be displayed or otherwise presented to the user. For example, a medical sensing system may include a digital thermometer for taking a subject's temperature, a blood cuff for presenting patient blood pressure, a blood sugar (glucose) monitors, a pulse oximeter, or the like, including combinations of these devices. Medical sensing systems or devices for home use are of particular interest, and especially those having sensors that monitor or collect biological parameters from patients and present the information on a display.

As described in greater detail below, in some variations the devices and systems format and/or encode the information so that it includes a hybrid of both digital (e.g., extracted and/or alphanumeric) information and analog (e.g., graphical) information. As used herein the phrase 'analog' refers to information that is sequentially ordered and may be graphically displayed to show a change or trend. The analog information may refer to a variable physical level that is quantified (e.g., a variable that varies over time). The actual information may be digital (e.g., by converting from continuous to discrete), but it may still be referred to as "analog" herein because it represents a change in one or more parameters over time, distance, or some other variation.

Any of the information transmitted as an ultrasonic signal (e.g., analog, digital, hybrid digital/analog, etc.) may be encrypted. For example, the information may be encrypted using an encryption key. The encryption key may be displayed or otherwise made available on or by the device transmitting the ultrasonic signal. In general, the encryption key may be input into a telecommunications device so that that particular device is then paired with the device including the ultrasonic modem and may receive and decrypt the information. Encryption of data may allow protection of patient-sensitive information. Encryption may also reduce the noise in the system, as it may limit the signals received to those that are properly encrypted.

As used herein biological parameters or information may include any patient information that is processed, sensed, and/or calculated by a medical sensing system, and particularly digitally encoded biological parameters. For example, biological parameters may include temperature, blood pressure, blood sugar level, pH, oxygenation, pulse rate, respiratory rate, or any other biological measurement, particularly those relevant to medical case, including diagnosis and health monitoring.

As used herein telecommunications devices includes smartphones (e.g., iPhone™ Droid™ or other personal communications devices), tablet computers (e.g., iPad, tablet PCs, or the like), and/or desktop computers that include (or may be adapted to include) a microphone capable of receiving ultrasonic sound. A telecommunications device may include logic for translating the digital signal encoded by the ultrasonic sound into a digital signal that can be displayed, uploaded/transmitted, stored, and/or analyzed.

Thus, in some variations, described herein are medical sensing devices for ultrasonically transmitting digital biological parameters. In some variations, the device may include: a sensor for detecting a biological parameter from a patient; a processor for encoding a digital representation of the biological parameter as an ultrasound sound signal; and an ultrasonic transducer for transmitting an ultrasonic sound signal from the processor.

For example, the sensor may be a transducer for transducing a biological parameter (temperature sensor, pressure sensor, etc.). The device may also include a controller (e.g., microcontroller) for processing signals from the sensor(s). The processor may include a signal generator that generates a signal from sensed and/or processed patient biological parameter information; the signal may be encoded for transmission. The signal may be encoded as a digital packet (e.g., words, bytes, etc.). For example, the signal may include a start bit, stop bit, information bit(s) identifying the type or source of the biological parameter (e.g., packet identifier), a digital representation of the biological parameter and in some variations a cyclic redundancy check (CRC) portion. In some variations, the signal (including the biometric measurement or data portion) can have a time and/or date stamp.

As mentioned, in some variations the system may be configured to encrypt the information and transmit only the encrypted information; the telecommunications device may be configured to receive the encryption key either directly (e.g., by taking and/or analyzing a figure describing the encryption key.

In some variations, the system or devices may be configured so that the measurement is made at time x and stored on the device (e.g., thermometer, glucometer, etc.) and transmitted to the telecommunications device (e.g., smartphone or tablet) ultrasonically at a later time, and eventually uploaded (e.g., to the cloud). In some variations, several time/date stamped measurements may be stored on a device and could be transmitted together in a burst to the telecommunications device. As described in greater detail below, although the device may be primarily one-way (e.g., sending data from the biometric device to the telecommunications device) in some variations, the devices may be configured to receive at least a confirmation signal and/or an indicator of the proximity of the telecommunications device. In some variations, the ultrasonic transducer may also be configured to receive a confirmation signal from the telecommunications device. Confirmation may indicate that the telecommunications device received a sent message (data) or that the telecommunications device is ready to receive the sent data, or both.

The ultrasonic transducer may be any appropriate transducer, including a piezo crystal transducer.

In some variations, a system for ultrasonically transmitting digital biological parameter includes: a medical sensing device having: a sensor for detecting a biological parameter, a processor for encoding a digital representation of the biological parameter as an ultrasound sound signal, and an ultrasonic transducer for transmitting the ultrasonic sound signal; and client control logic configured to be executed by a telecommunications device and to receive the ultrasonic sound signal and convert it back to a digital representation of the biological parameter.

The processor may convert some or the entire digital biological parameter signal (which is typically a numeric value) into an ultrasonic signal by the use of any appropriate signal processing technique, including, but not limited to, frequency-shift keying.

The client control logic may also be referred to as software (though it may be software, hardware, firmware, or the like), or a client application. The client control logic may execute on a telecommunications device. The client control logic may also include components for passing the digital representation of the biological parameter on to other devices, e.g., uploading it to a website or server, for example. In some variations, the client control logic may be configured to display or otherwise present the information locally on the telecommunications device.

Also described herein are systems for transmitting a digital health parameter, the system comprising: an ultrasonic transducer, wherein the ultrasonic transducer is capable of transmitting signals in an open-air environment at frequencies above about 17 KHz (e.g., 19 KHz, or centered around 20 KHz); and a signal generator configured to generate an ultrasonic signal corresponding to a digital representation of a biological parameter, wherein the identifier is associated with at least one frequency above about 17 KHz (e.g., 19 KHz, or centered around 20 KHz).

As an example, described herein are digital thermometer to ultrasonically transmit digital temperature information to a telecommunications device for further processing and transmission. The digital thermometer may include: a temperature sensor for sensing patient temperature; a signal generator for generating a signal corresponding to a digital representation of the patient temperature; and an ultrasonic transducer for transmitting the digital representation of the patient's temperature as an ultrasonic signal comprising one or more frequencies above 19 KHz. The thermometer may include an encryption key on the outside of the thermometer that may be imaged and/or viewed by a user and/or a telecommunications device configured to receive the ultrasonic signal.

In general, described herein are digital ultrasonic modem devices for ultrasonically and securely transmitting digital data. Such devices may include: a microprocessor; an ultrasonic transducer; an encryption key located on the device; and ultrasonic transmission logic that configures digital data for acoustic transmission by the ultrasonic transducer at frequencies at or above 17 KHz, the ultrasonic transmission logic further configured to encrypt the digital data according to the encryption key.

Any appropriate ultrasonic transducer may be used. For example, the ultrasonic transducer may be a piezoelectric speaker.

As mentioned, the encryption key may be visibly marked on the device, and may be configured as an alphanumeric code, a symbol, or the like. For example, the encryption key may be configured as a bar code, a QR code, etc.

Any of the systems described herein may be configured as systems for secure ultrasonic transmission of data, and may include: an ultrasonic communications device comprising an ultrasonic transducer, an encryption key located on the ultrasonic communications device, and ultrasonic transmission logic that configures digital data for acoustic transmission by the ultrasonic transducer at frequencies at or above 17 KHz, the ultrasonic transmission logic further configured to encrypt the digital data according to the encryption key; and decrypting logic executable on a telecommunications device, wherein the telecommunications device comprises a receiver for receiving an ultrasonic signal from the ultrasonic communications device, and wherein the decrypting logic is configured to receive the encryption key and apply the encryption key to decrypt the ultrasonic signal.

In general, the encryption key may be visible on the ultrasonic communications device, packing for the device, or the like.

In any of these variation described herein, the telecommunications device may include an input for inputting the encryption key, which may provide information to the decryption logic. For example, the input may be a camera for taking an image of the encryption key (e.g., bar code, QR code, etc.) and determine the encryption key therefrom. In some variations, the input comprises a manual input (e.g., keypad, touchscreen, etc.) for manually entering an encryption key.

Also described herein are methods of securely transferring information using ultrasound. For example, in some variations, the method includes receiving an encryption key that is present on an outer surface of an ultrasonic communication device; receiving an encrypted ultrasonic signal from the ultrasonic communications device; and decrypting the ultrasonic signal with the encryption key.

In some variations, the step of receiving an encryption key comprises taking the encryption keys from the outer surface of ultrasonic communications device. Decrypting the ultrasonic signal may include decrypting the ultrasonic signal in a telecommunications device. As mentioned, receiving the encryption key may comprise imaging the encryption key using a camera on the telecommunications device.

In general, any of the systems described herein may use hybrid digital and analog encoding. For example, a device for transmission of both digital and analog ultrasonic data (hybrid digital and analog data) may include: a microprocessor; an ultrasonic transducer; and hybrid transmission logic configured to generate a signal comprising digital data appended to analog data, for acoustic transmission by the ultrasonic transducer at frequencies at or above 17 KHz.

As mentioned above, the information maybe encoded with frequency shift keying (FSK); the FSK digital data may be appended to an analog data that has not been encoded by FSK but has been frequency modulated to form a hybrid digital/analog signal.

In any of these variations, the device may include a sensor for detecting a biological parameter from a patient, and/or a microprocessor configured to extract the digital data from the analog data. In some variations, the digital data comprises calibration data for the analog data (e.g., minimum, maximum, variable interval (e.g., time interval), scale, etc.). The analog data may comprise any appropriate signal, typically measured from a device sensor, such as: an EEG, a subject's temperature over time, a subject's glucose level over time, a subject's blood pressure over time, a subject's oxygen level over time, or a subject's physical activity over time, etc.

Also described herein are methods of transmitting a hybrid digital and analog signal using ultrasound. For example, a method may include: generating an ultrasound signal comprising digital data encoded with frequency shift keying (FSK) appended to an analog signal comprising a frequency modulated signal that is modulated at a frequency above 17 KHz; and acoustically transmitting the signal using an ultrasonic transducer.

The method may also include detecting a biological parameter from a patient, wherein the analog signal comprises the biological parameter. The method may also include extracting the digital data from the analog signal. The analog signal may comprise: an EEG, a subject's temperature over time, a subject's glucose level over time, a subject's blood pressure over time, a subject's oxygen level over time, or a subject's physical activity over time.

In some variations, the method also includes the step of receiving the ultrasound signal on a telecommunications device having an ultrasonic audio pickup.

In any of the variations described herein, the ultrasound signal may be stored before transmitting. Any of the variations described herein may be encoded with an error correction code. The method may also include retransmitting the ultrasound signal; the signal may be retransmitted a fixed number of times or it may be retransmitted continuously. In some variations, two-way communication may be used between the ultrasonic communications device and the telecommunications device including executable logic for receiving and/or decrypting the ultrasonic signal. Thus, in some variations the telecommunications device may be configured to transmit a signal back to the ultrasonic communications device. The ultrasonic communications device may include a receiver, or it may be adapted to receive a signal on the transmitter (e.g., piezo).

Also described herein are ECG sensing wristlets configured to transmit ECG information to a mobile telecommunications device or multiple devices.

For example, described herein are wireless, wearable wristlet devices to electrocardiographic (ECG) signals from a subject wearing such a device and ultrasonically transmit this information to a mobile telecommunications device. The wristlet device may include: a wristlet body configured to fit around a wrist; two or more electrodes for detecting ECG signals from the subject; an ultrasound transducer; and a processor coupled to the ultrasound transducer and configured to receive ECG signals from the two or more electrodes and to encode the signals to be transmitted as an ultrasound signal for transmission by the ultrasound transducer at frequency of above about 17 kHz.

The wristlet body may be configured as a strap (e.g., any type of watch strap), band, bracelet, or the like. In some variations, the wristlet includes a "face" region that may be worn on the top of the subject' wrist, facing upwards. The wristlet may include a pair of electrodes (or more than two electrodes). For example, in some variations the wristlet includes an inner electrode facing the wearer's wrist when the wristlet is worn, so that it may make reliable contact with the wearer's skin when worn. A second electrode may be located on the face or side of the wristlet; this second electrode may be configured to allow the wearer to touch the wristlet with the opposite hand/arm. In some variations, a third electrode may be located on the wristlet. For example, the third electrode may be present on a side of the wristlet and configured so that the subject may touch the third electrode to another portion of the body (e.g., the chest, leg, etc.).

The processor may be configured to encode the signals to be transmitted as an ultrasound signal for transmission by the ultrasound transducer at a frequency of between about 17 kHz and about 30 kHz (or any of the other ranges specified herein, including greater than 16 kHz, greater than 17 kHz, greater than 18 kHz, etc.). In general, the processor may be configured to encode the signals to be transmitted as hybrid signals comprising digital information appended to an analog signal.

The device may also be configured to receive signals (e.g., ultrasound signals), including ultrasound signals from a mobile telecommunications device. In some variations, the device further comprises an ultrasound receiver configured to receive an ultrasound signal from the mobile telecommunications device. This may also create pairing of the information between the devices (e.g., for synching, confirming transfer of information, etc.). A separate receiving ultrasound transducer may be used, or the same ultrasound transducer may be configured to both send and receive. For example, an ultrasound transducer may be configured to transmit signals from the processor as ultrasound signals and to receive ultrasound signals (e.g., from the mobile telecommunications device).

In some variations, the devices (wristlet) described herein may be configured to operate with extremely low power. As mentioned above, the device may include a battery having a voltage of less than 1.8 V.

In general, the devices described herein may generally be configured to operate in real time. In particular, ECG information may be received and transmitted in real time; the mobile telecommunications device may display (and/or retransmit) in real time. For example, the processor may be configured to transmit the encoded ECG signals in real time.

In general, any of the wristlet devices may be configured without a display or output, or with only an audible output (e.g., beep, tone) or with an LED (e.g., simple indicator light). Instead, the device may rely on communication with a base station such as a mobile telecommunications device to display, and in some cases analyze, the signal. For example, the device may include an indicator indicating when the device is communicating with the mobile telecommunications device. Thus, wristlet devices that do not include a display for displaying ECG information may make the devices smaller, lighter and less expensive to manufacture and operate.

Further, in some variations, the devices may be configured to store one much of the date, e.g., ECG data, and transmit it once a receiver such as a mobile phone is ready to receive it. Any of these variations may therefore append additional information such as time/date stamp, user input data, etc. Thus, in some variations, the device further comprises a memory coupled to the processor and configured to store the encoded signals for later transmission.

In some variations, the processor is configured to encode the signals to be transmitted as digital signals, as discussed above.

In general, the devices (e.g., the processor) may also be configured to determine when the mobile telecommunications device has received the encoded signals from the device.

The wristlet devices described herein may also be configured as a time piece, and may include a watch face or the like.

Also described herein are wireless, wearable wristlet devices to detect electrocardiographic (ECG) signals from a subject wearing the device and ultrasonically transmit this information to a mobile telecommunications device, the wristlet device comprising: a wristlet body configured to fit around a wrist; two or more electrodes for detecting an ECG signal from the subject; an ultrasound transducer; and a processor coupled to the ultrasound transducer and configured to receive the ECG signal from the two or more electrodes and to encode the signals to be transmitted as a hybrid ultrasound signal comprising digital information appended to an analog representation of the ECG signal for transmission by the ultrasound transducer at frequency of above about 17 kHz.

As described herein, the hybrid ultrasound signal may be configured to encode the digital information with frequency shift keying (FSK) and append the FSK digital signal to the analog signal that has not been encoded by FSK but has been frequency modulated. For example, the processor may be configured to extract the digital information from the ECG signal. In some variations, the digital information comprises calibration data for the analog signal. The processor may be configured to encode the signals to be transmitted as an ultrasound signal for transmission by the ultrasound transducer at any appropriate ultrasound frequency (e.g., frequency above the normal audible range), such as those described herein, for example, at a frequency of between about 17 kHz and about 30 kHz.

In any of these device variations, the device may be configured to both send and receive ultrasound signals. For example, the device may include an ultrasound receiver configured to receive an ultrasound signal from the mobile telecommunications device. In some variations, the same transducer used to transmit an ultrasound signal (e.g., the ECG signal) may also be configured to receive and ultrasound signal (e.g., readiness to receive, request for transmission, confirmation of transmission, request for re-transmission, etc.). The ultrasound transducer may be configured to transmit signals from the processor as ultrasound signals and to receive ultrasound signals from the mobile telecommunications device.

Also described herein are wireless, wearable wristlet devices to detect electrocardiographic (ECG) signals from a subject wearing the device and ultrasonically transmit this information to a mobile telecommunications device, the wristlet device comprising: a wristlet body configured to fit around a wrist; two or more electrodes for detecting ECG signals from the subject; an ultrasound transducer configured to transmit and receive ultrasound signals; and a processor coupled to the ultrasound transducer and configured to receive ECG signals from the two or more electrodes and to encode the signals to be transmitted as an ultrasound signal for transmission by the ultrasound transducer at frequency of above about 17 kHz; further wherein the processor is configured to receive ultrasound signals from the mobile telecommunications device.

Aspects of the present disclosure also provide a wireless, wearable wristlet device to detect electrocardiographic (ECG) signals from a subject wearing the device and wirelessly (e.g., ultrasonically) transmit this information to a mobile telecommunications device. The wristlet device may comprise a wristlet body configured to fit around a wrist, two or more electrodes for detecting ECG signals from the subject, a wireless (e.g., ultrasound) transducer, and a processor. The processor may be coupled to the wireless transducer and may be configured to receive ECG signals from the two or more electrodes and to encode the signals to be transmitted as a wireless signal (e.g., an ultrasound signal for transmission by the ultrasound transducer at frequency of above about 17 kHz).

The processor may be configured to encode the signals to be transmitted as an ultrasound signal for transmission by the ultrasound transducer at a frequency of between about 17 kHz and about 30 kHz. The processor may be configured to encode the signals to be transmitted as hybrid signals comprising digital information appended to an analog signal. The device may further comprise an ultrasound receiver configured to receive an ultrasound signal from the mobile telecommunications device The ultrasound transducer may be configured to transmit signals from the processor as ultrasound signals and to receive ultrasound signals from the mobile telecommunications device.

The device may further comprise a battery having a voltage of less than 1.8. The processor may be configured to transmit the encoded ECG signals in real time. The device may further comprise a memory coupled to the processor and configured to store the encoded signals for later transmission. The processor may be configured to encode the signals to be transmitted as digital signals. The device may further comprise an indicator indicating when the device is communicating with the mobile telecommunications device. The processor may be further configured to determine when the mobile telecommunications device has received the encoded signals from the device. The device may be configured as a time piece.

Aspects of the present disclosure also provide a wireless, wearable wristlet device to detect electrocardiographic (ECG) signals from a subject wearing the device and wirelessly (e.g., ultrasonically) transmit this information to a mobile telecommunications device. The wristlet device comprises a wristlet body configured to fit around a wrist, two or more electrodes for detecting an ECG signal from the subject, a wireless (e.g., ultrasound) transducer, and a processor. The processor may be coupled to the wireless (e.g., ultrasound) transducer and configured to receive the ECG signal from the two or more electrodes and to encode the signals to be transmitted as a hybrid wireless (e.g., ultrasound) signal comprising digital information appended to an analog representation of the ECG signal for transmission. The ultrasound transducer may transmit the signal at frequency of above about 17 kHz.

The hybrid ultrasound signal may be configured to encode the digital information with frequency shift keying (FSK) and append the FSK digital signal to the analog signal that has not been encoded by FSK but has been frequency modulated. The processor may be configured to extract the digital information from the ECG signal. The digital information may comprise calibration data for the analog signal. The processor may be configured to encode the signals to be transmitted as an ultrasound signal for transmission by the ultrasound transducer at a frequency of between about 17 kHz and about 30 kHz. The ultrasound receiver may be configured to receive an ultrasound signal from the mobile telecommunications device. The ultrasound transducer may be configured to transmit signals from the processor as ultrasound signals and to receive ultrasound signals from the mobile telecommunications device.

The device may further comprise a battery having a voltage of less than 1.8 V. The processor may be configured to transmit the encoded signals in real time. The device may further comprise a memory coupled to the processor and configured to store the encoded signals for later transmission. The processor may be configured to encode the signals to be transmitted as digital signals. The device may further comprise an indicator indicating when the device is communicating with the mobile telecommunications device. The processor may be further configured to determine when the mobile telecommunications device has received the encoded signals from the device. The device may be configured as a time piece.

Aspects of the present disclosure also provide a wireless, wearable wristlet device to detect electrocardiographic (ECG) signals from a subject wearing the device and wirelessly (e.g., ultrasonically) transmit this information to a mobile telecommunications device. The wristlet device may comprise a wristlet body configured to fit around a wrist, two or more electrodes for detecting ECG signals from the subject, a wireless (e.g., ultrasound) transducer configured to transmit and receive ultrasound signals, and a processor coupled to the wireless (e.g., ultrasound) transducer and configured to receive ECG signals from the two or more electrodes and to encode the signals to be transmitted as a wireless (e.g., ultrasound) signal for transmission by the wireless (e.g., ultrasound). The ultrasound transducer may transmit the signal at frequency of above about 17 kHz. The processor may be configured to receive ultrasound signals from the mobile telecommunications device.

Wearable computing devices may also be in the form of a wristlet or an armband. Aspects of the present disclosure also provide an external housing or cover for wrist or arm worn computing devices. The external housing or cover may comprise two or more electrodes for detecting ECG signals from the subject and a wireless transmitter to transmit the ECG signal to the wrist or arm worn computing device.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the invention are utilized, and the accompanying drawings of which:

FIGS. 3A-3F show a biometric or physiological parameter measurement and monitoring system comprising a tablet computer and a protective tablet computer case, in accordance with many embodiments;

FIG. 10A is a front view of another variation of an apparatus as described herein, configured as a case that is shown empty, though adapted to hold a mobile telecommunications device;

FIGS. 10B-10D show left side, back, and right side views, respectively, of the apparatus of FIG. 4A (in this example, the leg (first) electrode is on the left side of the case);

FIGS. 14A-14C illustrate another variation of an apparatus as described herein from the left side, back, and right side views, respectively (in this example, the left (first) electrode is on the left side of the case and the second and third electrodes are part of an electrode unit held by the case on the back surface);

FIGS. 15A-159C illustrate another variation of an apparatus as described herein from the left side, back, and right side views, respectively (in this example, the leg (first) electrode is on the back surface between the second and third electrodes);

FIG. 21C is a schematic representation of a system including a medical sensing device that is configured to ultrasonically transmit and receive data (e.g., ECG data) encoding one or more biological parameter to a telecommunications device such as a smartphone;

DETAILED DESCRIPTION

Devices, systems, and methods for measuring and monitoring biometric or physiological parameters in a user-friendly and convenient manner are disclosed.

It is to be understood that the present disclosure is not limited in its application to the details of construction, experiments, exemplary data, and/or the arrangement of the components set forth in the following description. The inventions of the present disclosure are capable of other embodiments or of being practiced or carried out in various ways. Also, it is to be understood that the terminology employed herein is for purpose of description and should not be regarded as limiting.

In the following detailed description of embodiments of the present disclosure, numerous specific details are set forth in order to provide a more thorough understanding of the disclosure. However, it will be apparent to one of ordinary skill in the art that the concepts within the disclosure can be practiced without these specific details. In other instances, well-known features have not been described in detail to avoid unnecessarily complicating the description.

ECG Monitor Form Factors and Methods of Use

Figure 1:
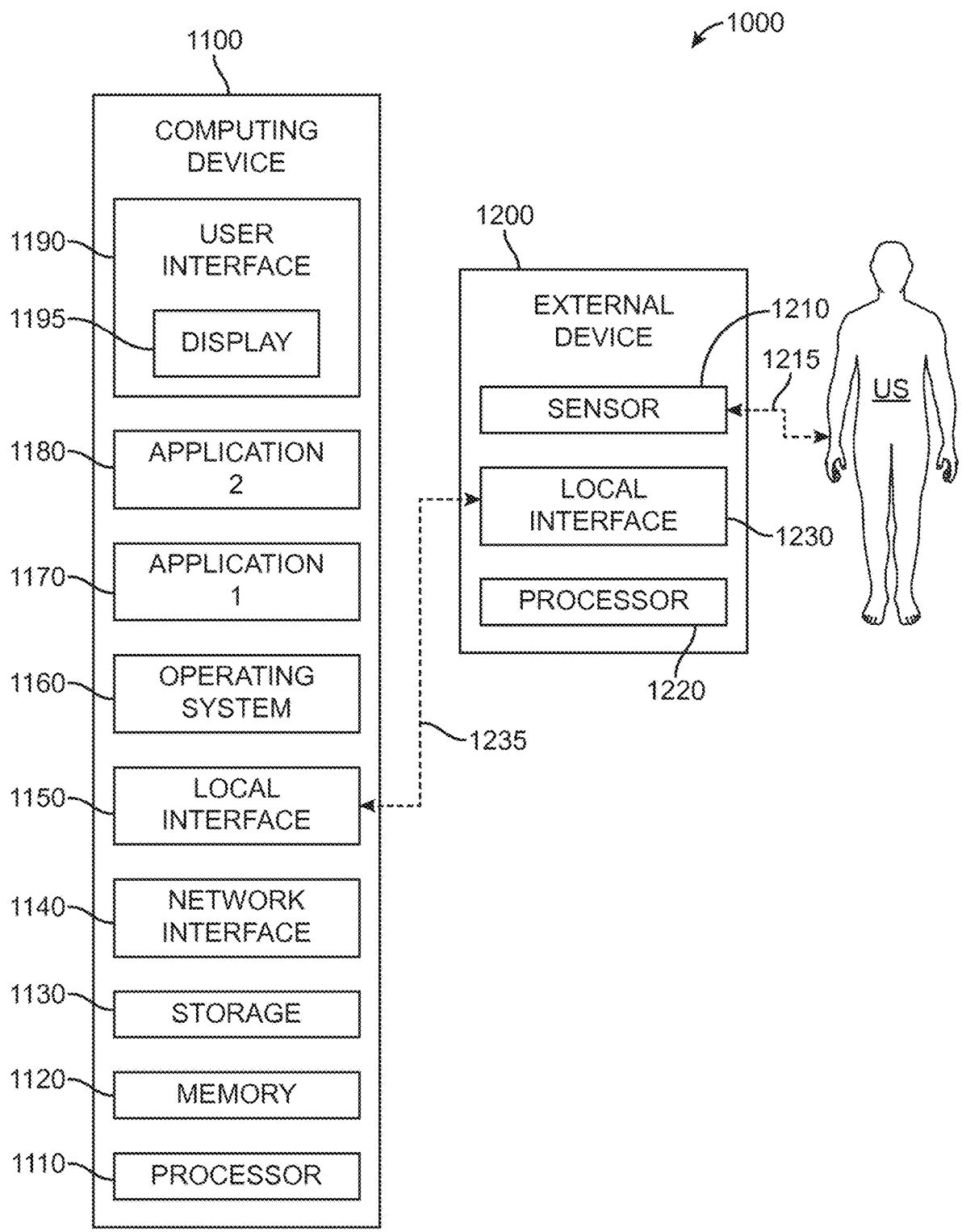
FIG. 1 shows a schematic diagram of a system for measuring and monitoring biometric or physiological parameters, in accordance with many embodiments.

FIG. 1 shows a schematic diagram of a system 1000 for measuring and monitoring one or more biometric or physiological parameters of a user US. The system 1000 may comprise a computing device 1100 and an external sensor device 1200 for coupling or removably attaching to the computing device 1100. The computing device 1100 may comprise one or more of a personal computer, a laptop computer, a tablet computer (such as an Apple iPad, an Apple iPod, a Google Nexus tablet, a Samsung Galaxy tablet, a Microsoft Surface, etc.), a personal digital assistant (PDA), a smartphone (such as an Apple iPhone, a Google Nexus phone, a Samsung Galaxy smartphone, etc.), or a wearable computing device (such as a Google Glass, a Samsung Galaxy Gear Smart Watch, etc.). In many embodiments, the computing device comprises a tablet computer or a smartphone. The external sensor device 1200 may be configured to removably couple to the computing device 1100 and may comprise a cover for covering the computing device, such as a tablet computer case or a smartphone case or cover. In this manner, the external sensor device 1200 may not need to be replaced as the user US replaces or upgrades his or her computing device 1100. That is, the same external sensor device 1200 may be used by the user for the different computing devices 1100 the user may have.

The computing device 1100 may comprise a processor 1110, a memory unit 1120 such as a RAM module, a data storage unit 1130 (e.g., a flash memory module, a hard drive, a ROM, etc.), a network interface 1140 configured to connect with a cellular data network (e.g, using GSM, GSM plus EDGE, CDMA, quadband, or other cellular protocols) or a WiFi (e.g., a 802.11 protocol) network, for example, a local interface 1150, an operating system 1160 which may be stored on the data storage unit 1130, loaded onto the memory unit 1120, and implemented by the processor 1110, a first application 1170 such as a first mobile software application ("mobile app") downloaded from an online application distribution platform, a second application 1180 such as a second mobile software application ("mobile app") downloaded from the online application distribution platform, and a user interface 1190. For example, the online application distribution platform may be the Apple App Store, Google Play, Windows Phone Store, BlackBerry App World, or the like. The operating system 1160 may comprise instructions for operating the computing device 1100. The user interface 1190 may comprise a display 1195 for displaying one or more components of the operating system 1160, the first application 1170, or the second application 1180. For example, the display 1195 may be a touch screen display for manipulating and controlling the operating system 1160, the first application 1170, or the second application 1180. One or more of these elements may be combined or omitted. The computing device 1100 may further comprise other components such as motion detection components, one or more cameras, additional displays, power supplies, fans, various I/O ports, etc.

The external device 1200 may comprise a sensor 1210, a processor 1220, and a local interface 1230. The sensor 1210 is configured couple with the user US through a connection 1215, physical contact for example, to sense or detect one or more physiological parameters of the user US. Generally, the one or more physiological parameters comprises a cardiac parameter such as of a heart rate, a heart rate variability, a blood pressure, a blood pressure variability, an arrhythmia, a seisomocardiogram (SCG), an SCG parameter, an electrocardiogram (ECG), or an ECG parameter of the user. Other physiological parameters are also contemplated. For example, the sensor 1210 may comprise an activity sensor, a blood glucose sensor, a blood oxygenation sensor, a thermometer, a respiratory sensor, a metabolic sensor, an odor detector, or the like. The processor 1220 may receive the detected physiological parameter and process it into a signal for the local interface 1230 to send to the local interface 1150 of the computing device 1100 through a connection 1235. The connection 1235 may comprise a wired such as a USB connection, a Firewire connection, a Lightning connection, or the like. Alternatively or in combination, the connection 1235 may comprise a wireless connection such as a WiFi connection, a BlueTooth connection, a low power BlueTooth connection, an NFC (near field communication) connection, a near field ultrasound communication connection as described in U.S. Pat. Nos. 8,301,232 and 8,509,882, or the like.

The first application 1170 may be stored in the storage 1130 of the computing device 1100, loaded onto the memory 1120 of the computing device 1100, and may be run using the processor 1110 and the operating system 1160. The processor 1110, under instructions from the first application 1170, may be coupled to the local interface 1150 of the computing device 1100 to receive the detected physiological parameter(s). Furthermore, the processor 1110, under instructions from the first application 1170, may store the received physiological parameter(s) in one or more of the memory 1120 or storage 1130 of the computing device. The stored physiological parameter(s) may be time-stamped and tagged with user identify information for later access and analysis. The processor 1100, under instructions from the first application 1170, may also cause the physiological parameter to be displayed on the display 1195 of the user interface. For example, the physiological parameter may be displayed in real-time as it is measured. The first application 1170 may also comprise algorithms run by the processor 1100 to analyze the physiological data and may present the interpretations and analysis to the user US. For example, if an arrhythmia is detected, the processor 1100, under instructions from the first application 1170, may alert the user US or even a remote healthcare provider such as a physician, nurse, or hospital through the network interface 1140. Furthermore, the processor, under instructions from the first application 1170, may be configured to send the physiological data to a remote computing device, a remote server, or a remote healthcare provider such as a physician, nurse, or hospital automatically through the network interface 1140.

In some embodiments, the processor 1110, under instructions from the first application 1170 or other applications, may use the measured physiological parameter(s) to identify or authenticate the user and perform an operation based on the identity of the user. For example, the user may be authenticated based on the attributes of the user's heartbeat. The durations of particular portions of a user's heart rhythm, the relative size of peaks of a user's electrocardiogram (ECG), or other relevant amplitudes or amplitude ratios can be processed and compared to a stored profile to authenticate the user. The processor 1100, under instructions from the first application 1170 or other applications, may be used to generate the reference profile. In some embodiments, the processor 1100, under instructions from the first application 1170 or other applications, may use the measured physiological parameter(s) to determine the user's mood and provide related data.

The electrical activity of the user US's heart can be detected and analyzed, for example. A typical heartbeat may include several variations of electrical potential, which may be classified into waves and complexes, including a P wave, a QRS complex, a T wave, and sometimes U wave as known in the art. The shape and duration of the P wave can be related to the size of the user's atrium (e.g., indicating atrial enlargement) and can be a first source of heartbeat characteristics unique to a user.

The QRS complex can correspond to the depolarization of the heart ventricles, and can be separated into three distinct waves—a Q wave, a R wave and a S wave. Because the ventricles contain more muscle mass than the atria, the QRS complex is larger than the P wave. Also, the His/Purkinje system of the heart, which can increase the conduction velocity to coordinate the depolarization of the ventricles, can cause the QRS complex to look "spiked" rather than rounded. The duration of the QRS complex of a healthy heart can be in the range of 60 to 100 ms, but can vary due to abnormalities of conduction. The duration of the QRS complex can serve as another source of heartbeat characteristics unique to a user.

The duration, amplitude, and morphology of each of the Q, R and S waves can vary in different individuals, and in particular can vary significantly for users having cardiac diseases or cardiac irregularities. For example, a Q wave that is greater than ⅓ of the height of the R wave, or greater than 40 ms in duration can be indicative of a myocardial infarction and provide a unique characteristic of the user's heart. Similarly, other healthy ratios of Q and R waves can be used to distinguish different users' heartbeats.

The electrical activity of the user US's heart can also include one or more characteristic durations or intervals that can be used to distinguish different users. For example, the electrical activity of the heart may include PR intervals and ST segments as known in the art. A PR interval can be measured from the beginning of P wave to the beginning of a QRS complex. A PR interval can typically last 120 to 200 ms. A PR interval having a different duration can indicate one or more defects in the heart, such as a first degree heart block (e.g., a PR interval lasting more than 200 ms), a pre-excitation syndrome via an accessory pathway that leads to early activation of the ventricles (e.g., a PR interval lasting less than 120 ms), or another type of heart block (e.g., a PR interval that is variable). An ST segment can be measured from a QRS complex to a T wave, for example starting at the junction between the QRS complex and the ST segment and ending at the beginning of the T wave. An ST segment can typically last from 80 to 120 ms, and normally has a slight upward concavity. The combination of the length of ST segment, and the concavity or elevation of ST segment can also be used to generate characteristic information unique to each user's heartbeat.

A T wave can represent the repolarization or recovery of the ventricles. The interval from the beginning of the QRS complex to the apex of the T wave can be referred to as the absolute refractory period. The last half of the T wave can be referred to as the relative refractory period or vulnerable period. The amplitude of the T wave, the duration of the absolute refractory period, and the relative refractory period can also be used to define a characteristic of the user's heart rate.

The QT interval, which can represent the total time needed for the ventricles to depolarize and repolarize, can be measured from the beginning of a QRS complex to the end of a T wave. The QT interval can typically last between 300 and 450 ms, and can vary based on the condition of the user's heart rate. Several correction factors have been developed to correct QT interval 222 for the heart rate. Both the measured and corrected QT interval values can be used to define a unique characteristic of a user's heartbeat.

Because a user US's heartbeat or heart rate can vary slightly based on the user US's activity or mood, each authorized user US can initially provide a base or standard heart rate, heartbeat, or electrical activity to the device prior to first use. The first application 1170 may be run by processor 1110 to record this baseline reading. For example, the external device or sensor 1200 can sample several heartbeats or electrical activity at several different times to detect variations in the user US's cardiac electrical activity. This data may be sent to the computing device 1100. The processor 1110, under instructions from the first application 1170, may then process the detected signals to determine several unique characteristics of the user US's heart activity, and identify a range of suitable characteristic values for each of the processed characteristics. Based on the characteristic values and associated ranges, the processor 1110 can select one, all or a subset of the characteristics to define a unique heart activity profile for the authorized user US. The particular combination of characteristics and associated ranges can be selected to minimize overlap with other authorized users, or based on characteristic values and ranges that do not fall within a range of average values and ranges (e.g., do not use characteristic values and ranges that an average user of the device would have).

The system 1000 may be used to authenticate the user US based on the measured electrical activity of the user US's heart as compared with the generated profile. If the measured electrical activity matches the generated profile, the processor 1110, under instructions from the operating system 1160, the first application 1170, or other applications, may authenticate the user US. The processor 1110 can also be instructed to perform any suitable operation in response to identifying and authenticating the user US. In some embodiments, the processor 1110 can be instructed to provide access to restricted applications, for example applications for which only particular users have licenses or that only particular users have purchased. In some embodiments, the processor 1110 can be instructed to provide access to particular data or application settings associated with an authorized user US. For example, the processor 1110 can instructed to provide access to the identified user US's contact list, or to the identified user US's e-mail account or telephone history. As another example, the processor 1110 can be instructed to allow the user US to access private banking applications, or conduct financial transactions (e.g., transferring funds to different accounts, or purchasing merchandise) using the electronic device. In some embodiments, the computing device 1100 can load user US settings and profiles for providing a customized display to the user. For example, the computing device 1100 can display icons or options in the manner set by the user, or provide displays using a color scheme, fonts, or other customizable display attribute that are associated with the identified user.

In some embodiments, the system 1000 can use the detected heart rate or heartbeat characteristics to determine the user US's mood. In particular, because the allowable determined characteristics associated with each user US can include a range of values, the processor 1110 can be instructed to determine the distribution of the detected characteristics in the allowable characteristic ranges. Using the determined distribution, the processor 1110 can establish a user's mood and provide electronic device operations or data (e.g., media) associated with the extrapolated mood.

In some embodiments, the computing device 1100 can provide media playback based on the user US's detected mood or cardiac signal. For example, the computing device 1100 can identify media having beats per minute or other characteristics that are associated with or related to the user US's cardiac signal or heart rate, and play back the identified media. As another example, the media provided can have beats per minute faster or slower than the user's current heart rate to direct the user to work harder (e.g., during a workout) or to cool or calm the user down (e.g., at the end of a workout).

An aspect of the present disclosure may also include a process for performing a computing device operation based on a user US's cardiac signal. In a first step, the system 1000 may detect a user US's cardiac signal. For example, the user US's heart rate or heart beat may be detected using the sensor 1210 of the external device 1200. The external device 1200 may send the detected signal to the computing device 1100 through the connection 1235. The computing device 1100 can process the received signal using any suitable approach including determining the unique characteristics of the signal. Such characteristics can include, for example, durations between peaks in an EKG signal, peak values or rations between peaks in the EKG signal, or any other suitable characteristic as described herein. In a further step, the computing device 1100 can determine whether the user US detected earlier is an authorized user. For example, the computing device 1100 can compare the determined characteristics of the detected cardiac signals with a library of signals associate with known authorized users. If the computing device 1100 determines that the user US is not authorized (e.g., the characteristics of the detected cardiac signal do not match characteristics of a cardiac signal stored in memory), the computing device 1100 can prevent access to restricted electronic device operations in a further step. For example, the computing device 1100 can prevent the user from accessing personal or private information associated with other users. As another example, the computing device 1100 can prevent the user US from accessing applications or operations associated with particular users (e.g., applications purchased by particular users). As still another example, the computing device 1100 can prevent the user US from accessing any electronic device operation (e.g., no operation except for emergency calls).

If the computing device instead determines that the user US is authorized, the process can move to a fourth step in which the computing device 1100 determines the restricted operations that are associated with the user US. For example, the computing device 1100 can determine the particular private data associated with the authorized user (e.g., e-mail accounts, contact lists and banking information). As another example, the computing device 1100 can determine the particular operations or applications associated with the authorized user US (e.g., applications purchased by the user US using an applications store, or system controlling operations associated with an administrative account). At a fifth step, the computing device 1100 can provide access to the user US's determined restricted operations. For example, the computing device 1100 can load determined data. As another example, the computing device 1100 can provide links for launching determined personal or private applications.

The first application 1170 may also run in the background of the operating system 1160 to one or more of receive, store, and analyze physiological data as the second application 1180 is in the foreground of the display 1195 and is actively being manipulated by the user US. For example, the second application 1180 may comprise an e-mail application, a web browser, a music player, or a game which the user US operates as the first application 1170 and the external sensor device 1200 measure physiological parameter(s) of the user in the background.

The external sensor device 1200 may comprise many form factors depending on the form of the computing device 1100 and convenience to the user US, for example.

Figure 2A:
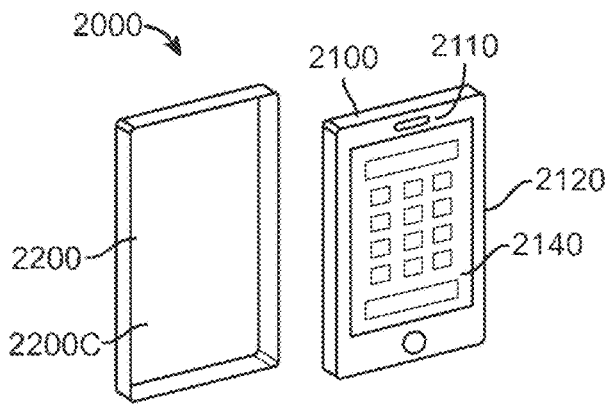
FIGS. 2A-2K show a biometric or physiological parameter measurement and monitoring system comprising a smartphone and a protective smartphone case, in accordance with many embodiments.
Figure 2B:
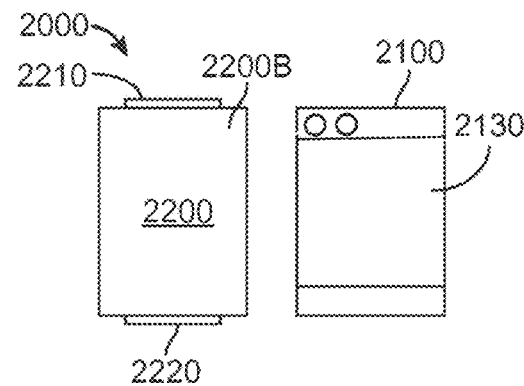
Figure 2C:
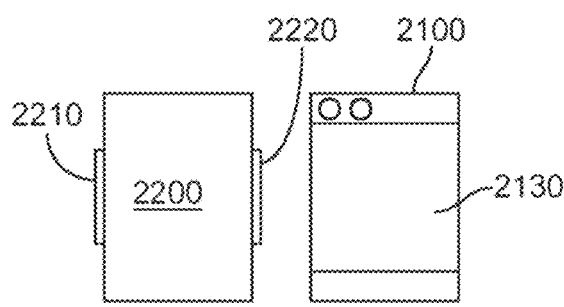
Figure 2D:
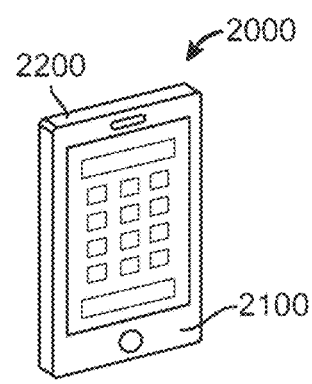

FIGS. 2A-2K show a biometric or physiological parameter measurement and monitoring system 2000 comprising a smartphone 2100 and a protective smartphone case 2200. FIG. 2A shows a perspective view of the system 2000 in which the smartphone 2100 and the protective smartphone case 2200 are separated. The protective case 2200 has a cavity 2200C for accommodating the smartphone 2100. FIGS. 2B and 2C show back views of the system 2000. FIG. 2D show a perspective view of the system 2000 in which the smartphone 2100 and the protective smartphone case 2200 are coupled or removably attached to one another. The smartphone 2100 may comprise, for example, an Apple iPhone, a Google Android smartphone, a Google Nexus, a Samsung Galaxy phone, an HTC smartphone, a Nokia Windows smartphone, a Blackberry smartphone, or the like.

The smartphone 2100 may comprise a front face 2110, edges 2120, a back face 2130, and a display 2140 on the front face 2110. The protective smartphone case 2200 may comprise a plurality of electrode leads for detecting physiological parameters such as an electrocardiogram (ECG). The plurality of electrode leads may comprise a first electrode lead 2210 and a second electrode lead 2220. When the smartphone 2100 and the protective case 2200 are coupled together, at least some of the plurality of electrode leads will be disposed over the edges 2120 of the smartphone 2100. In this manner, the thin and low-profile of the smartphone 2100 can be maintained for the user's convenience for example. As shown in FIG. 2B, the first and second electrode leads 2210 and 2220 may be disposed opposite of one another on the top and bottom edges (i.e., the shorter edges), respectively, of the protective case 2200. As shown in FIG. 2C, the first and second electrode leads 2210 and 2200 may be disposed opposite of one another on the left and right edges (i.e., the longer edges), respectively, of the protective case 2200. FIGS. 2B and 2C show a back side 2200B of the protective case 2200. Each electrode lead will generally be electrically isolated from one another to avoid shorting or interference. Each electrode lead will also generally minimally protrude from the body of the protective case 2200. For example, each electrode lead may be polished, roughened, or otherwise finished to match the exterior surface of the protective case 2200.

The sensor electrode leads described herein can be constructed from any suitable material. The electrode leads may be constructed from a specific material selected for particular conductive properties that permit a more effective transmission of the electrical signals reflecting the user's cardiac activity, for example. The electrode leads may be constructed from a silver based compound, which can provide superior conductivity relative to other metallic compounds (e.g., steel or aluminum). The size and location of the electrode leads may also be selected to ensure that sufficient contact is made between the user (e.g., the user's hand or finger) and the electrode leads. For example, each electrode lead may include a pad or extended area placed on the outer surface of the body of the external sensor device 1200.

Figure 2E:
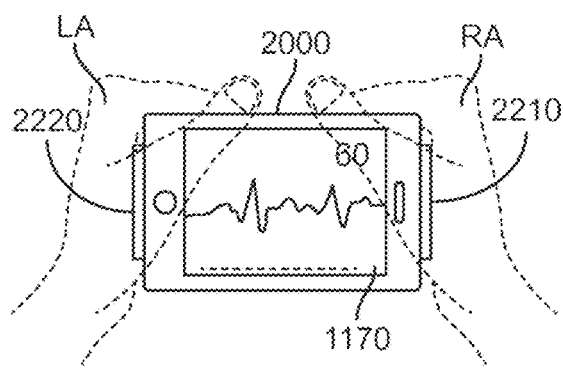
Figure 2F:
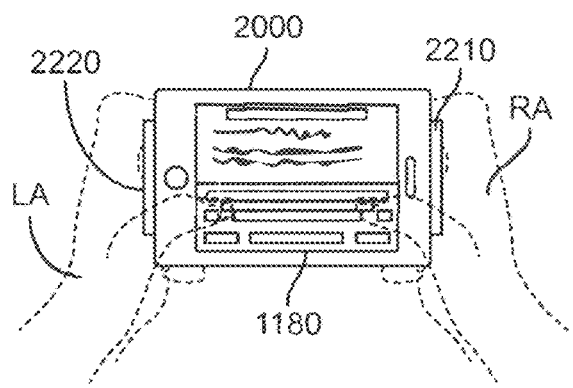

In use, the user may hold the system 2000 with their hands to contact the first electrode lead 2210 with a right arm RA of the user and to contact the second electrode lead 2220 with a left arm LA of the user to measure one or more physiological parameter such as a heart rate or an ECG as shown in FIGS. 2E and 2F. As shown in FIG. 2E, the first application 1170 may be active on the system 2000 and be displaying in real-time the measured parameters. As shown in FIG. 2F, the second application 1180, an e-mail application for example, may be active on the system 2000 and may be manipulated by the user US as the first application 1170 receives physiological parameter data in the background. By contacting the plurality of electrode leads with the right arm RA and the left arm LA, a Lead I ECG may be measured. The user US may also contact the first electrode lead 2210 with the right arm RA and the left leg LL to measure a lead II ECG. The user US may also contact the first electrode lead 2210 with the right arm RA and the left leg LL to measure a lead III ECG.

Figure 2G:
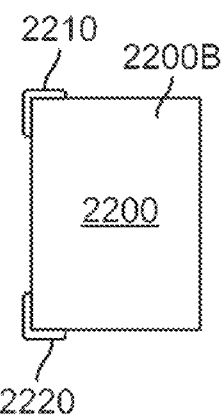
Figure 2H:
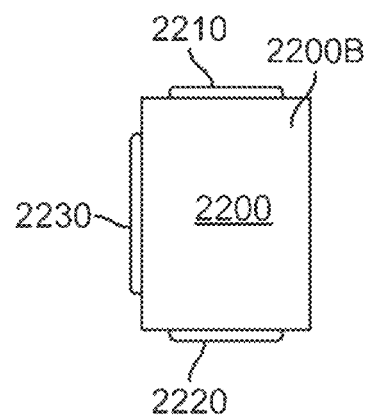
Figure 2I:
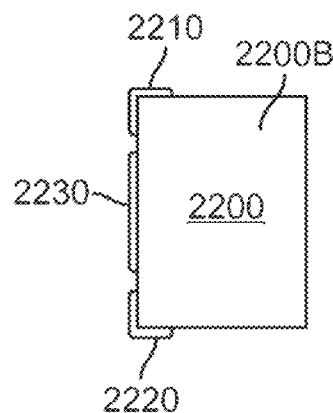
Figure 2J:
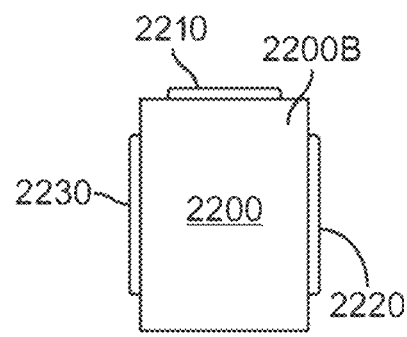

Other placements of the plurality of electrode leads are also contemplated. As shown in FIG. 2G, the first and second electrode leads 2210 and 2220 may be disposed on the corners of the protective case 2200. Furthermore, the plurality of electrode leads may include a third electrode lead 2230. As shown in FIG. 2H, the first and second electrode leads 2210 and 2220 may be disposed on the top and bottom edges (i.e., the shorter edges) of the protective case 2200 while the third electrode lead 2230 may be present on a side or longer edge of the protective case 2200. As shown in FIG. 2I, the first and second electrode leads 2210 and 2220 may be disposed on opposing corners of the protective case 2200 while the third electrode lead 2230 may be present on a side or longer edge of the protective case 2200. As shown in FIG. 2J, the first and second electrode leads 2210 and 2220 may be disposed on the left and right edges (i.e., the longer edges) while the third electrode lead 2230 may be present on a side or longer edge of the protective case 2200. In some embodiments, the first and second electrode leads 2210 and 2220 may be disposed on the edges of the protective case 2200 and the third electrode lead 2230 may be disposed on the back face 2200B of the protective case 2200.

Figure 2K:
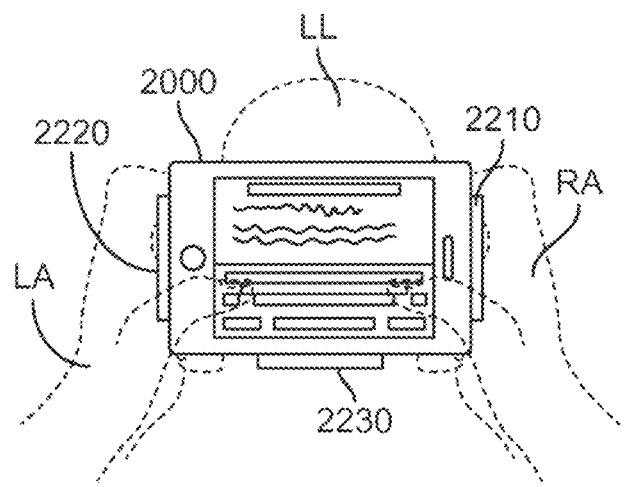

In use, the user may hold the system 2000 with their hands to contact the first electrode lead 2210 with a right arm RA of the user and to contact the second electrode lead 2220 with a left arm of the user and contact the third electrode lead 2230 with the left leg LL of the user to measure one or more physiological parameter such as a heart rate or an ECG as shown in FIG. 2K. As shown in FIG. 2K, the second application 1180, an e-mail application for example, may be active on the system 2000 and may be manipulated by the user US as the first application 1170 receives physiological parameter data in the background. By contacting the plurality of electrode leads with the right arm RA, the left arm LA, and the left leg LL, Lead I, Lead II, and Lead III ECGs may be measured. The Lead I, Lead II, and Lead III ECGs may even be measured concurrently. Wireless ECG apparatuses with three-electrodes are further described in co-owned U.S. Provisional Patent Application No. 61/845,254, filed on Jul. 11, 2013 and entitled "Three-Electrode Wireless ECG Apparatus," the contents of which are incorporated herein by reference.

FIGS. 3A-3F show a biometric or physiological parameter measurement and monitoring system 3000 comprising a tablet computer 3100 and a protective tablet computer case 3200. The system 3000 may be similar to the system 2000 in many ways. Whereas the system 2000 is adapted for use with a smartphone 2100, the system 3000 is adapted for use with a tablet computer 3100. The tablet computer 3100 may comprise an Apple iPad, a Google Nexus tablet computer, a Samsung Galaxy tablet computer, a Microsoft Surface tablet computer, or the like.

FIG. 3A shows a perspective view of the system 3000 in which the protective case 3200 has a cavity 3200C for accommodating the tablet computer 3100. The tablet computer 3100 has a front face 3110, edges 3120, a back face 3130, and a display 3140. FIG. 3B shows the tablet computer 3100 coupled or removably attached to the protective case 3200.

FIG. 3B also shows that the tablet computer protective case 3200 may comprise a plurality of sensor electrode leads including a first electrode lead 3210 and a second electrode lead 3220. As shown in FIGS. 3B and 3C, the first and second electrode leads 3210 and 3220 may be disposed opposite one another over the edges 3120 of the tablet computer 3100. Other alternate placements are also contemplated. For example, FIG. 3D shows the first and second electrode leads 3210 and 3220 disposed on the back face 3130 of the protective case 3200. Also, the plurality of electrode leads may further comprise a third electrode lead 3230 disposed on the back face 3130 of the protective case 3200 as shown by FIG. 3E.

The system 3000 may be used in a similar manner as system 2000 as described above to measure physiological signals. For example, the plurality of electrode leads of the system 3000 may be contacted with the user US to measure one or more of a Lead I, a Lead II, or a Lead III ECG. As shown in FIG. 3F, a user US may normally operate the system 3000 and the tablet computer 3100 while the first electrode lead 3210 contacts the right arm RA of the user, the second electrode lead 3220 contacts the left arm LA of the user, and the third electrode lead 3230 (not shown) contacts the left leg of the user. While FIG. 3F shows that the first application 1170 for managing the detected physiological parameter(s) is active on the tablet computer 3100, it is also contemplated that the second application 1180 is instead active and manipulated by the user US while the first application 1170 and the protective case 3200 senses and detects the physiological parameter(s).

Other computing device accessories for concurrently measuring the various physiological parameter(s) of the user US while the computing device is in normal use are also contemplated.

Figure 4A:
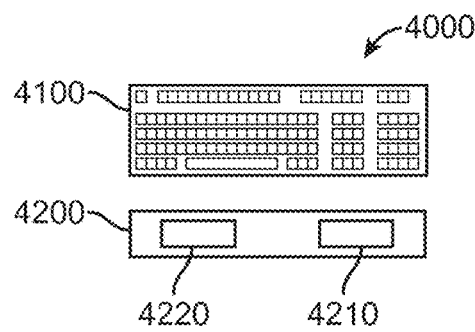
FIGS. 4A-4C show a biometric or physiological parameter measurement and monitoring system comprising a keyboard of a computing device and a keyboard accessory, in accordance with many embodiments.
Figure 4B:
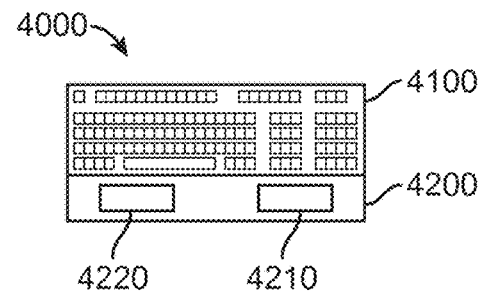
Figure 4C:
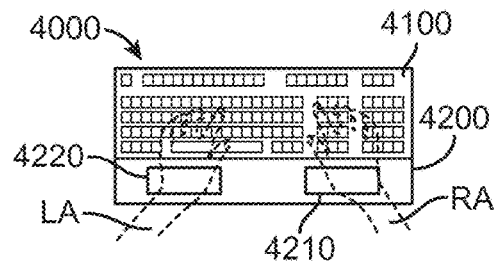

FIGS. 4A-4C show a biometric or physiological parameter measurement and monitoring system 4000 comprising a keyboard 4100 of a computing device 1100 and a keyboard accessory 4200 which may comprise a keyboard wrist rest. The keyboard 4100 may be removably coupled to the keyboard accessory 4100 (compare FIG. 4A with FIG. 4B.) The keyboard accessory 4200 comprises a physiological parameter sensor such as a plurality of electrode leads such as a first electrode lead 4210 and a second electrode lead 4220. As shown in FIG. 4C, the first electrode lead 4210 may contact a right arm RA of the user and the second electrode lead 4220 may contact a left arm LA of the user to detect a Lead I ECG while the user US normally operates the computing device 1100 through the keyboard 4100.

Figure 5A:
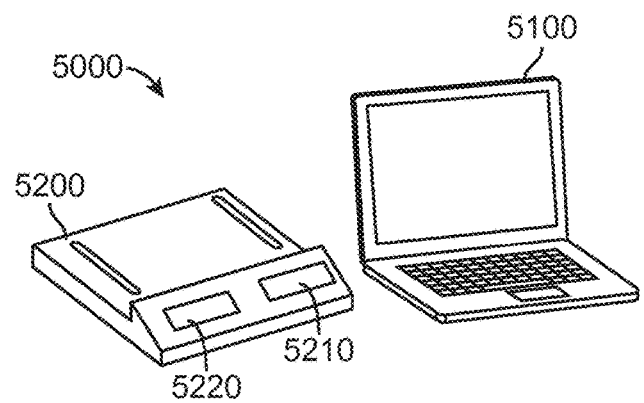
FIGS. 5A-5C show a biometric or physiological parameter measurement and monitoring system comprising a laptop or palmtop computer and a sensor accessory, in accordance with many embodiments.
Figure 5B:
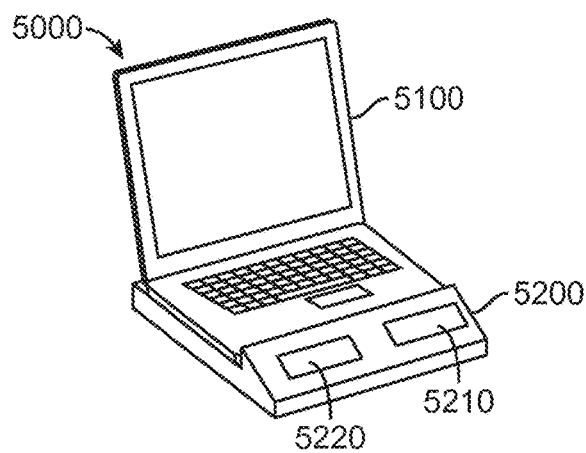
Figure 5C:
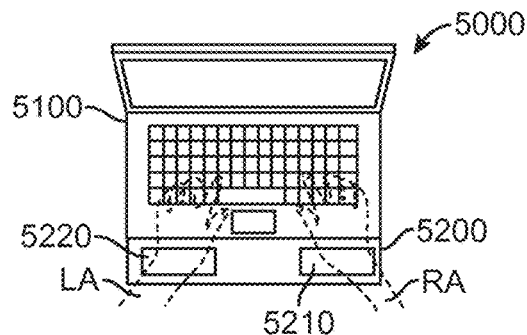

FIGS. 5A-5C show a biometric or physiological parameter measurement and monitoring system 5000 comprising a laptop or palmtop computer 5100 and a sensor accessory 5200. The computer 5100 may be removably coupled to the sensor accessory 5100 (compare FIG. 5A with FIG. 5B.) The sensor accessory 5200 comprises a physiological parameter sensor such as a plurality of electrode leads such as a first electrode lead 5210 and a second electrode lead 5220. As shown in FIG. 5C, the first electrode lead 5210 may contact a right arm RA of the user and the second electrode lead 5220 may contact a left arm LA of the user to detect a Lead I ECG while the user US normally operates the computer 5100.

Further sensor accessories for coupling with everyday use devices are also contemplated. For example, embodiments of the present disclosure may provide a sensor accessory for a handle bar of a bicycle, a motorcycle, an exercise machine such as a treadmill or an elliptical machine or a weight-lifting machine, a seat, a chair, a set of eyeglasses, clothing, etc. As another example, the sensor system described herein may be in the form of a watch, a wristlet, a wristband, or an accessory to such devices. ECG sensing watches and wristlets are described in co-owned U.S. Provisional Patent Application No. 61/872,555, filed on Aug. 30, 2013 and entitled "Ultrasonic Transmission of Signals from an ECG Sensing Wristlet." The sensor accessory may detect and measure one or more physiological parameters and communicate the measurement to a computing device associated with the everyday use device or to another computing device.

Figure 6:
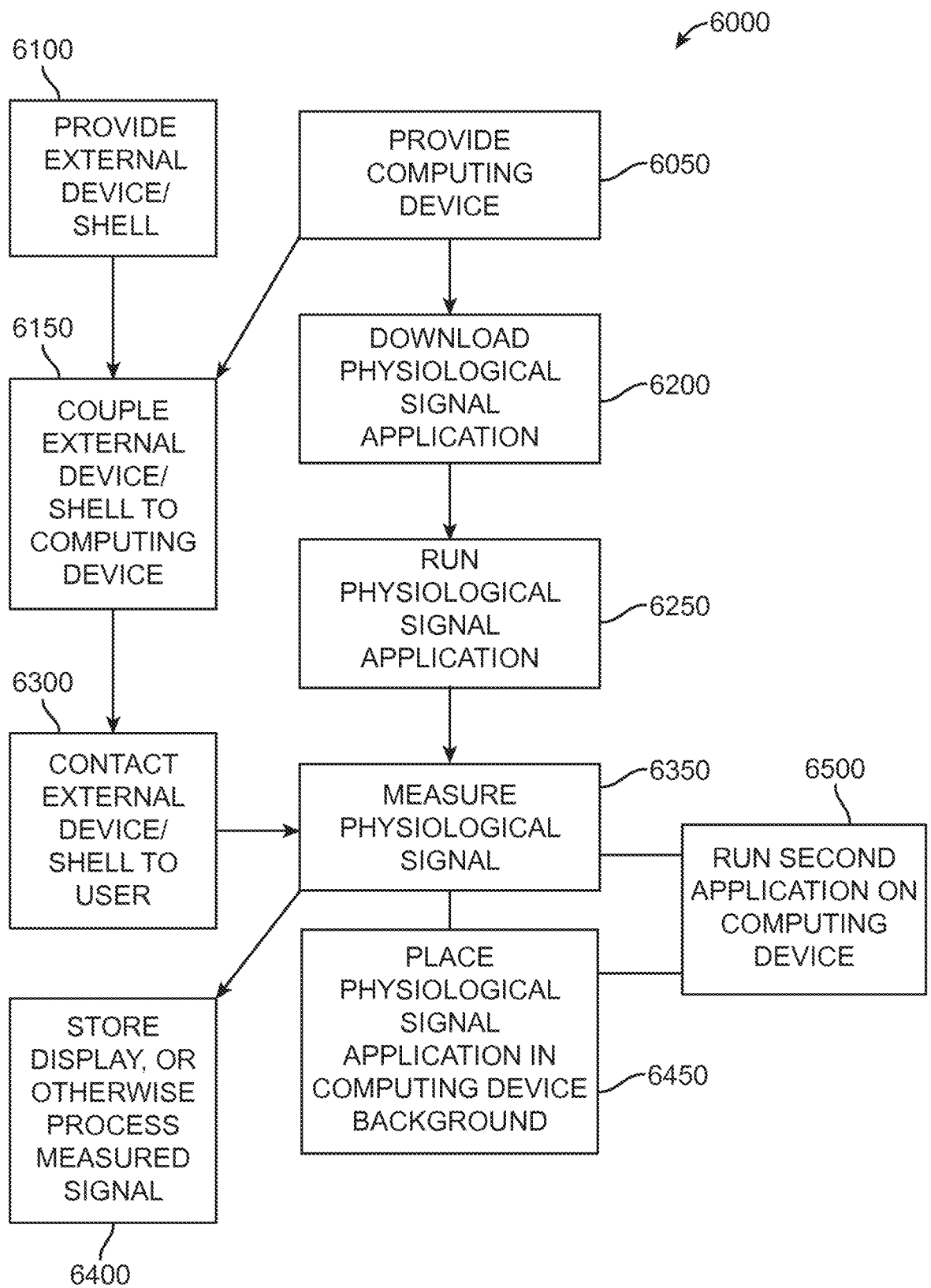
FIG. 6 shows a method for biometric or physiological parameter measurement and monitoring, in accordance with many embodiments.
Figure 7:
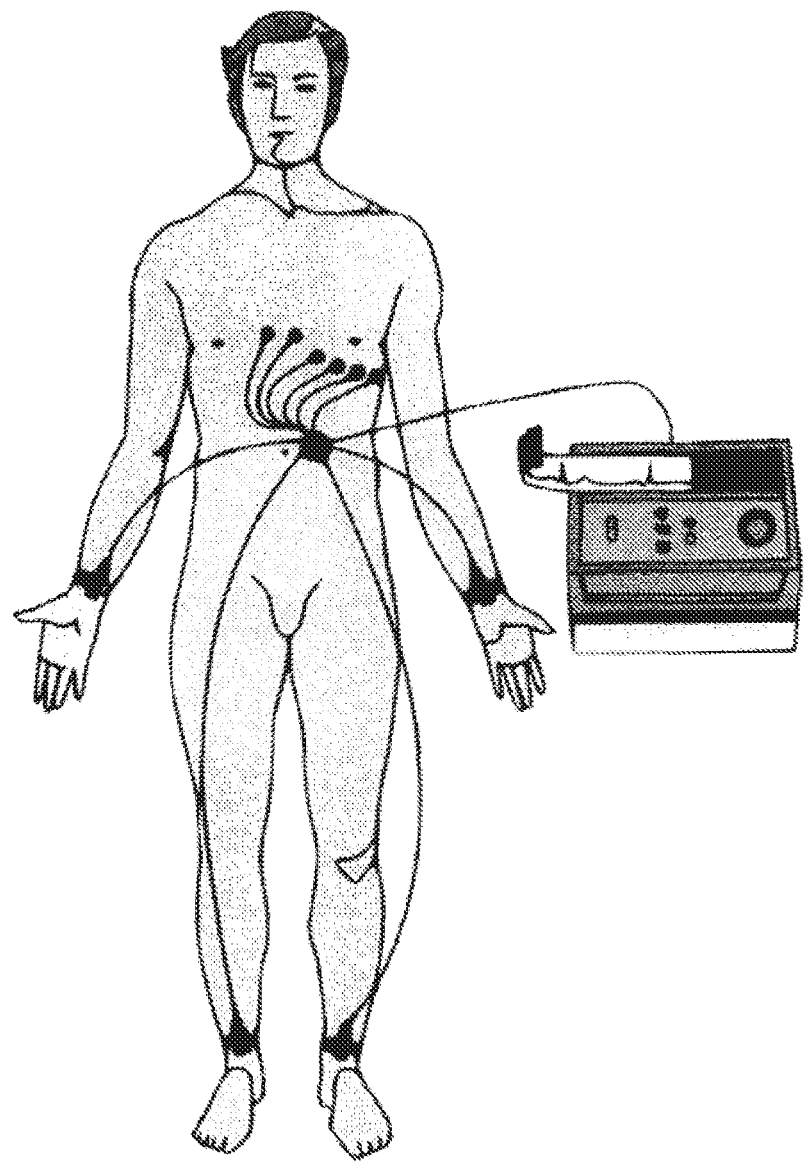
FIG. 7 is a pictorial representation of a body showing an example of the electrode placement for taking a standard 12-lead ECG.
Figure 8:
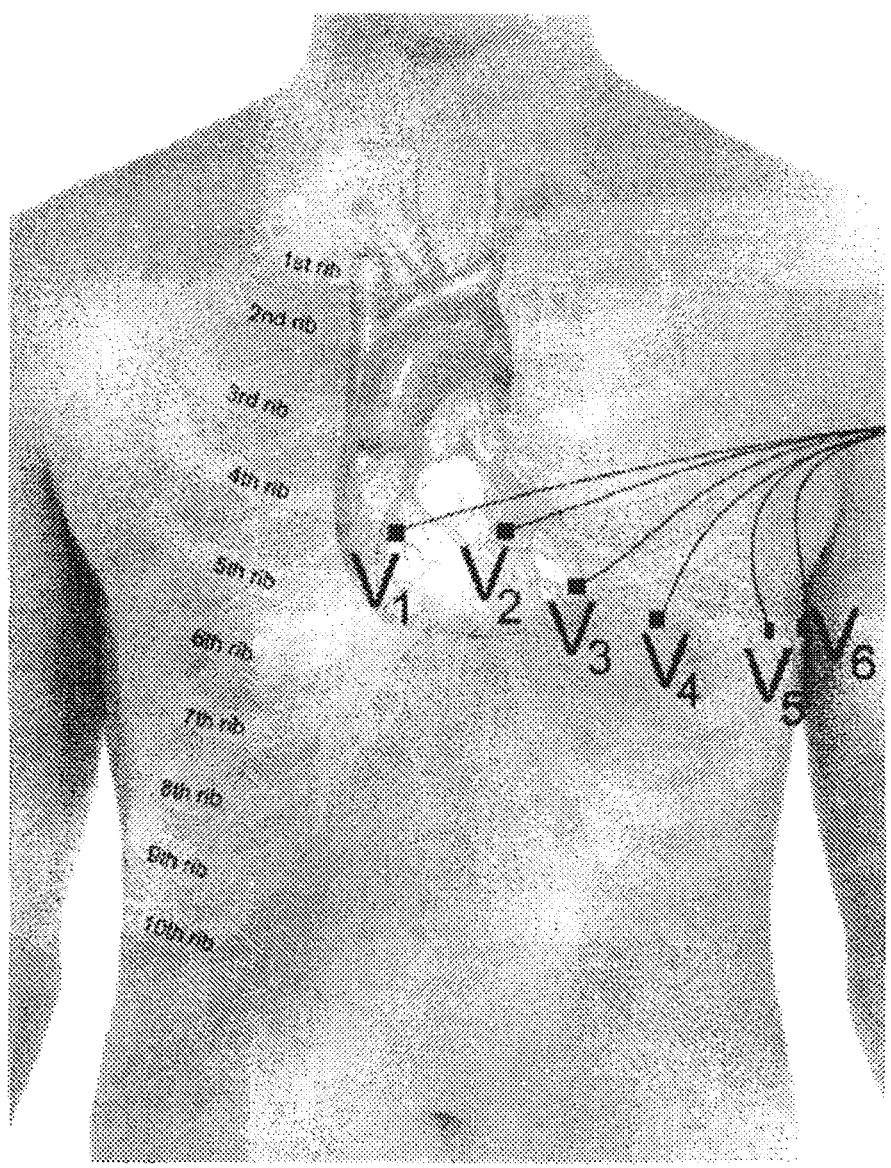
FIG. 8 is a pictorial representation of a chest showing an example of electrode placement on the chest for taking a 12-lead ECG (showing positioning for V6-V12)

FIG. 6 shows a method 6000 for biometric or physiological parameter measurement and monitoring. In a step 6050, a computing device, such as computing device 1100 described herein, may be provided. In a step 6100, an external device or shell for the computing device, such as external device 1200 described herein, may be provided. In a step 6150, the external device or shell may be coupled to the computing device. See, for example, system 2000 described herein (FIGS. 2A-2D), system 3000 described herein (FIGS. 3A-3B), system 4000 described herein (FIGS. 4A-4C), and system 5000 described herein (FIGS. 5A-5C). In a step 6200, a physiological signal or parameter measurement and monitoring application may be downloaded onto the computing device. The application may comprise the first application 1170 described above and may be downloaded from an application distribution platform through the Internet as described herein. In a step 6250, the application may be run on the computing device. In a step 6300, the external device or shell coupled to the computing device may be contacted with the user to measure the physiological parameter(s). In a step 6350, the physiological signal(s) or parameter(s) may be measured. In a step 6400, the physiological signal(s) or parameter(s) may be stored, displayed, or otherwise processed. In a step 6450, the physiological signal or parameter measurement and monitoring application may be placed in the background of the computing device. In a step 6500, a second application may be run on the computing device while the physiological signal or parameter measurement and monitoring application performs its work in the background.

Although the above steps show method 6000 of biometric or physiological parameter measurement and monitoring, a person of ordinary skill in the art will recognize many variations based on the teaching described herein. The steps may be completed in a different order. Steps may be added or omitted. Some of the steps may comprise sub-steps. Many of the steps may be repeated as often as beneficial.

One or more of the steps of the method 6000 may be performed with circuitry as described herein, for example, one or more of a processor or logic circuitry of the computing device or an accessory thereof. The processor or logic circuitry may be programmed to provide one or more of the steps of the method 6000, and the program may comprise program instructions stored on a computer readable memory or programmed steps of the logic circuitry.

Three Electrode ECG Device Cover

In general, described herein are apparatuses and methods for generating an electrocardiogram (ECG) from a patient including hand-held wireless telecommunications device cases having three electrodes on an outer surface of the case, and methods of using them. These apparatuses and methods may permit the user to take up to six leads (e.g., lead I, lead II, lead, aVR, aVL, and aVF) using a single hand-held device, which is easily held by the patient against his or her leg while simultaneously observing the display of the device. In particular, the device may be used in conjunction with a mobile telecommunications device (e.g., smartphone).

In general, the apparatuses described herein (including devices and systems) may include three electrodes, and are configured for use with a wireless telecommunications device. The wireless telecommunications device may be any appropriate telecommunications device, including smartphones (e.g., iPhone™, Android™, etc.), tablet (iPad™, etc.), laptop, PDA, etc. The apparatus may be configured as a case and/or attachment to the mobile telecommunications device. The apparatus may communicate information wirelessly to the mobile telecommunications device. In some variations, the systems described herein send information to a mobile telecommunications device that has been configured (e.g., by operating a program, applications ("app"), or the like) to receive and analyze information from the apparatus.

Thus, in general, the apparatuses described herein may include a housing configured as a case or otherwise. The housing generally includes an outer surface on which the three (or in some cases more) electrodes are arranged. In variations in which the housing is configured as a case to hold the mobile telecommunications device, the case may have an outer back surface and at least two outer side surfaces perpendicular to the back surface, and a front region through which a screen of the telecommunications device held in the case may be viewed.

For example, FIGS. 9A to 9D illustrate one variation of a housing configured as a case for a smartphone. In this example, the case 300 is shown with a mobile telecommunications device (smartphone) 301 hosed within the case. The case 300 includes a back (shown in FIG. 9C) and sides (shown in FIGS. 9B and 9D). The front of the case 300 in this example has an opening 301 through which the front (including the screen) of the smartphone may be viewed and/or touched. The case may also include openings on the sides (e.g., 9B) for phone controls.

In general, the housing also includes at least (and in some variations, exactly) three electrodes, one each for contacting the right hand, left hand, and leg of a subject. For example, a first electrode may be configured to be held against the patient's leg. A second and third electrode may also be configured and arranged on the housing so that the patient may touch the second electrode with the right hand and the third electrode with the left hand while holding the first electrode against their leg. The positions, shapes, and/or sizes of the electrodes may be configured so that the patient's hands don't contact more than one electrode, and the patient's leg also does not contact more than one electrode on the housing when measuring an ECG. For example, the first electrode may be located on a side or side edge (on the back side edge) or both of the housing while the second and third electrodes are located on the back and all electrodes are separated from each other sufficiently far so as to avoid the leg of a hand making contact with more than one electrode. Thus the left hand may contact a single electrode, the right hand may contact another electrode and the leg may contact the first (leg) electrode all on the same housing.

Figure 9D:
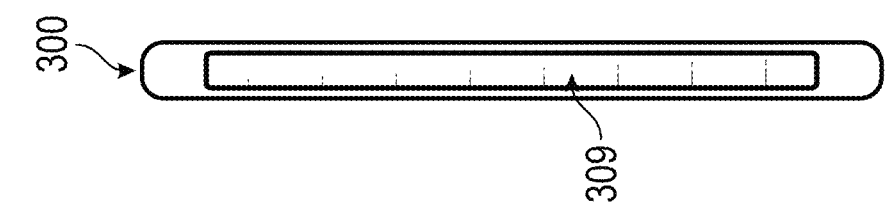
FIGS. 9B, 9C and 9D show left side, back, and right side views, respectively, of the apparatus of FIG. 9A.
Figure 9C:
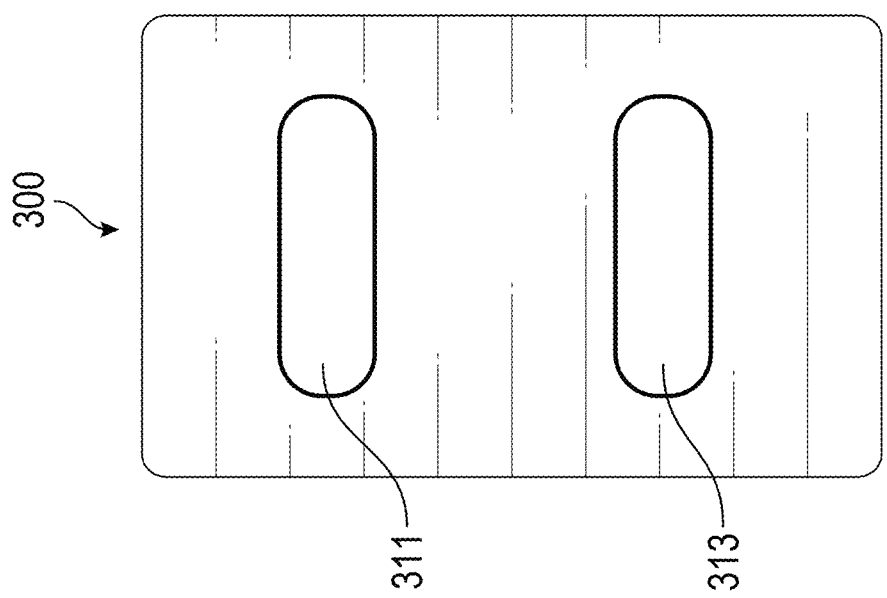
Figure 9B:
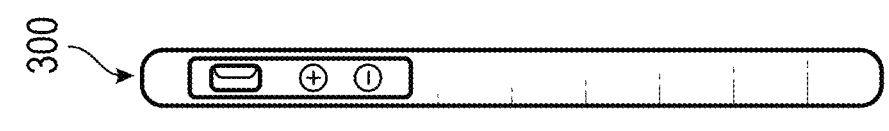
Figure 9A:
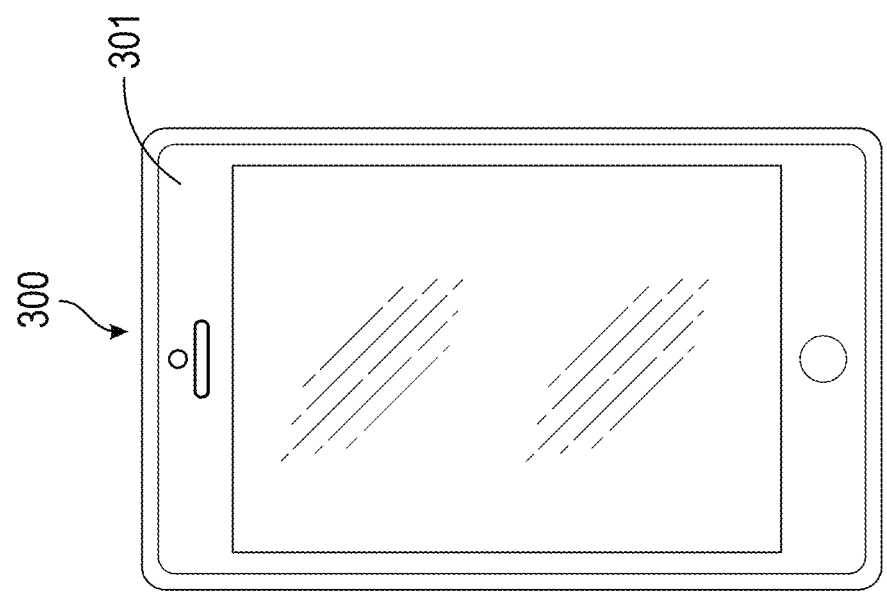
FIG. 9A shows a front view of one variation of an apparatus as described herein (where in this example, a wireless mobile telecommunications device is shown inserted into the apparatus, which is configured as a case)

In FIG. 9A, the electrodes are arranged so that the first electrode 309 is on one of the outer side surfaces of the case. Placement of the first electrode on the side of the case may allow the first electrode to be easily held against the subject's leg while the patient holds the case so that that their first (e.g., left) hand contacts the second electrode and their other (e.g., right) hand contacts the second electrodes.

In general, in any of the apparatuses described herein the electrodes may be on the outer surface of the housing; in some variations the housing may be configured (or may include additional elements) to protect the one or more electrodes from making contact with a surface such as a table or the like, when the apparatus is set down on the surface. In the event that the apparatus is placed down onto a conductive surface (e.g., a metal table), the housing or additional features may prevent the outer surface of the electrodes from contacting the surface. For example, the electrodes on the outer surface of the housing may be recessed relative to at least a portion of the outer back surface so that the outer contact surfaces of the first, second and/or third electrodes do not contact a table surface when the case is placed on the table surface with the outer back surface facing the table surface.

As mentioned above, placement of the first electrode on a side surface may allow the apparatus to be used to take measurement from the leg while viewing a surface (e.g., the screen) of a telecommunications device within the case.

In FIG. 9A-9D, the case includes just three electrodes, 309, 311, and 313, and the first (leg) electrode is positioned on a side outer surface of the housing. The side (first) electrode is configured to extend along most of the length of the side of the housing. The second 311 and third 313 electrodes are positioned nearer to the center of the back outer surface of the housing. As is apparent in the side-profile views of FIG. 9B and FIG. 9D, the housing protects the second and third electrodes because the height of the electrodes is lower than the outer surface of the rest of the case.

FIG. 10A-10D illustrates another variation of a case having three electrodes. However, in this example, the first (leg) electrode 413 does not have an outer surface that is lower than the outer surface of the case, but instead the third electrode projects from the outer surface as is shown in FIG. 10D. The case shown in otherwise similar to the variation shown in FIGS. 9A-9D, although these figures are shown without the mobile telecommunications device (e.g., smartphone) within the case.

Figure 11C:
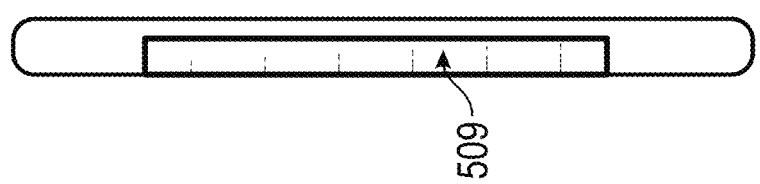
FIGS. 11A-11C illustrate another variation of an apparatus as described herein from the left side, back, and right side views, respectively (in this example, the leg (first) electrode is on the edge between the back surface and the left side of the case)
Figure 11B:
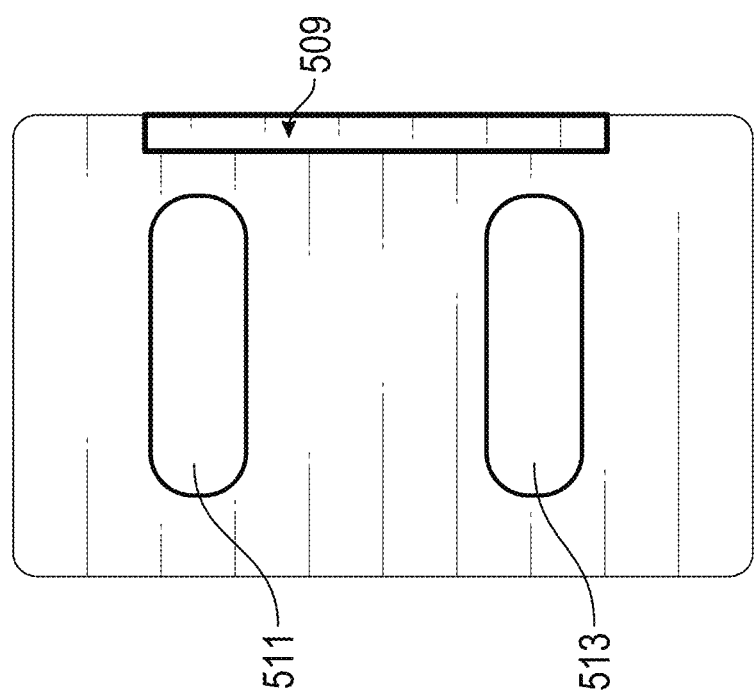
Figure 11A:

In some variations, the leg electrode (electrode 1) 509 extends from the side surface to the back surface where the other electrodes 511, 513 are located, as shown in FIGS. 11A-11C.

Figure 12C:
FIGS. 12A-12C illustrate another variation of an apparatus as described herein from the left side, back, and right side views, respectively (in this example, the leg (first) electrode is on the back surface, adjacent to the left side)
Figure 12B:
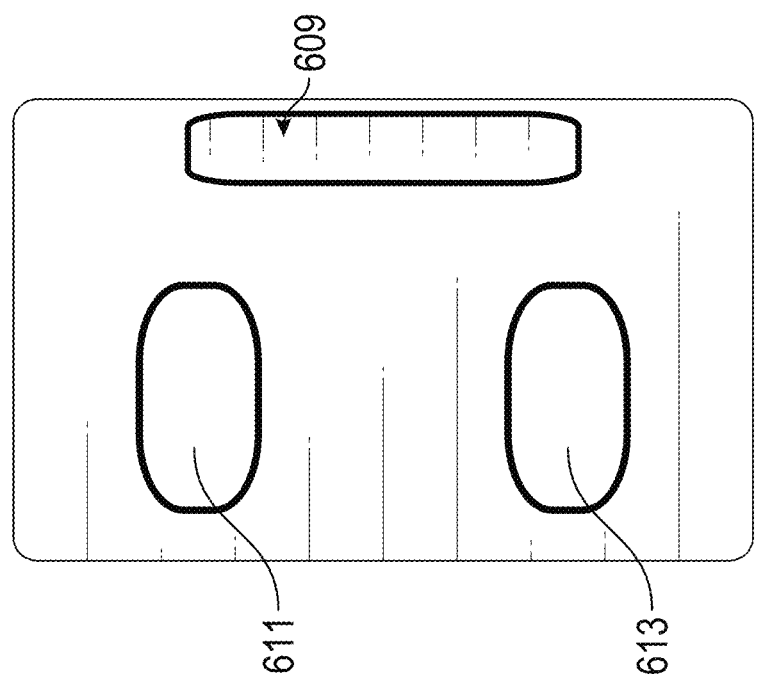
Figure 12A:

Alternatively, in some variations, the leg electrode is positioned near the edge of the case (e.g., near the side edge) as shown in FIG. 12C. In general, the leg electrode may be adjacent to one of the side surfaces. The electrode may be immediately adjacent to the side and may contact the edge. FIGS. 12A-12C illustrate a case configured so that the first electrode 613 is adjacent to the side of the case; the second 609 and third 611 electrodes may be shifted away from the first electrode to prevent inadvertent contact by the subject's hands and the leg electrode (or the other electrode).

Figure 13C:
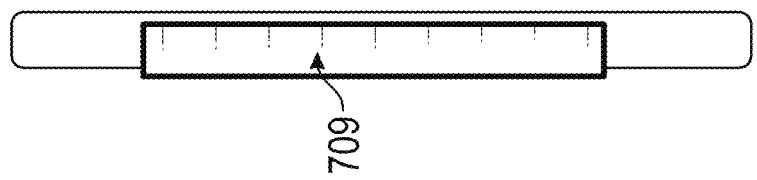
FIGS. 13A-13C illustrate another variation of an apparatus as described herein from the left side, back, and right side views, respectively (in this example, the leg (first) electrode is on the edge between the back surface and the left side of the case)
Figure 13B:
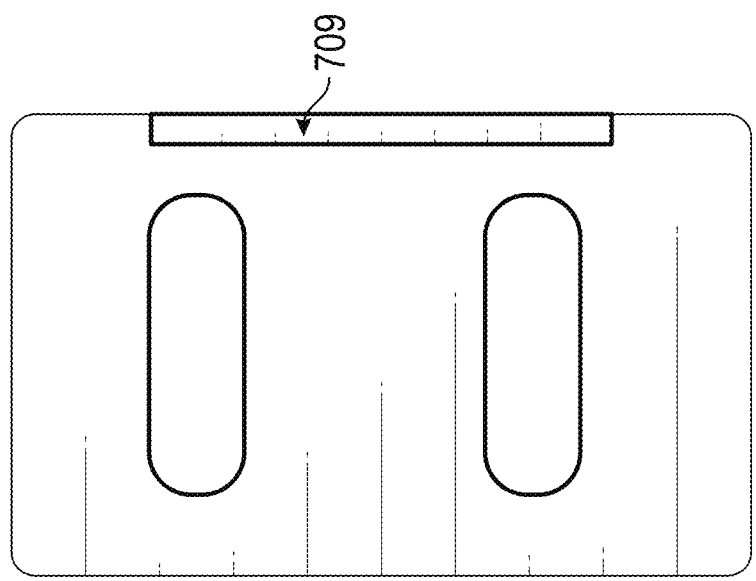
Figure 13A:

FIGS. 13A-13C illustrate another variation of a case having a first electrode 709 that extends from the back surface and around the side edge to the side surface, as shown. In this example, the second and third electrodes are recessed relative to the outer surface of the back of the case, while the first electrode extends from the outer surface. This may make it easier to contact the leg and hold the case at an angle.

In some variations the housing may be configured to hold an electrode unit that fits within an opening in the outer back surface of the case; the electrode unit includes the second and third (and in some variations the first) electrodes and may also include circuitry for controlling/receiving ECG recordings. For example, FIG. 14A-14C illustrates an apparatus configured as a case holding an electrode unit 805 including a second 811 and third 813 electrode to be touched by the patient's right and left hands, and a separate first electrode 809 on the side of the case. The electrode unit may extend proud of the case and may include an outer (non-electrode) surface that extends further from the outer surface of the case than the second and third electrodes, preventing the second and third electrodes from touching a table surface when the device is set down on the table.

Figure 15C:
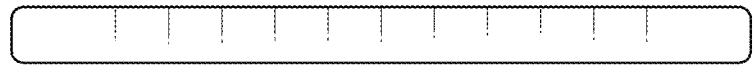
Figure 15B:
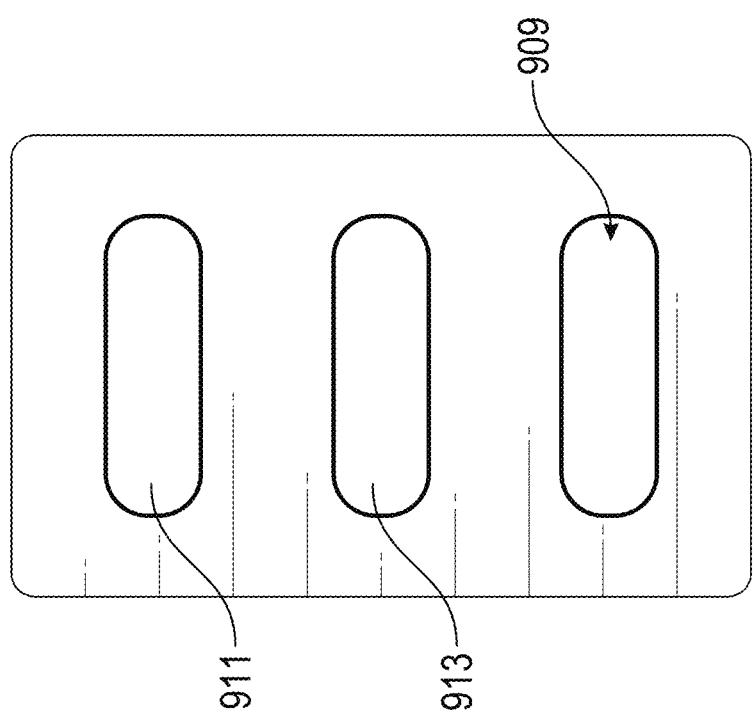
Figure 15A:

FIGS. 15A-15C illustrate another variation of a three-electrode housing in which all three electrodes (first electrode 909, second electrode 911 and third electrode 913) are arranged on the back surface of the case, as shown in FIG. 15.

Figure 16B:
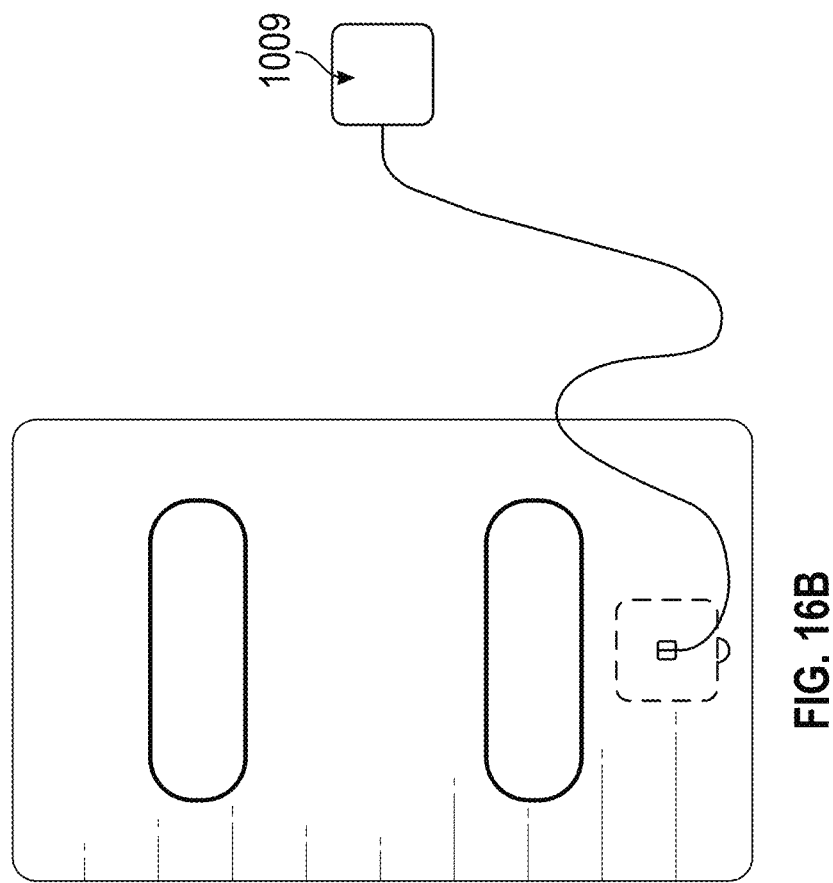
FIGS. 16A-16B illustrate another variation of an apparatus as described herein from the left side, back, and right side views, respectively (in this example, the leg (first) electrode is on a cord that is extendable from the body of the device to attach to the leg)
Figure 16A:
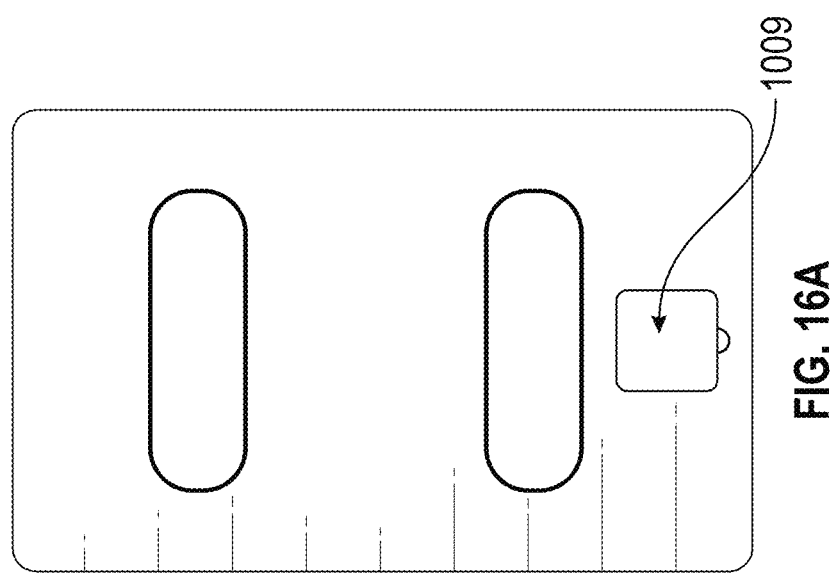

Although many of the variations described herein have all three electrodes integrated on the outer surface of the case, in some variations one or more of the electrodes may be configured to extend from the surface of the case. For example, in FIGS. 16A and 16B, an example of a device having a first electrode 1009 that may be extended from the housing on a wire is shown. When not in use, the wire may be retracted into the case and the electrode 1009 may be coupled to the case, in use, the electrode may be pulled from the case and may contact the patient's leg, so that the case and smartphone may be held and viewed by the patient. In any of these variations, the smartphone may provide visual feedback to the patient before or during the recording. For example, indicating that good electrical contact is being made, and/or showing traces of the ECGs taken by the system.

Figure 17:
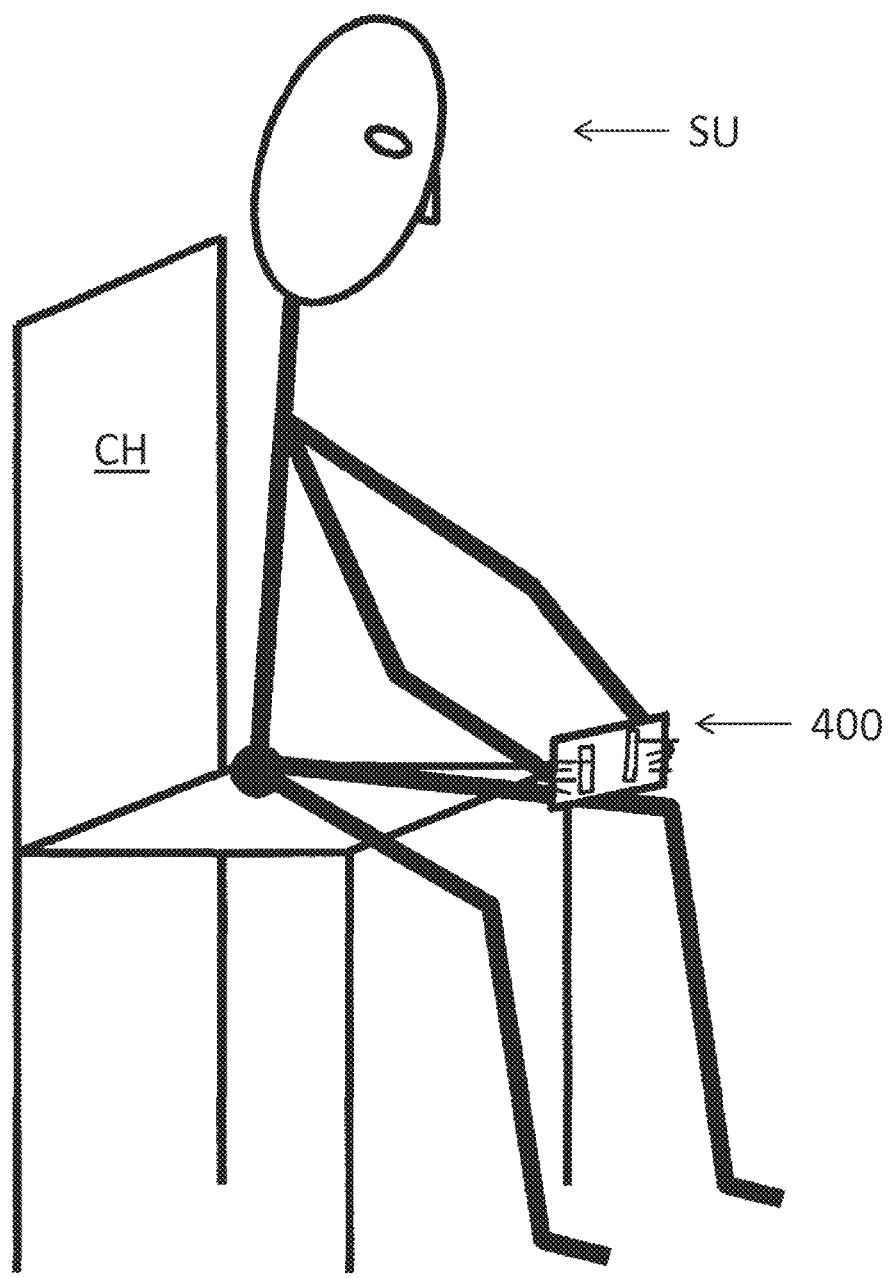
FIG. 17 illustrates the application of one variation of the apparatus for detecting ECG described herein, being held against a patient's leg so that a leg electrode contacts the leg while the patient's hand make contact with the left and right electrodes on the back of the apparatus, respectively.

For example, FIG. 17 illustrates a method of operating a device 400 having two hand (right hand, left hand) electrodes and a leg electrode. In this example, the subject SU is sitting in a chair CH and holds the apparatus 400, configured as a smartphone case holding a smartphone, with both hands so that each hand contacts just one electrode on the back of the case. The case is held against the subject's leg so that a leg electrode is pressed against the leg. The case and smartphone may then be used to record Lead I, Lead II, and Lead III, from which at least three additional leads may be determined, as discussed above. Specifically, the augmented leads, aVR, aVL, and aVF, may be determined.

ECG Sensing Wristlet

In general, also described herein are devices and systems for ultrasonically transmitting information (e.g., biological parameter information) from a wearable (e.g., wristlet) sensing device by ultrasonic transmission device to a telecommunications device that can then process and/or transmit the biological parameter information. In particular, the biological parameter may include an ECG signal. The wearable device typically includes an ultrasonic transducer witch may be part of an ultrasonic modem module/subsystem for encoding and transmitting information as an acoustic ultrasonic signal. In many of the variations described herein, these devices are configured as a wristlet to be worn by a subject.

As will be described in detail below, in some variations the ultrasonic signal (e.g., encoding an ECG) may be securely transmitted using an encryption key. Also described herein are systems, methods and device for easily pairing an ultrasonic transmission device to a telecommunications device using an encryption key. For example, in some variations the telecommunications device may read (e.g., take an image of) an encryption key that is displayed on the ultrasonic transmission device. This technique may be readily performed by taking an image of a mark containing the encryption key (e.g., bar code, QR code, etc.) with the telecommunications device and determining the encryption key based on the image. Executable logic running on the telecommunications device (e.g. decryption logic) may be configured to interpret and apply this encryption key.

For example, a system capable of ultrasonically transmitting digital biological parameter information may include a sensor for sensing a biological parameter (e.g., vital sign), a processor for configuring a representation of the biological parameter as a "digital" ultrasonic signal, an analog signal, or a hybrid digital/analog signal, and a transducer for transducing the ultrasonic signal so that it can be open-air transmitted to a telecommunications-capable device. The processor may part of, controlled by or in communication with a controller (e.g., a microcontroller). The telecommunications-capable device (telecommunications device) may include a receiver (audio receiver) able to receive an audio signal in the ultrasonic range, and a processor for converting the ultrasonic signal back into an electronic signal for further processing or transmission.

Figure 18:
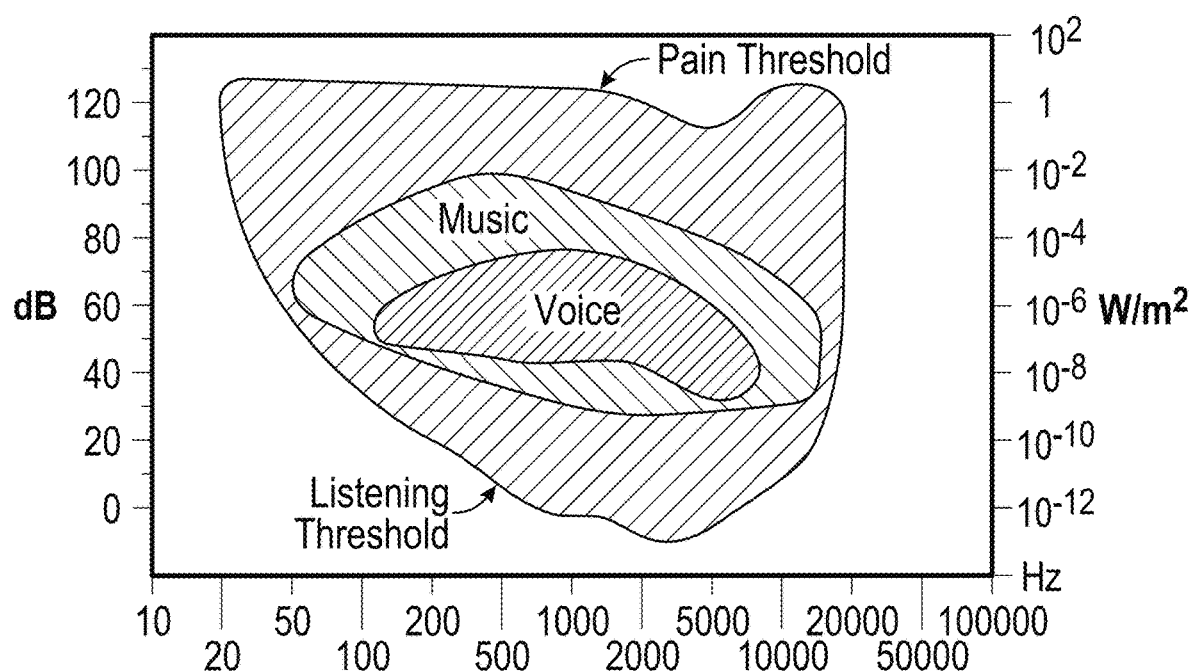
FIG. 18 is a pictorial representation of the human range and thresholds of hearing from http://en.labs.wikimedia.org/wiki/Acoustics.
Figure 19:
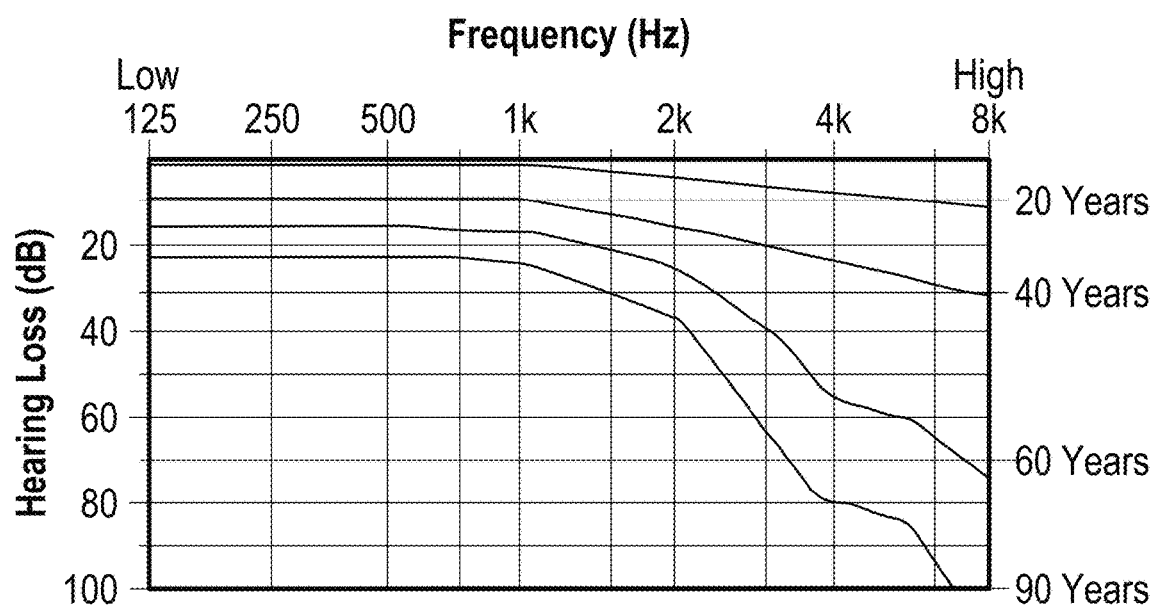
FIG. 19 is a pictorial representation of hearing loss with age from www.neuroreille.com/promenade/english/audiometry/audiometry.htm.

The human hearing range is often referred to as 20 Hz to 20 kHz, however maximum aural range in children, under ideal laboratory conditions, is actually as low as 12 Hz and rarely as high as 20 kHz. Further, as shown in FIG. 18, the threshold frequency, i.e. the minimum intensity detectable, rises rapidly to the pain threshold between 10 kHz to 20 kHz. Thus, sounds above about 16 kHz must be fairly intense to be heard. Almost immediately from birth, the threshold sound level for these higher frequencies increases. As shown in FIG. 19, an average 20 year old has lost about 10 dB in the 8 kHz range, while at age 90, the average person has lost over 100 dB at this frequency.

An example product using very high frequency sound is the Mosquito alarm, a controversial device emitting an intentionally annoying 17.4 kHz alarm and used to discourage younger people from loitering. Due to adult hearing loss at this frequency, it is typically heard only by people less than 25 years of age. Similarly, students make use of the adult hearing loss by using "mosquito" ringtones in the 15-17 kHz on their cell phones during school. The students can hear the "mosquito" ringtones while their adult teachers cannot. The term "ultrasonic" typically means above the range perceived by humans. However, as demonstrated, the upper limit of hearing frequency varies with individuals and with age generally. Because of the differences in this upper limit, the term "ultrasonic" is defined herein and in the appending claims may refer to sound frequencies of 16 kHz or greater (e.g., greater than about 17 kHz, greater than 18 kHz, etc.).

Figure 20:
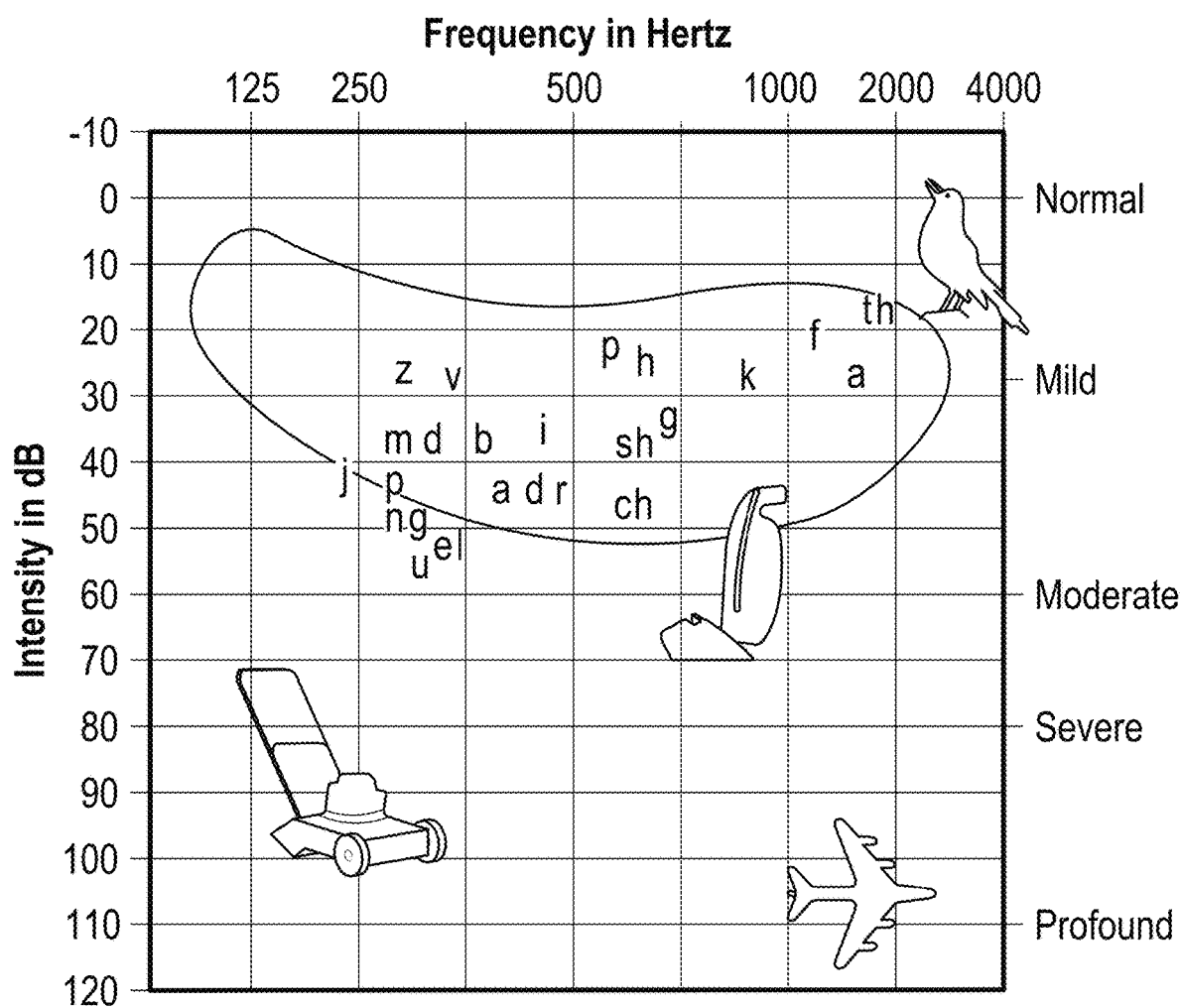
FIG. 20 is an audiogram illustrating the intensity and frequency of common sounds from www.hearinglossky.org/hlasurvivall.html.

Interestingly, however, there is very little ambient sound or noise above about 10 kHz. Referring to FIG. 20, most everyday sounds occur at frequencies below about 4 kHz. Thus, use of signals in the ultrasonic range is not only silent to those around, but also provides a very desirable signal to noise ratio (SNR).

Acoustic engineers safely assume that any frequency above about 20 kHz will have no effect on the perceived sound and may filter everything above this range. Sounds below 20 kHz but still in the ultrasonic range are of little concern, and standard sampling procedures have been established accordingly. It is generally understood that sampling an analog signal, whether a radio signal or audible sound signal, requires a sampling frequency fs such that fs/2>f, wherein f is the sinusoid frequency. For this reason, sound systems are designed to sample the sound at the now standard sample rate of 44.1 kHz, set somewhat higher than the calculated Nyquist-Shannon sampling rate of 40 kHz for a 20 kHz sound upper limit. Actual demodulation of an FM narrow band signal in the ultrasonic range, using existing demodulation procedures, computers, telephones, cell phones, stereo sound systems, etc., would result in very poor reproduction of the original signal. This is unfortunate because, as discussed above, a carrier signal in the ultrasonic range would also have a very low signal to noise ratio due to the fact that there is very little natural "noise" at these higher frequencies.

The devices, methods and systems for measuring physiological signals (e.g., biological parameters) and transmitting digital information about those measurements wirelessly and soundlessly use ultrasonic signals having a much improved signal to noise ratio compared to traditional transtelephonic methods. Also provided are methods and algorithms to receive and demodulate the ultrasonic signals with excellent accuracy using existing computer and smart phone technology.

Figure 21A:
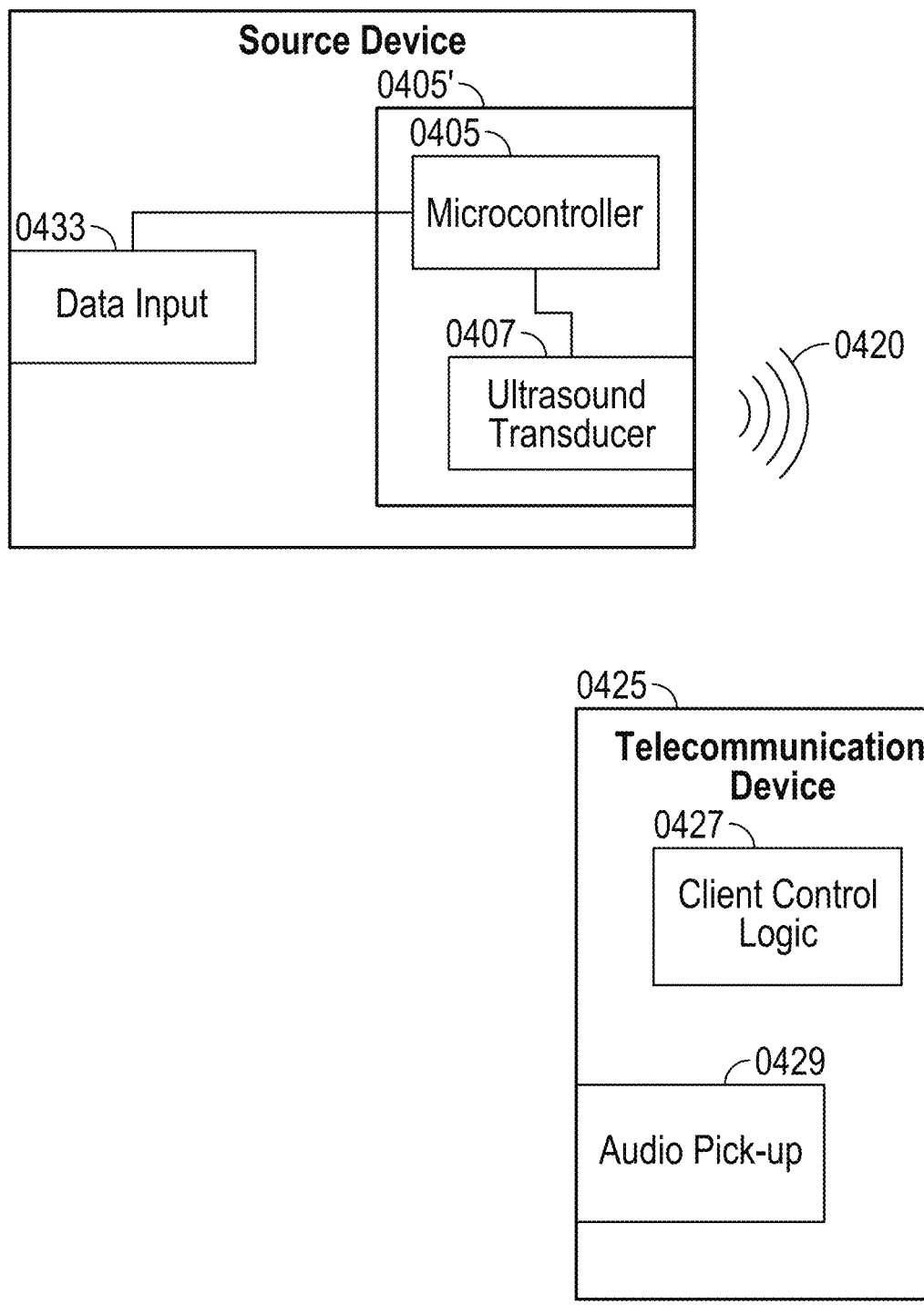
FIG. 21A is a schematic representation of a system that is configured to ultrasonically transmit digital data encoding one or more biological parameter to a telecommunications device such as a smartphone.

FIG. 21A shows a schematic overview of a system including a data input 0433 (e.g., providing any sort of information, including digital information and/or analog information) and a microcontroller 0405. In some variations, the microcontroller includes or is coupled with a processor for encoding a digital representation of a biological parameter, and this encoded signal may be converted to an ultrasound signal as descried in more detail below. For example, the encoded signal may be transmitted ultrasonically by an ultrasonic transducer 0407. In some variations, the microprocessor and the transducer may be coupled together or formed as part of the same component 0405', alternatively, the microprocessor may include a piezo/speaker element. This ultrasonic signal 0420 may then be received by a telecommunications device 0425, including an audio pick up (receiver) 0429. The telecommunications device 0425 may run client control logic 0427 preparing the telecommunications device to receive and translate the ultrasonic signal so that it can be processed, e.g., converting it back to an electronic signal, and interpreting which type of signal it is (e.g., pulse rate, temperature, etc.).

Figure 21B:
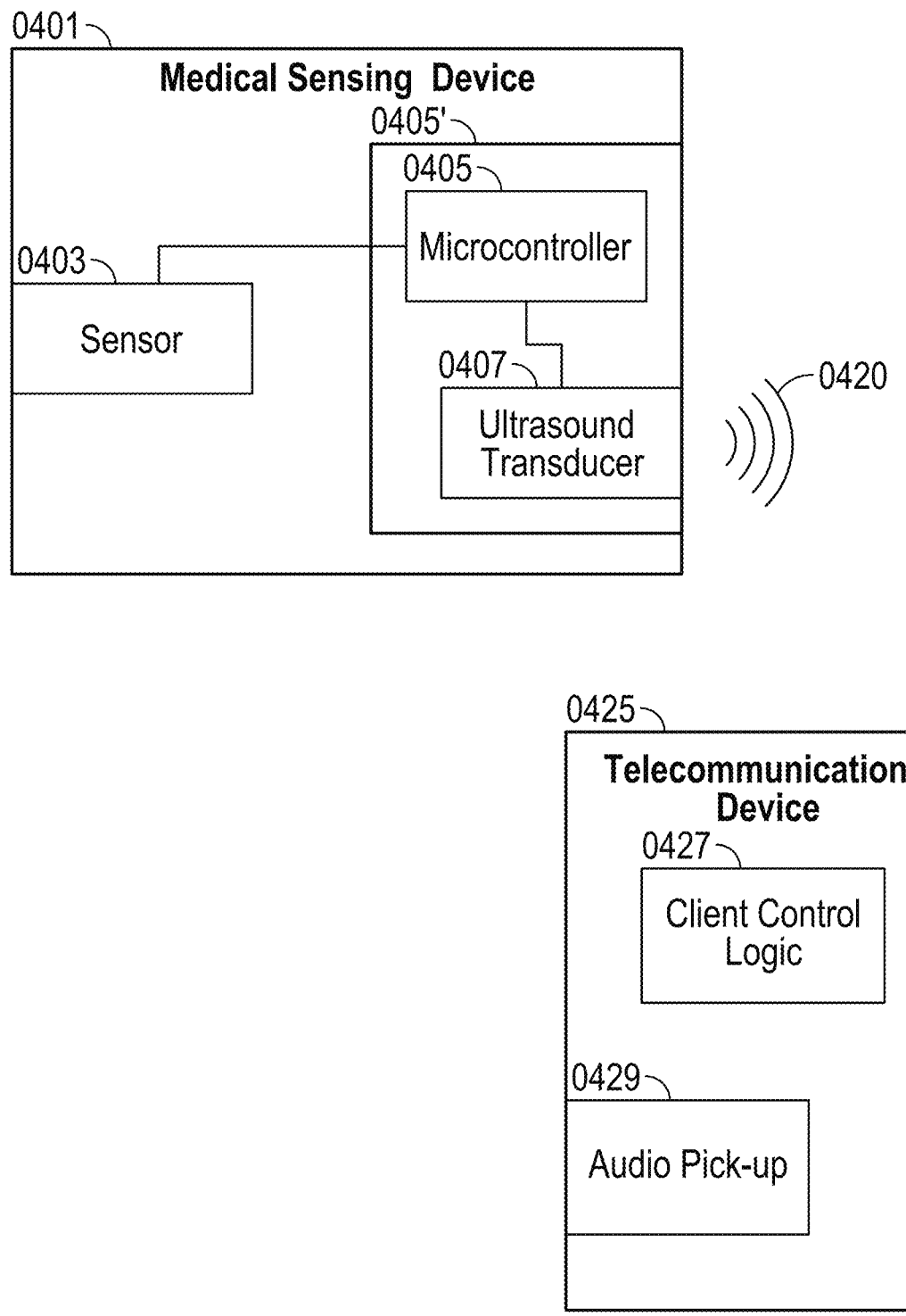
FIG. 21B is a schematic representation of a system including a medical sensing device that is configured to ultrasonically transmit data encoding one or more biological parameter to a telecommunications device such as a smartphone.

FIG. 21B shows a schematic overview of a system including a medical sensing device 0401 (e.g., a thermometer, blood glucose monitor, or the like) that has a sensor 0403 for detecting a biological parameter from a patient (e.g., temp, pulse rate, blood glucose, etc.) and a microcontroller 0405. The microcontroller may include or be coupled with a processor for encoding a digital representation of a biological parameter, and this encoded signal may be converted to an ultrasound signal as descried in more detail below. For example, the encoded signal may be transmitted ultrasonically by an ultrasonic transducer 0407. This ultrasonic signal 0420 may then be received by a telecommunications device 0425, including an audio pick up (receiver) 0429. The telecommunications device 0425 may run client control logic 0427 preparing the telecommunications device to receive and translate the ultrasonic signal so that it can be processed, e.g., converting it back to an electronic signal, and interpreting which type of signal it is (e.g., pulse rate, temperature, etc.).

Thus, medical sensing device 0401 in this example includes a sensor (or sensor assembly) configured to sense one or more physiological signals, such as temperature, pulse, pressure (e.g., blood pressure) or the like. The sensor may produce electrical signals representing the sensed physiological signals and these signals may be converted to a digital signal or signals that input to microcontroller or other associated components. This digital signal may typically be displayed on the device (not shown) and may also be electrically encoded as part of a digital signal that can then be ultrasonically encoded (e.g., by a technique such as frequency shift keying) to an ultrasonic sound and emitted from the device. The encoding of the signal may be performed by any appropriate circuitry, including, for example a microcontroller such as the MSP430 (e.g., the AFE4110 from Texas Instruments).

The center frequency may be selected from any appropriate ultrasonic frequency, including (but not limited to) 20 KHz. In some variations, the medical sensing devices described herein are configured as transmit only, so that data is transmitted to (but not received from) a telecommunications devices. In some variations, the medical sensing devices are configured to both send and receive ultrasonic (sound) frequency information (see, e.g., FIGS. 21C and 27). Further, in some variations, multiple channels (frequency channels) may be used.

In FIG. 21C, a schematic of a medical sensing device (e.g., a wristlet configured as an "ECG watch" to detect ECG signals and transmit them to a telecommunications device) is shown. In this example, the device (e.g., wristlet) includes a sensor 0403. In some variations, the sensor may include two or more electrodes to detect an ECG signal. The ultrasound transducer 407 may be configured as both an ultrasound transmitter and an ultrasound receiver. In some variation, the same transducer element (e.g., piezo) may be used for both. The telecommunications device 0425 may be configured to both receive (via an audio pickup 0429) and transmit (via an ultrasound transmitter 0433) ultrasound, such as ultrasound sent by the medical sensing device 0401.

In one embodiment, the ultrasonic signal has a center frequency in the range of from about 17 kHz to about 32 kHz. In another embodiment, the frequency modulated ultrasonic signal has a center frequency in the range of from about 18 kHz to about 24 kHz, or about 20 kHz to about 24 kHz.

Figure 22:
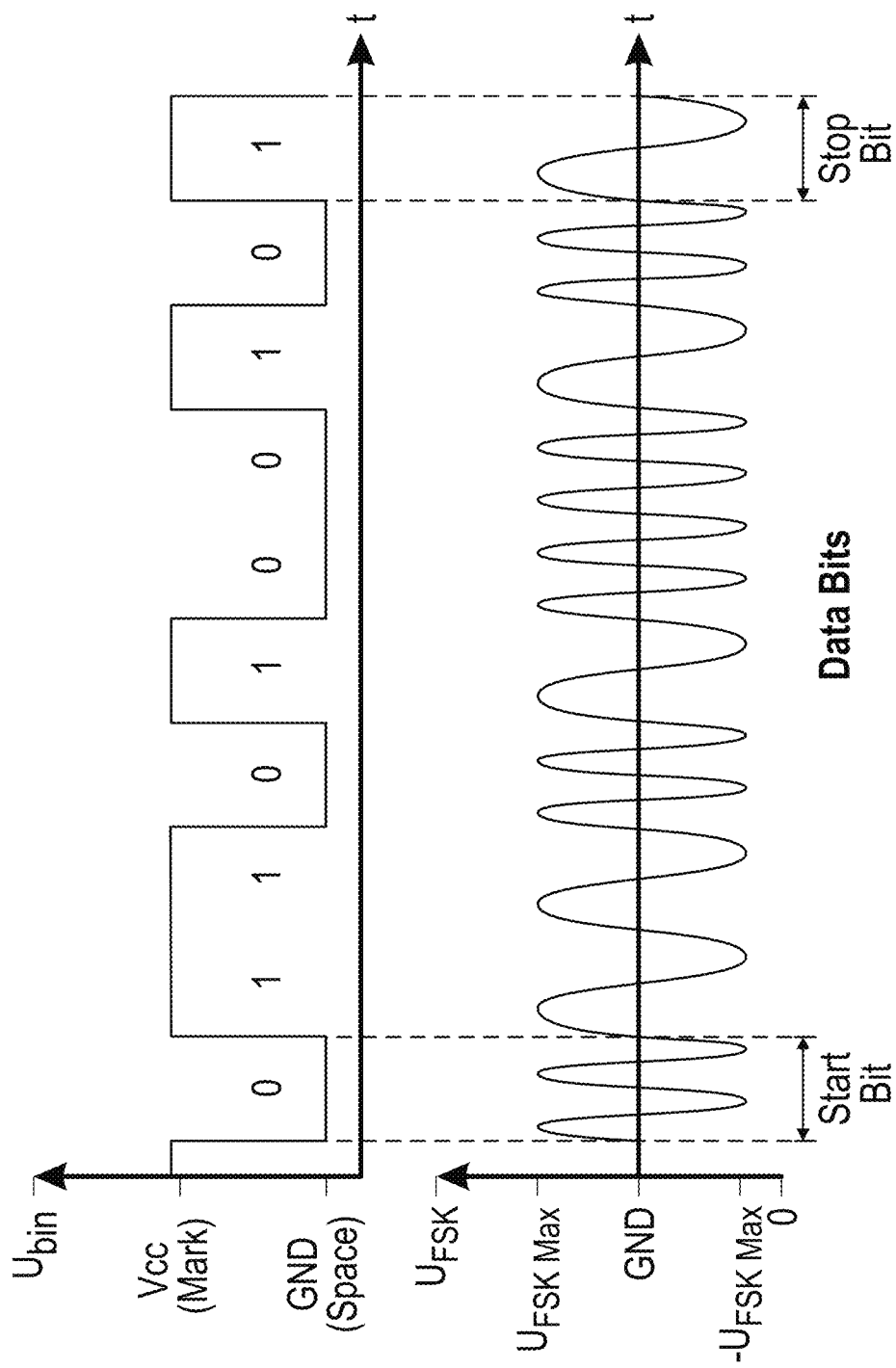
FIG. 22 shows one variation of a digital signal that has been encoded using frequency key-shifting in an ultrasound range, as described.
Figure 23:
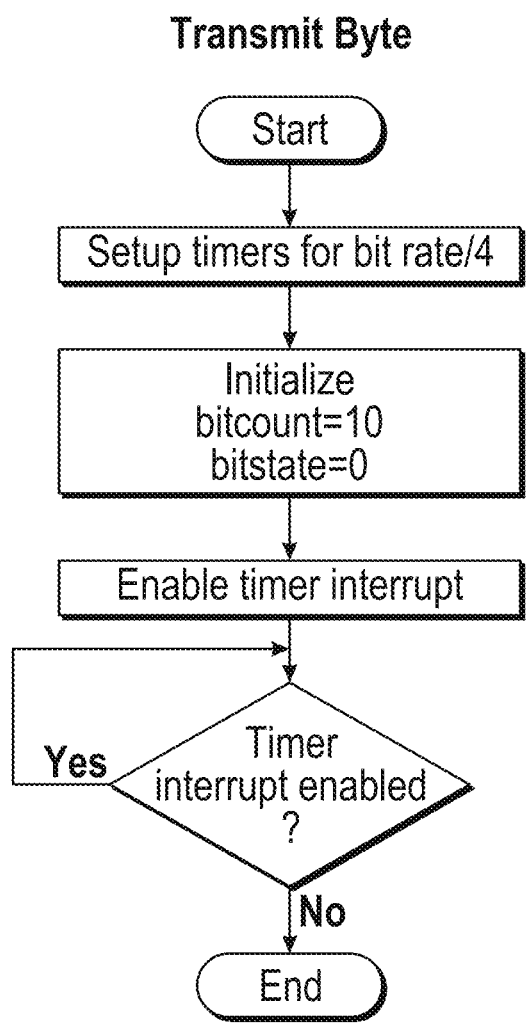
FIG. 23 is an exemplary flowchart illustrating one method of transmitting encoded data as an ultrasound signal.
Figure 24A:
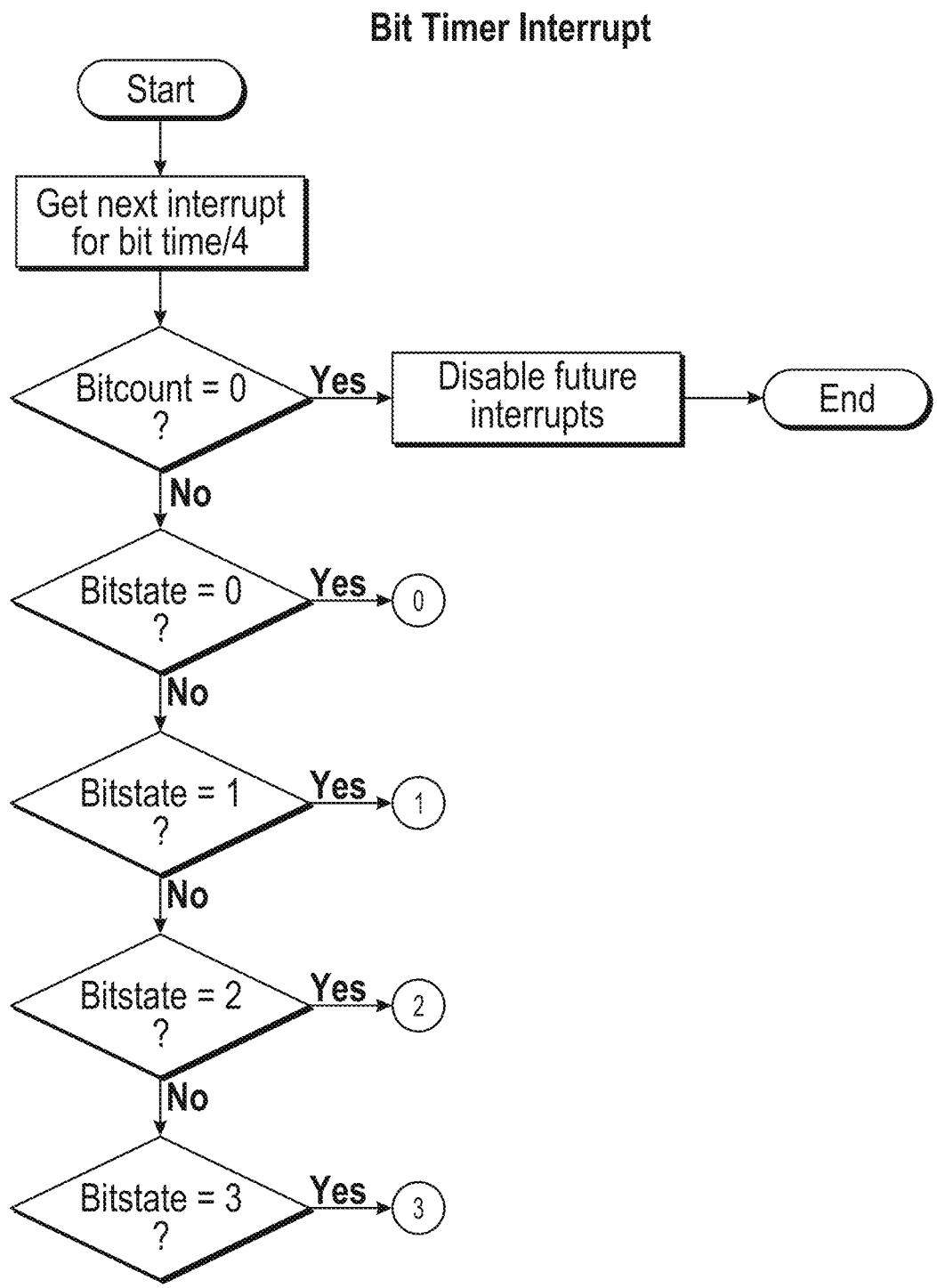
FIGS. 24A-24E are exemplary flowcharts of a method for transmitting a signal (e.g., packet transmission) as an ultrasound signal.
Figure 24B:
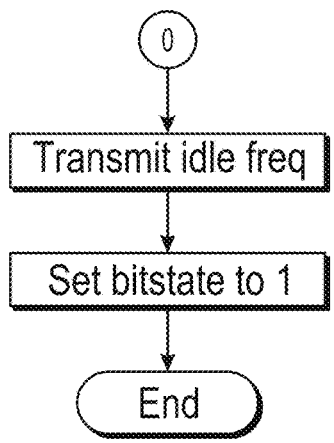
Figure 24C:
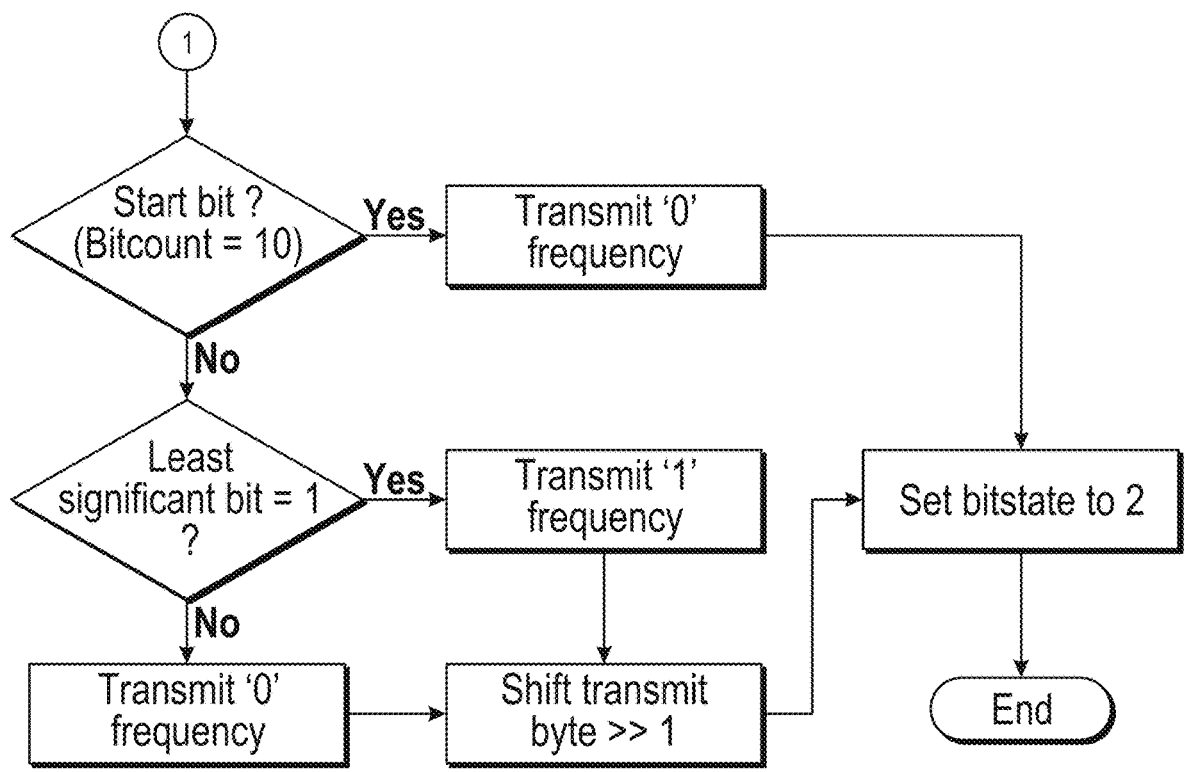
Figure 24D:
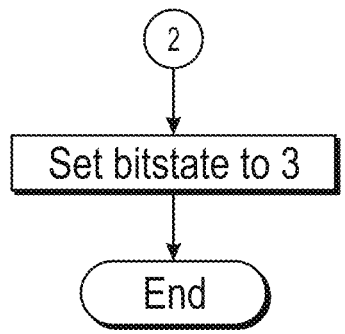
Figure 24E:
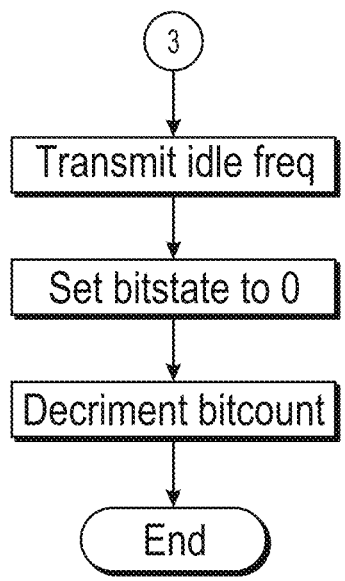

FIG. 22 shows one variation of a digital signal that has been encoded using key-shifting. In this variation the ultrasound signal is modulated at two different frequencies, one indicating high ("1") and one indicating low ("0"). For example, the frequencies for 0 and for 1 may be selected to be centered around 20 kHz (e.g., 19.5 kHz and 20.5 kHz).

In some variations, as mentioned above, the sensor encodes an ECG signal, however, in general, the sensor can include any suitable sensor operative to detect a physiological signal that a user desires to monitor. Multiple sensors may be included. Nonlimiting examples of such physiological signals include, but are not limited to, respiration, heart beat, heart rate, pulse oximetry, photoplethysmogram (PPG), temperature, etc. A respiration detector can be used. Heart beat and heart rate can be detected as well. For example, the oxygenation of a person's hemoglobin can be monitored indirectly in a noninvasive manner using a pulse oximetry sensor, rather than measuring directly from a blood sample. The sensor is placed on a thin part of the person's body, such as a fingertip or earlobe, and a light containing both red and infrared wavelengths is passed from one side to the other. The change in absorbance of each of the two wavelengths is measured and the difference used to estimate oxygen saturation of a person's blood and changes in blood volume in the skin. A photoplethysmogram (PPG) can then be obtained using the pulse oximeter sensor or with an optical sensor using a single light source. The PPG can be used to measure blood flow and heart rate. A digital representation of this data may then be used and passed on as described herein. In some variations (described in reference to FIGS. 26A and 26B, below), analog information may also be encoded and/or appended to digital information to form a hybrid of analog and digital information that is sent by the ultrasonic transmission device.

In some variations, a converter assembly converts the electrical (e.g., digital, analog, etc.) encoding of the biological parameter to an ultrasound signal that can be transmitted. In the embodiment shown in FIG. 21A, the converter assembly 0405' includes an ultrasound transducer 0407 for outputting ultrasonic signals. Nonlimiting examples of suitable ultrasonic transmitters (including transducers) include, but are not limited to, miniature speakers, piezoelectric buzzers, and the like.

Within the telecommunications device 0425, the ultrasonic signals can be received by, for example, a microphone 0429 in a device such as a smartphone, personal digital assistant (PDA), tablet personal computer, pocket personal computer, notebook computer, desktop computer, server computer, and the like.

The volume of the signal may be kept low to preserve power, although higher volumes are also possible because the sound is inaudible. For example, the volume of the signal can be further increased at the ultrasonic frequencies, without concern for "listeners" present, because they cannot hear it. Further, the signal may be encoded to prevent other device (not paired with the ultrasonic transmitting device) to receive and understand the signal.

As mentioned above, the telecommunications device may include a processor configured by client logic (e.g., software) for receiving and processing the ultrasound signals. For example, software on the smartphone can decode the ultrasound signal. Processing of the data may provide additional information related to the user including the type of the information (e.g., the nature of the biological parameter. For example: the signal may be encoded so that it contains (after a start identifier): 8 pulses indicating ECG data, 10 pulses indicating that it is a thermometer reading (e.g., 4 digits coming with last being after the decimal place); 12 pulses indicating it is a blood pressure reading (e.g., 3 digit systolic pressure, 3 digit diastolic pressure and 3 digit pulse rate); 14 pulses indicating that it is pulse oximeter data (e.g., 3 digit 02 sat and 3 digit pulse rate); 16 pulses indicating that it is glucometer data (e.g., 3 digit blood glucose level), etc. There may be a "separator" between the digits and an EOM (end of message) indicator. In practice, the signal may be sent several times so that a comparison may be performed between the received data for validation.

In one variation, the signal may be encoded so that (assuming 8 bit bytes, plus a start and stop bit): some number of AAs, or 55 s to allow sync, a byte that denotes a version number, a one byte length of the remainder of the packet, a one byte packet identifier (0x01 for BP, 0x02 for pulse ox, 0x03 for glucose, etc.), data, and an 8-bit CRC.

In some variations, the signal may also include a stretch of analog data (e.g., signal over time, signal over distance, etc.) for transmission with digital information, including information that formats or is extracted from (e.g., scales) the analog data. For example, a signal for transmission by ultrasound from an ultrasonic transmission device may include one or more digital portions and one or more analog portions. The digital portion may include information extracted from the analog signal such as the scaling (e.g., max and/or minimum values), duration, average, etc.). Analog, digital and analog and digital (hybrid) signals may be encoded, including encryption-encoded and/or may include error correction codes.

As mentioned, the signal can have a time and/or date stamp. In some variations, the devices or systems may be configured to take multiple measurements and send them to a telecommunications device as a batch or burst. For example, measurements might be made at times ti, t2 etc., and stored on the device (e.g., thermometer, glucometer, etc.) and transmitted to the telecommunications device (e.g., smartphone, tablet, etc.) ultrasonically at a later time (tn). The data may be processed by the telecommunications device and/or uploaded to an external server, etc. (e.g., the cloud).

The baud rate of the transmitted ultrasonic data may be selected to allow rapid transmission. For example, if a baud rate of about 300 baud is used, transmission may take less than a second, even for batched signals. In some variations, the baud rate is around 400.

As mentioned, raw signals from the sensors and derived information can be displayed and stored locally on the smartphone, as well as being transmitted to a web server over an internet connection. Software on the web server may provide a web browser interface for real-time or retrospective display of the signals and information received from the smartphone, and also includes further analysis and reporting.

Ultrasound signaling as used herein refers generally to the transmission of information, such as the magnitude of a biological parameter along with the origin of the biological parameter measurement, using ultrasonic signals. As mentioned, these ultrasonic signals may be encoded to allow transmission and processing. The encoded signal may then be transduced into the ultrasonic range by any appropriate method. For example, one or more frequencies may be used corresponding to various signal values, e.g. DTMF or DTMF frequency-shifted into ultrasonic frequencies. Another example of transducing the signal is to use amplitude shift keying. Another example is to use frequency shift keying. Another example is to use phase shift keying. In some embodiments, multifrequency signaling such as spread spectrum communications, or a multifrequency carrier signaling, may be used. An example of multifrequency carrier signaling is to designate a predetermined set of frequencies (for example, between 20 KHz and 22 KHz, or between 20 KHz and 24 KHz, or generally between a lower bound between 19 KHz and 20 KHz and an upper bound equal to or slightly below the Nyquist frequency for the sampling rate of an intended receiver) separated by an interval, such as an interval of between 40 Hz and 100 Hz, such as approximately 65 Hz, and for each such frequency, encode a "1" bit as the presence of a carrier signal, such as a sine wave at the frequency, and a "0" bit as the absence of such a signal. A receiver of such a multifrequency signal may then perform Fast Fourier Transforms or related techniques known in the art to identify whether carriers are available at each relevant frequency, and deduce a set of bits, encoding a number, thereby. In some embodiments of multifrequency carrier signaling, for example when a signal is insufficiently unambiguous, multiple samples may be taken over time and averaged, then the average signal may be processed as described above. In some embodiments of multifrequency carrier signaling, a Viterbi decoder may be used to decode the bit patterns, for example if the frequencies are sufficiently close as to cause interference. In general, techniques known to those skilled in the communications arts, especially with respect to modulation and demodulation (e.g. modems), may be employed. Examples of such techniques include the various modem standards designated as V.x (where x is an integer) promulgated by the International Telecommunications Union, Sector T, which are incorporated herein in their entirety by reference for all purposes.

In some embodiments, a server may perform signal analysis to determine the encoded data, rather than (or in addition) to on the telecommunications device. In some embodiments, signals may be stored at the server and provided to personnel for refinement of transmission and/or reception techniques.

As mentioned above, signaling may be performed by a transmitter. A transmitter may include a hardware system that incorporates a signal generator such as processor, such as a microprocessor, microcontroller, or digital signal processor connected to a memory (for example, DRAM or SRAM, which in some embodiments may be integrated with the processor) containing program instructions executable by the processor, and/or data used by the program. A transmitter may also incorporate persistent memory, such as a flash memory, coupled to the processor and/or incorporated into the processor. The signal generator may generate the ultrasonic signal that is transmitted as described above. In some embodiments, a waveform for transmission may be stored in persistent memory. In some embodiments, a transmitter includes a power supply and/or a battery, or uses the power supply used to power other components on the medical sensing device. As mentioned, the transmitter may include a transducer, for example a piezoelectric transducer that converts electrical impulses to ultrasonic vibrations. A transmitter may include an amplifier coupled (directly or indirectly, for example via an audio Digital-to-Analog Converter (DAC), which in some embodiments may be integrated with the processor) to the processor, which provides electrical impulses through its output to the transducer. In some embodiments, transmitter may include a real-time clock and/or a receiver for receiving broadcast time signals. In some embodiments, transmitter may include an encryptor, which for example may be program instructions executing on processor, or may be separate integrated circuitry. In some embodiments, transmitter may include an error correcting code generator and/or an error detecting code generator, which for example may be software instructions executing on processor, or may be separate integrated circuitry. The techniques described herein regarding transmission and reception of sonic signaling may be performed at a transmitter as described herein in a manner that will be readily understood by those skilled in the art.

In some variations, the transmission from the medical sensing device to the telecommunications device is one-way, typically providing simplicity of the design, lower expense, lower power consumption, and the like. These advantages are particularly helpful when compared to systems in which the medical sensing device includes an additional receiver (including a microphone for receiving sonic signals, or an antenna). However, in some configurations the medical sensing device may be adapted to receive a simple indicator signal from the telecommunications device without the addition of a receiver such as an antenna or microphone. For example, in some variations a return acknowledgement (ACK) could be implemented using the ultrasonic transducer (e.g., piezo speaker) as a 20 khz sensor. For example, the telecommunications device (e.g., phone) could produce a short 20 khz burst after receiving, decoding, and verifying the CRC to signal to the sensor that it received it correctly, indicating that re-transmission is not necessary. In other variations, a signal from the telecommunications device may indicate that it is ready to receive transmission from the biometric device. Pairs or multiples of timed signals/acknowledgements may also be used.

In one example, the devices or systems are configured so that the data that is ultrasonically transmitted includes forward error correction (FEC), allowing the receiver to correct N number of bit errors. This may be particularly useful if the system is configured so that the biometric device (the medical sensing device) is transmit-one (e.g., one-way). FEC may help ensure that the data is received correctly.

In some embodiments, data sent by ultrasonic signaling may be processed to include an error correcting code, such as a BCH code, a Constant-weight code, a Convolutional code, a Group code, a Golay code such as a Binary Golay code, a Goppa code, a Hadamard code, a Hagelbarger code, a Hamming code, a Latin Square based code, a Lexicographic code, a sparse graph code such as a Low-Density Parity-Check code, an LT or "Fountain" code, an Online code, a Raptor code, a Reed-Solomon code, a Reed-Muller code, a Repeat-accumulate code, a Repetition code such as Triple modular redundancy code, a Tornado code, a Turbo code, or other error correcting codes known to those skilled in the art. In various embodiments, such codes may be applied in a single dimension or in multiple dimensions, may be combined, and may be combined with error detecting codes such as parity and cyclic redundancy checks. Error correcting codes may be decoded and applied to correct transmission and/or reception errors at a receiver, or at a server receiving communications from a receiver, according to their respective techniques.

Example 1: Digital Thermometer

In one example, a digital thermometer may be configured to include a digital ultrasonic modem. In this example, a digital thermometer based on a Texas Instrument MSP430 digital thermometer has been adapted to include firmware so that it may ultrasonically transmit the temperature reading (digital data) to a mobile telecommunications device (e.g., iPhone). Although this example is specific to the APE 4110 microprocessor (one variation of the MSP 430 microprocessor from Texas Instruments) other microprocessors may be used and similarly adapted with firmware, software and/or hardware to function.

In general, the device may take data (e.g., thermometer temperature readings) and encode them for ultrasonic transmission. The encoded signal may include error checking (e.g., CRC encoding, Hamming codes, etc.) and may be encrypted. For example, the data may be data encrypted using, for example Advanced Encryption Standard (AES). U.S. Pat. Nos. 5,481,255 and 5,452,356 both describe data encryption methods and techniques that may be used with the data described herein.

For example, data received from the thermometer may be encoded and/or encrypted into one or more data packets for transmission. The microprocessor may encode the data and may then transmit the packets by driving the piezo speaker. As mentioned above, Frequency Shift Keying (FSK) may be used, in which two separate ultrasonic frequencies (e.g., 18817 Hz and 19672 Hz) are used to transmit Boolean 0 and 1, respectively. The control logic (data ultrasound modem logic) may both configure, encode and encrypt the data and may also control driving the transmission of the prepared packets of encoded/encrypted data by the speaker (e.g., piezoelectric transducer). The control logic may also control the timing of the delivery, so that there is adequate spacing between each data bit. In addition, the control logic may also repeat the transmission and time the start of the transmission.

For example, in one variation the thermometer typically measures temperature, and once the temperature has settled to a value, the thermometer emits an audible beep to alert the user that the value can be read. This thermometer (in the initially unmodified configuration) includes a microcontroller (e.g., the AFE 4110) and a piezoelectric speaker; the microcontroller drives the speaker to emit the beep. By modifying/configuring the microcontroller as described herein to include the control logic for the digital ultrasound modem, the thermometer may be adapted to "wirelessly" (via ultrasound) transmit the thermometer data to a device configured to receive and decode/decrypt the signal such as a smartphone running digital ultrasound modem receiver logic.

In this example, the microprocessor may include the following (exemplary) code to enable the functionality described above. FIGS. 23 and 24A-24E show flowcharts describing methods for transmitting data. These examples are not limited to digital thermometers, but may be used with any of the devices described herein, including ECG transmission.

Although the above steps show the methods of FIGS. 23 and 24A-24E of transmitting data, a person of ordinary skill in the art will recognize many variations based on the teaching described herein. The steps may be completed in a different order. Steps may be added or omitted. Some of the steps may comprise sub-steps. Many of the steps may be repeated as often as beneficial.

One or more of the steps of the methods of FIGS. 23 and 24A-24E may be performed with circuitry as described herein, for example, one or more of a processor or logic circuitry of the computing device or an accessory thereof. The processor or logic circuitry may be programmed to provide one or more of the steps of the methods, and the program may comprise program instructions stored on a computer readable memory or programmed steps of the logic circuitry.

In any of the systems, device, or methods described herein data (including digital, analog, and/or hybrid digital/analog data) may be compressed before it is encrypted. Any appropriate data compression technique may be used. For example, data compression may be performed using lossy and/or lossless techniques. Known types of lossy and lossless data compression may be used. For example, Lempel-Ziv (LZ) compression and other statistical redundancy techniques may be used for lossless compression. Similarly, lossy data compression techniques may also be applied. The receiver executing the control logic may decompress the data.

Ultrasound Digital Modem Receiver

As mentioned above, a receiver (a digital ultrasound modem receiver) may be used to receive the transmitted ultrasound signal. The receiver may be a dedicated device include a microphone competent to receive ultrasound signals and a processor capable of analyzing the signal (e.g., microprocessor) or it may be a device having microprocessor and microphone that is adapted to receive the ultrasound signal when executing control logic (e.g., digital ultrasound modem receiver logic).

Figure 25:
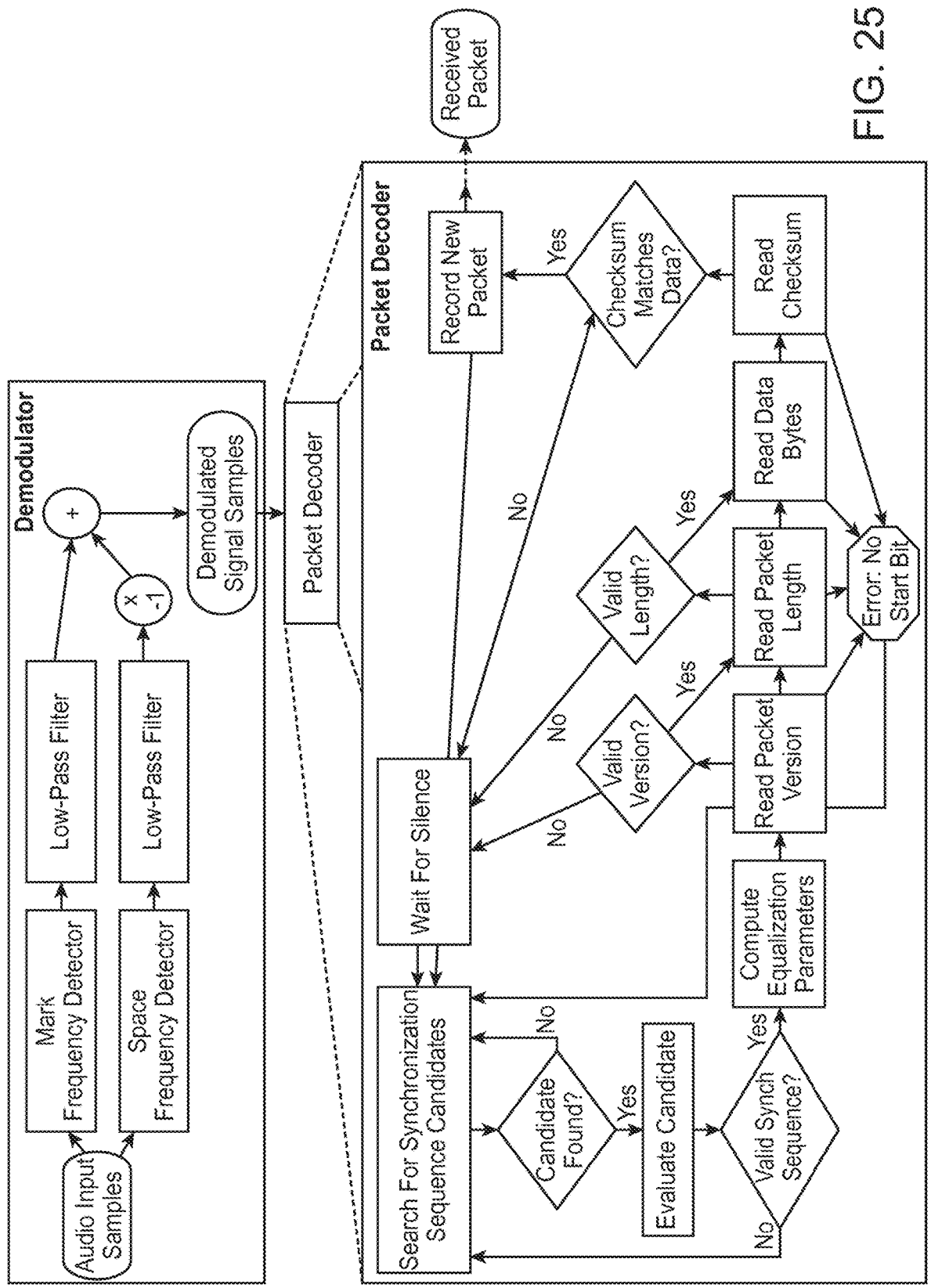
FIG. 25 shows one example of flowchart of a demodulator and packet decoder for a receiver configured to receive and decode data that is transmitted ultrasonically as discussed herein.

For example, FIG. 25 illustrates one variation of a flow diagram illustrating a method for receiving, demodulating and detecting the digital ultrasound signal. In this example, the application (the receiving control logic) receives binary-FSK encoded data via a microphone input. For example, the input may be from the microphone on a smartphone. As discussed above, Binary FSK encoding uses two frequencies, a "mark" frequency Fr, to represent a binary 1, and a "space" frequency $F_s$ to represent a binary 0. In this implementation, no carrier is used.

The application consists of two largely independent components: the demodulator, which extracts the mark and space frequency components from the raw audio data, and the packet decoder, which monitors the demodulated signal for packet transmissions and decodes them. These are illustrated in FIG. 25. The demodulator receives audio samples from the microphone hardware at a sample rate S, such that $S>2*max(F_m, F_s)$. The audio samples are processed by two frequency detectors that calculate the intensity of the mark and space frequency components (respectively) of the received signal. A Goertzel algorithm is used for frequency detection in this implementation. In order to achieve sufficient frequency resolution between the mark and space frequencies, we apply the Goertzel algorithm to a sliding window of G samples, where $G=S/abs(F_m-F)$.

The output of the Goertzel algorithm for the mark and space frequencies is passed to independent low-pass filters, with a passband equal to the baud rate. The filtered output of the space frequency signal is then subtracted from the filtered output of the mark frequency signal. This produces a waveform that is approximately 0 when there is no transmission occurring, rises to a positive value when the "mark" frequency is active, and falls to a negative value when the "space" frequency is active.

This demodulated waveform is then passed to the packet decoder. For each raw audio sample received from the microphone hardware, the demodulator produces a single demodulated sample of the demodulated waveform. The packet decoder receives demodulated samples from the demodulator. The decoder maintains a buffer of the last N samples received, where N is equal to the length of the synchronization sequence. With each new sample, the decoder evaluates the past N samples in the buffer to determine if they contain the synchronization sequence. A two-stage test is used—first a computationally simple evaluation that eliminates most false positives due to random noise, and then a more computationally expensive evaluation that eliminates the rest.

Once a valid synchronization sequence is received, the decoder stores properties of the received signal (e.g. maximum mark/space amplitudes, etc.). These equalization parameters are used to calibrate the decoder thresholds used to read the remainder of the packet. The decoder in this example then reads each encoded byte in turn. It uses the stored equalization parameters to determine a minimum amplitude threshold for the start bit of each byte. Once a valid start bit is received for a given byte, subsequent bits are evaluated based on the sign of the demodulated waveform, with no minimum threshold for decoding.

If no valid start bit is received, the decoder aborts reading the packet and waits for silence, or until a fixed amount of time has passed, before resuming listening for new packets. Each logical byte in the packet is actually transmitted as two encoded bytes—the first containing the Hamming-encoded low nibble of the logical byte, and the second the Hamming-encoded high nibble.

The first logical byte read is the packet version, which is checked against supported version numbers. Next the packet length is read, specifying the number of data bytes to follow. If the packet length exceeds the maximum length for the specified packet version, the packet is rejected. Subsequently, each logical data byte is read.

After the data bytes are read, two logical checksum bytes are read, and the checksum value received is compared to the value computed for the data bytes received. If these two checksum values match, the packet is considered valid, and is made available to the remainder of the application. If they do not match, the packet is rejected. The two logical checksum bytes represent the end of the packet. After receiving the packet, the decoder resumes listening for new packets.

Once data is received (and in some variations decrypted), it may be processed further and/or stored, and/or displayed, and/or transmitted on using any of the communications capabilities of the telecommunications device. For example, the data may be displayed on the smartphone and/or uploaded into a medical database for storage and/or later review.

Although the above steps show the method of FIG. 25 of transmitting data, a person of ordinary skill in the art will recognize many variations based on the teaching described herein. The steps may be completed in a different order. Steps may be added or omitted. Some of the steps may comprise sub-steps. Many of the steps may be repeated as often as beneficial.

One or more of the steps of the methods of FIG. 25 may be performed with circuitry as described herein, for example, one or more of a processor or logic circuitry of the computing device or an accessory thereof. The processor or logic circuitry may be programmed to provide one or more of the steps of the methods, and the program may comprise program instructions stored on a computer readable memory or programmed steps of the logic circuitry.

Although the example above describes a system configured to transmit digital information, the techniques, device and systems described herein may be configured to transmit analog signals as well, and/or analog and digital hybrid signals. In general, the techniques described include the use of a timer (e.g., in the microcontroller) transmitting to a piezo to generate the ultrasound signal. Alternatively, in some variations the system uses a D/A converter to drive a speaker for non-digital output. Further, in some variations the system the output is not a piezoelectric element but is a more traditional speaker (albeit in the ultrasound range). Additional digital to analog (D/A) conversions may take place during transmission.

Figure 26B:
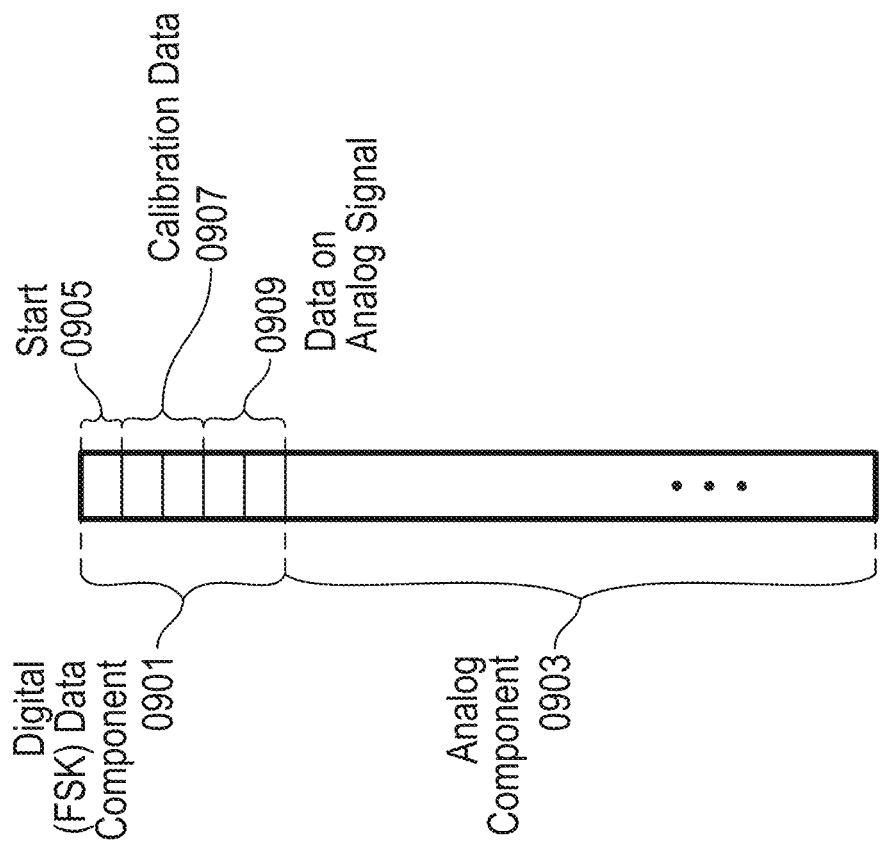
FIG. 26B shows another exemplary format for a hybrid digital and analog ultrasonic data format.
Figure 26A:
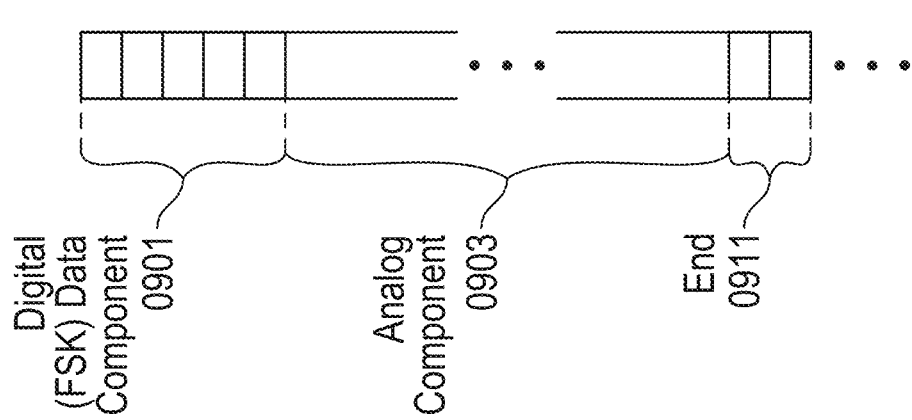
FIG. 26A shows one exemplary format for a hybrid digital and analog ultrasonic data format.

For example, FIGS. 26A and 26B illustrate one variation of a hybrid digital/analog format that may be used with an ultrasound transmitter. In general, the signal may include a digital component that is modulated or configured for ultrasound modem transmission. For example, the digital signal may be encoded as an FSK signal, and data (e.g., analog data such as biometric data like ECG, blood oxygen/pulse ox, etc.) may be encoded as frequency modulated waveforms that are appended to the digital information.

For example, in some variation the ultrasonic transmission device is configured as a pulse-ox measuring/monitoring device. In this example, information taken from the pulse-ox may be examined to extract information, such as the minimum, maximum, analog signal duration, etc. and may be digitally encoded an placed (using one or more encryption and/or error correction codes) in a buffer and/or transmitted by ultrasound. The analog signal may be combined with the digital signal (or extracted signal) that can be sent to the transmission element and received by a telecommunications device. In the example of a device configured as a pulse oximetry device (e.g., plethsmograph), the pulse oximetry device prepares the hybrid data/analog signal by determining from the analog signal (e.g., a time varying pulse oximetry signal) the peak, minimum, duration, time interval, etc. of the analog signal. Thus, the hybrid signal may include the extracted or tagging digital information as well as a waveform (or waveforms) taken from the device.

In some variations, the signal may be ECG data. The ECG header information may include digital information about the analog waveform that is appended to the digital information, such as the duration, pulse rate, information about the ECG waveform (if pre-analyzed), such as interval data, etc.

The signals may be sent encrypted by a device or user specific identification code. In general any of the devices described herein may encode the data, and an encryption key may be provided so that it can be read and understood by a receiving telecommunications (e.g., phone, tablet, pad, etc.).

There are many potential benefits to transmitting a hybrid analog/digital signal that can be read and understood by the telecommunications device. For example, if a hybrid signal includes a series of values (e.g., min/max) and waveform (e.g., ECG, hear rate, etc.). This kind of hybrid digital/analog system may allow more efficient communication than just FSK value data alone.

For example, variations of ultrasonic transmission devices may include a pedometer, an activity monitor, a heart-rate monitor, etc. In some variations, the signal is formatted so that there are a finite number of points in the analog portion. The ultrasound transmitting device may then send a series of data points (including any including calibration points). In one example, a graph of heart rate may include 1000 points in 2 seconds (transmission time) representing a graph of biometric data over time. The signal may include digital values (encoded as FSK, for example) and analog (e.g., graphic) data. Such a hybrid signal may include the best characteristics of both digital-only and analog-only signals.

In one example, previously mentioned above, an ultrasonic transmission device is a thermometer that includes the ultrasonic modem elements described above. The ultrasound thermometer device may be configured to include a temperature range of about 95° F. and 106.7° C. for an actual use range. Thus, temperature may be normally transmitted as having 0.1 resolution (e.g., 120 values, so 8 bits may be all that are needed). In devices configured to encode the biometric data in a hybrid signal, the digital component of the signal may be appended first and may include information about the analog signal that follows the digital-only, while the analog signal may be appended or embedded in the rest of the signal and the digital information may be extracted from the digital signal to be included with it. Examples of hybrid signals may include a thermometer device as mentioned above, which displays temperature as a function of time, and measures and/or records and transmits the maximum/minimum temperature, the time measured, etc., finally the signal may also include a temperature waveform showing time course. Other devices and/or signals (hybrid signals) may be include glucose monitor signals (e.g., configuring the ultrasonic transmission device as a glucose meter, etc.), which may send blood sugar signals (digital signals including max, min, etc.) and one or more graphs showing waveforms of blood glucose over time, etc.

Preparing and transmitting a signal to include both analog and digital information may also allow the system to send more data in compressed form as a waveform, which can be very efficient. For example, prototype ultrasonic transmission devices apply a specific sampling rate (e.g., 300 or 500 samples/sec., where each value is a 16 bit binary value). More data can be efficiently sent in compressed form as a waveform. Including extracted information (such as min and max values of the analog signal) in the digital portion of the signal may provide the axis calibration for the analog portion of the signal, e.g., for display.

As mentioned, FIG. 26A shows one variation of a hybrid digital/analog format that may be used as described herein. In this example, the signal includes an initial digital component 0901 that is encoded for ultrasound transmission using a technique such as FSK (or any of the other techniques known in the art). The digital information may be broken into bits, byte, words, etc. as appropriate. The size and position of digital information may be predetermined. Error correction codes (e.g., hamming codes, etc.) may be included. In FIG. 26A, the signal includes a start bit or bytes 0905, a sequence of calibration data 0907 extracted from the analog signal (e.g., max/min), additional data 0909 on the analog signal (e.g., type, timing, data stamp/time stamp, etc.). Any other digital information may be included. Thereafter, the signal may include an analog component 0903. In FIG. 26A, the analog signal is somewhat open-ended, and may continue for a fixed or unfixed duration; in some variations the entire signal may be repeated for receipt by the telecommunications device. FIG. 26B shows a similar variation of a hybrid signal format, in which the digital component 0901 is appended to an analog component 0903, and an additional digital component 0911 ("end" signal) may be appended at the end. In some variations, multiple analog components maybe combined with multiple analog components. As described below, the entire signal may be encrypted prior to transmission.

In some variations, hybrid digital/analog formats may be used to encode stored data that has been held by the device (the ultrasonic transmission device) for some amount of time. For example, stored data such as an hours, days, or weeks' worth of data (e.g., biometric data such as pedometer data) may be prepared as an analog signal (graph overt time)

that is described/calibrated by the digital data component, and sent to a telecommunications device.

In any of the devices, systems and methods described herein, the ultrasonic signal transmitted by the device may be encrypted. Any appropriate encryption method may be used, including encryption methods that use keys, such as data encryption standard (DES), advanced encryption standard (AES), and the like.

In general, the encryption key for a particular device (e.g., ultrasonic transmission device) may be presented on the device (or on the associated packaging, housing, etc. for the device, so that it can be easily accessed by a user of a receiving telecommunications device. The encryption key may be prepared as a bar code or other machine readable format (e.g., QR code), and particularly readable formats that can be read using the receiving telecommunications device in a different modality than the ultrasound transmission. As used herein, reference to presenting or displaying an encryption key on the ultrasonic transmission device is intended to encompass displaying a prepared representation (and particularly a machine-readable representation) on the ultrasonic transmission device, it's packing or associated structures (e.g., housing, etc.). In some variations, the encryption key is prepared as a bar code or QR code and printed on the outside of the ultrasonic transmission device so that it can be photographed or scanned by the telecommunications device. The machine executable logic (e.g., client logic, software, firmware, etc.) on the telecommunications device may then determine the encryption key and apply it to decrypt the ultrasonic signal received from the ultrasound communications device.

In this manner, an ultrasonic transmission device may be paired uniquely with a private encryption key that can be read only by a telecommunication device possessing and applying the encryption key. The encryption key (encryption key) is readily displayed an easily determined by the telecommunications device. Thus, in some variations, each ultrasonic transmission device may have a unique ID that is printed on the device, providing a code that must match with the telecommunications device. Scanning the printed encryption key allows the telecommunications device to decrypt the data.

Figure 27:
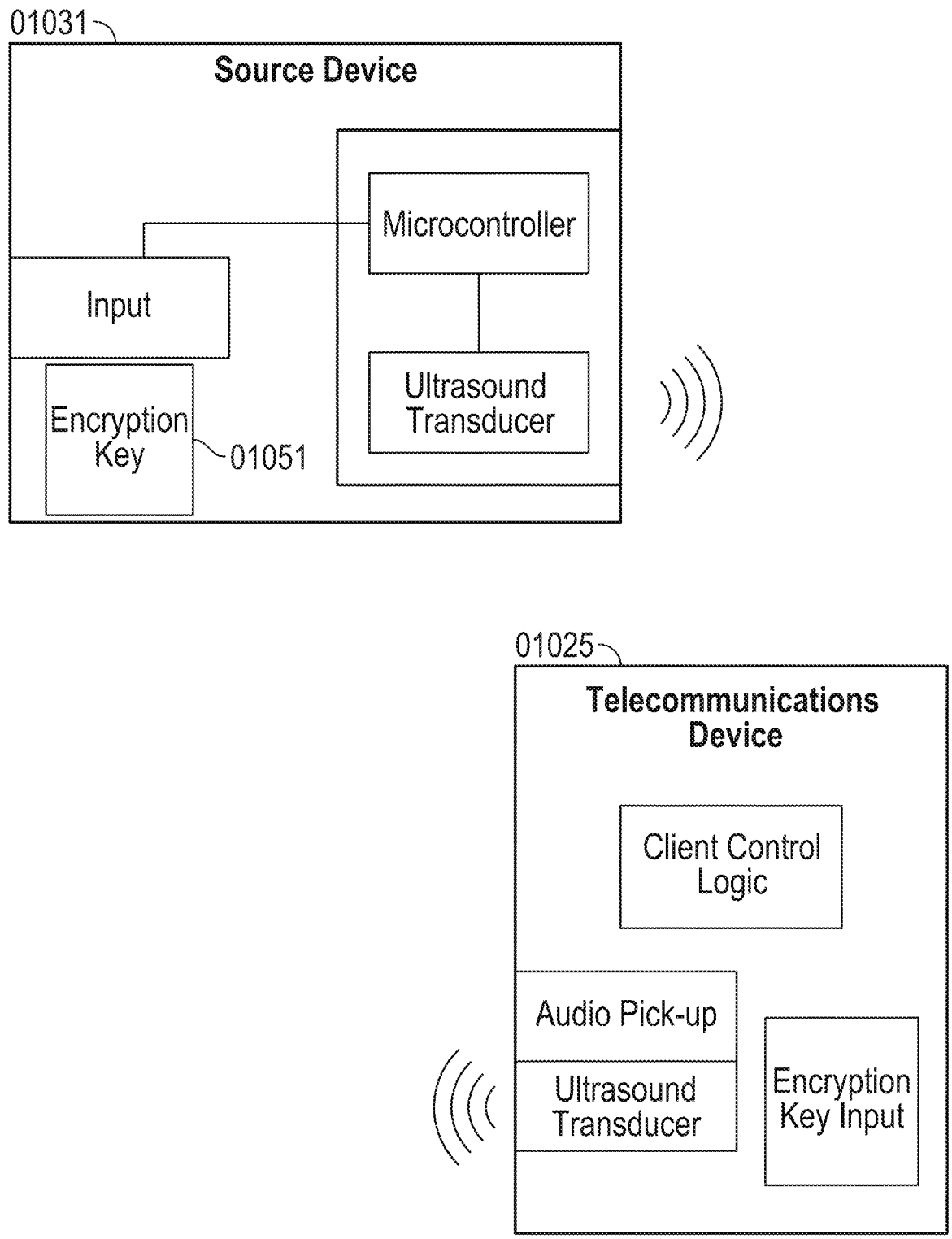
FIG. 27 is a schematic illustration of a system for secure ultrasonic transmission of data including an ultrasonic communications device with an ultrasonic transducer and an encryption key located on the ultrasonic communications device and decrypting logic executable on a telecommunications device, wherein the telecommunications device comprises a receiver for receiving an ultrasonic signal from the ultrasonic communications device.

FIG. 27 illustrates schematically one variation of a system including an ultrasonic transmission device ("source device" 01031) with an encryption key 01051 visible on the body of the device that can be read and applied by the telecommunications device 01025 to decrypt the transmitted ultrasonic transmission. FIG. 27 also illustrates one variation of a device and system in which the ultrasonic transmission device ("source device" 01031) is in two-way (or limited two-way) communication with the telecommunications device.

As mentioned above, it may be useful to have communication between the telecommunications device (e.g., smartphone or computer) and ultrasonic transmission devices such as healthcare/fitness sensing devices, home automation and security devices (door and window sensors, remote light switches, etc.), plant water level detectors, etc. For instance, it would be helpful to implement a half-duplex protocol so that the telecommunications device (e.g., smartphone/computer) could provide acknowledgement (ACK) to the sensing device (source device or ultrasonic transmission device) that the data has been successfully received (with correct CRC) and to stop re-transmitting that data. Another use of this half-duplex protocol would be to configure the remote device by sending parameters or information such as calibration data, personal information, etc. from the telecommunications device.

For simple acknowledgement, the piezo/speaker used by the device to transmit data (ultrasonic transmission device) could be used as a frequency tuned sensor. In general, a piezo for transmission of sound may also be configured as a receiver. Using a piezoelectric element as a receiving sensor requires a relatively "loud" signal (even if it's inaudible) and thus the signal should be at the resonant frequency of the piezo at which it is most sensitive. The duration or encoding of such a "frequency burst" could be configured so as to be recognized easily by the low power electronics of the healthcare/fitness sensing device. For example, an acknowledgement pulse could be filtered and detected as just a presence of a certain ultrasonic frequency for a predetermined duration.

In some variations, symmetric two-way communication can be accomplished using well-established telephony modem techniques, only changing the carrier frequency into the ultrasonic range. For instance, telephony modem modulation techniques, based on FSK (Frequency shift keying), QAM (Quadrature amplitude modulation), and PSK (Frequency shift keying). These telephony modem techniques assume only two devices are attempting to communicate. Radio frequency protocols can be used to augment the modem protocols to allow for multiple devices to communicate simultaneously without error.

Implementations of such two way communication techniques may include additional processing power in the device sufficient to perform the signal processing necessary to demodulate and decode the received audio. This processing power may require additional battery power as well as physical space in the device. A partial list of existing modem communication standards that could be adapted to ultrasonic communications may include: ITU V.21 (300 bps, FSK), and ITU V.22 (1200 bps, PSK (Phase shift keying)). See, e.g., reference webpages such as: ftp://kermit.columbia.edu/kermit/cu/protocol.html, http://www.LSU.edu/OCS/its/unix/tutorial/Modem Tutorial/ModemTutorial.html, http://www.dtic.mil/cgi-bin/GetTRDoc?AD-ADA499556, http://alumni.media.mit.edu/~wiz/ultracom.html, http://nesLee.ucla.edu/fw/torres/home/Dropbx/good_paper_mico_controller.pdf, http://edocs.nps.edu/npspubs/scholarly/theses/2010/Sep/10Sep_Jenkinds.pdf.

With respect to FIG. 27, the source device may include an additional transducer/microphone for receiving ultrasound signals from the telecommunications device, as well as supporting processing (e.g., microprocessor/microcontroller logic) to control it, interpret communications (which may encoded and/or encrypted) and execute any command functions. Similarly, the telecommunications device may include a speaker (piezo) configured to emit ultrasonic signals.

From the above descriptions, it is clear that the presently disclosed and claimed inventive concept(s) are well-adapted to carry out the objects and to attain the advantages mentioned herein, as well as those inherent in the presently disclosed and claimed inventive concept(s). While the presented embodiments have been described for purposes of this disclosure, it will be understood that numerous changes may be made which will readily suggest themselves to those skilled in the art and which are accomplished within the spirit of the presently disclosed and claimed inventive concept(s).

Example 2: Heart Rate Monitor Using Audio Tones for Heart Rate Transmission

Any of the devices, systems and methods described herein may be configured as wireless (ultrasonic) heart rate monitors that are compatible for use with a mobile telecommunications (computing) device, such as a smartphone. See also, below, in Example 3, describing a wearable ECG monitor that may also provide heart rate information (e.g., by extracting heart rate from detected ECG signals). A wearable component for sensing heart rate (e.g., wearable monitor) may be configured as a wristlet, anklet, armband, chest strap, belt, etc. (collectively "strap") and may transmit information wirelessly via any of the ultrasonic methods described above, including the use of receiving control logic (e.g., software, hardware, etc.) to receive, store and/or analyze the sensed (biometric) information.

Most heart rate monitors consist of a chest strap incorporating an ECG amplifier, R wave detector and circuit to output a 5 kHz electromagnetic pulse typically 50 ms wide when an R wave is detected. This electromagnetic pulse is detected by a watch or other receiver which then measures the interval between the pulses and calculates and displays the heart rate. This configuration requires a special receiver which may not be present in mobile phones or computers, so without additional equipment they cannot receive the heart rate information. The range is also limited to approximately 1 meter as it typically uses near field electromagnetic transmission.

In one variation of the devices and systems described herein, a heart rate monitor may include a strap (e.g., a chest strap, wristlet, etc.) incorporating an ECG amplifier, R wave detector and circuit to output an audio time (signal) typically 5 ms wide when an R wave is detected (e.g., within the ultrasound frequency region of approximately 17 kHz to 30 kHz). This audio tone may be detected by a device such as a smartphone or other mobile computing device using the in-built microphone on the smartphone device that can then measure the interval between the tones and calculate and display the heart rate. The mobile computing device (e.g., phone) may include software, firmware or hardware (though typically software, including an application or "app" that can be downloaded from a remote server) for controlling the mobile device to receive and analyze the audio (e.g., ultrasonic) tone, calculate the heart rate, and store, upload and/or display the heart rate.

One advantage of this system is that no additional equipment is required to receive the heart rate information as the microphone circuit is already present in the smartphone or other mobile computing device, and that the range can be longer, with a range of 5 m or more if desired depending on the loudness of the audio tones.

When audio tones in the range 16 kHz-32 kHz are used (e.g., ultrasound, 17 kHz-30 kHz, 17 kHz-22 kHz, etc.), then they are inaudible to most people, will not interfere with music or speech, and also be less prone to audio interference.

In some variations, the devices, methods and systems may be configured so that multiple heart rate monitors can be used in close proximity, or for one receiving device to receive heart rate information from multiple users simultaneously. It may be desirable that the heart rate information from each heart rate monitor be uniquely identifiable so they do not interfere with each other.

For example, the audio tones from each heart monitor can be uniquely coded for each monitor by using a range of tone durations, multiple tone of the same frequency with specific time spacing, different audio frequencies or a combination of these.

A first embodiment is one where each heart monitor uses a different audio frequency, spaced sufficiently apart to allow for Doppler shift when the heart rate monitor is moved rapidly relative to the receiver, and to allow frequency discrimination with a high signal to noise ratio.

So each heart monitor does not have to be set to a particular tone frequency, the frequency can be determined by a pseudo random sequence when the heart monitor first detects an R wave heart beat signal after first being put on. The audio tone is then fixed until the heart monitor is removed. Thus, each monitor does not then have to be uniquely coded.

Where the heart rate monitors emit audio tone is in the range 18 kHz-22 kHz then a 500 Hz separation may be used. This allows 9 possible audio frequencies of operation for each monitor.

The pseudo random allocation of the frequency to be used can be achieved by having a counter that increments with time from when the heart monitor is first attached to the body, such that the counter value when the first R wave is detected determine the audio frequency to be used. The audio frequency can be changed by detaching and reattaching the monitor the body.

In the above example, in the rare circumstance where two heart monitors are using the same frequency and are in close proximity so there may be some likelihood of interference, the frequency of one monitor can be changed by removing it and reattaching it. The receiving device can also detect such interference and advise the user to remove and reattach the monitor if necessary.

The receiving device can determine the audio tone frequency of particular ultrasound transmitting devices (in this example, heart monitors) by performing spectral analysis of the received audio. Once the audio tone frequencies are known then narrow audio filters are used to separate the tones from each heart monitor. The audio tones can then be detected, and the heart rate calculated by measuring the interval between audio tones. As the duration of each audio tone is fixed, this information can be used to reject interference from other audio sources in the frequency band.

A second embodiment is where multiple devices (e.g., heart rate monitors) use audio tones of the same frequency but with different durations. The duration of each tone may be measured by the receiving device. Only the tones of a specific duration are used to calculate the heart rate for a particular heart rate monitor. Where two heart rate monitors are in close proximity, so that the receiving device picks up the audio tones from both monitors simultaneously, it can distinguish between them based on the tone duration. The audio tones are unlikely to arrive simultaneously as the tone duration is short compared to the interval between tones (the heart rate interval), but if they do arrive simultaneously this can be recognized by the receiving device and the heart rate calculation may be adjusted to compensate.

In some variations, the audio signal emitted when heart beat is detected may be digitally encoded (e.g., including a burst of multiple pulses at high frequency) and the encoding (burst pattern) may be unique or preselected (random) as mentioned above, and reset by the user (e.g., by taking the device off and reapplying it).

Any of the examples discussed above may be included as part of a method, device or system (including software). Thus, a system for measuring heart rate may include a monitor (e.g., heart rate sensor, etc.) including a transducer for creating an audio signal (e.g., pulse or pulses) timed with the patient's heart rate. Thus the monitor acts as an audio repeater. The audio signal maybe in the ultrasound range. The system may also include control logic to control a mobile device such as a smartphone or tablet to receive and analyze the audio signal timed with the users pulse rate. In some cases, a dedicated receiver may be used instead or in addition to a smart phone running control logic.

In a particular example, the system may include an application for use on a mobile device such as a smart phone that controls the smartphone to use the internal audio pickup (microphone) to receive the audio signal emitted by a sensor and calculate heart rate from this audio (e.g., ultrasound) pulsed signal.

Example 3: Wristlet for Detecting Motion and/or ECG Signals

Figure 28A:
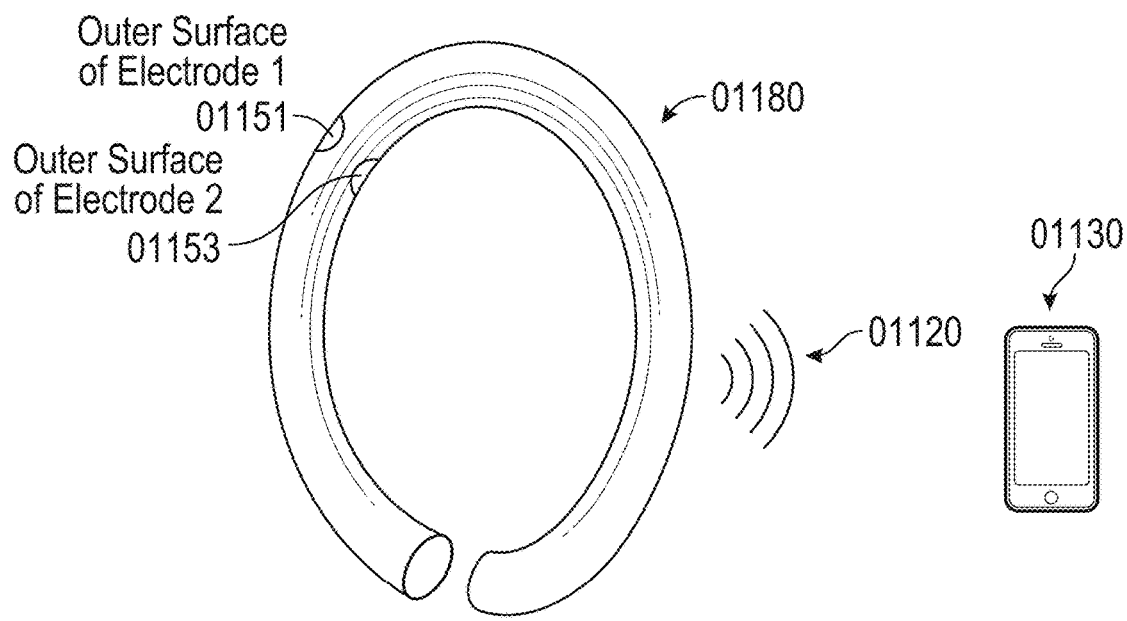
FIGS. 28A and 28B illustrates one variation of a wristlet device for sensing one or more biological parameters and for transmitting it wireless at extremely low power to a mobile communications/computing device (FIG. 28A shows an external view of the wristlet while FIG. 28B illustrates a schematic of the internal region including various modules for sensing, power and transmission of ultrasound signals, and many of these elements are optional)
Figure 28B:
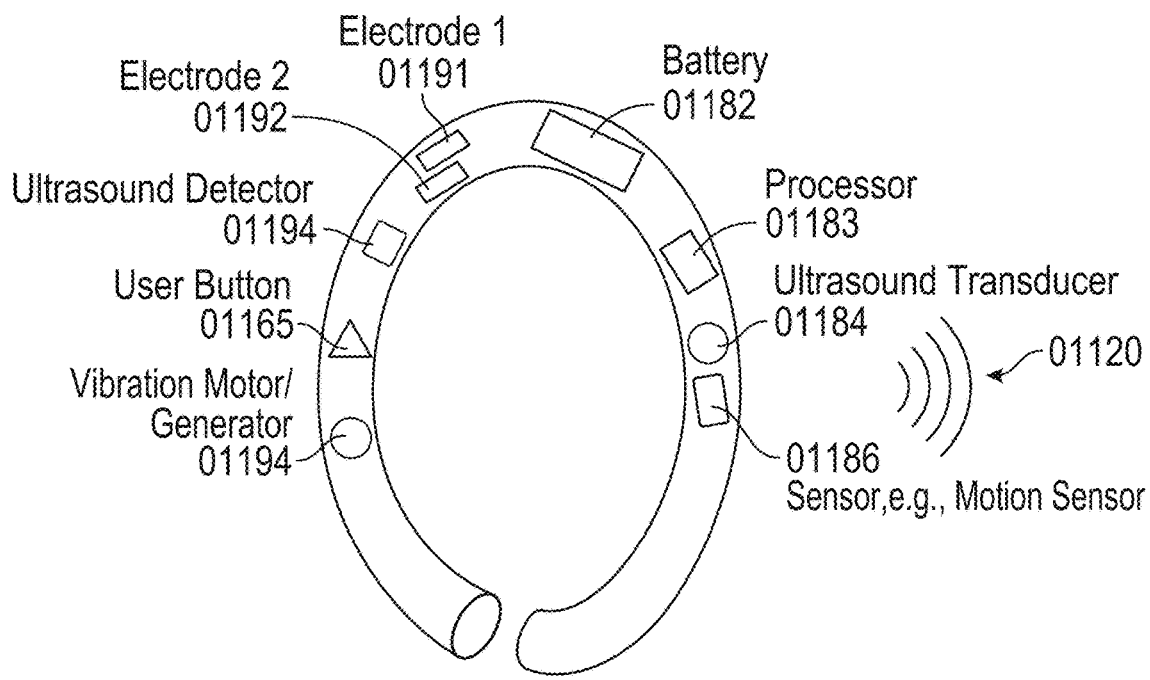

FIGS. 28A and 28B illustrate another variation of a wearable device that may detect a health parameter and ultrasonically transmit it to a monitoring station (e.g., smartphone) controlled by control logic so that it receives and/or provokes receipt of information ultrasonically from the wearable device.

FIG. 28A shows an external view of one variation of the device 01180, configured as a wristlet. The device may include one or more sensors for detecting a biological parameter, such as a motion/vibration sensor, and one or more electrodes. In FIG. 28A, the outer surface of the device is shown schematically. A first electrically conductive (e.g., metal) window 01151 is visible on an outer surface of the wristlet, and a second electrically conductive (e.g., metal) window 01153 is visible on an inner surface of the wristlet. These electrodes may allow the user to press down on the electrodes and wristlet to make electrical contact with the skin. The inner electrode may make constant or periodic contact during normal use. The electrically conductive window may also be thermally conductive and may be connected to a temperature-sensing module as well.

The wristlet may be flexible so that it can be extended over and secured to a wearer's wrist. The wristlet may be bendable so that, once bent around the wearer's wrist, it remains in position. In some variations, the wristlet is open; in some variations the wristlet may be closed (forming a closed loop over the subject's wrist). The outer surface of the wristlet may be sealed from the inner surface to prevent damage, and to make the wristlet sweat-proof and water-proof while being worn.

As illustrated above for the electrically conductive window regions, the outer portion of the wristlet may be adapted to transmit energy from the modules within the wristlet through the outer protective housing. For example, the conductive window regions shown above. The region of wristlet covering the ultrasound transducer 01184 may also be adapted to permit passage of ultrasonic signals 01120. In some variations, the end of the wristlet is adapted to permit passage of an ultrasonic signal by including a relatively rigid end cap that can readily transduce ultrasonic energy. In some variations the outer (e.g., polymeric) covering is made of a material that is known in the art to be relatively transparent to ultrasound. In some variations, the end region (or the opposite end region) may also be adapted to allow recharging of the battery of the device.

FIG. 28B illustrates an exemplary internal schematic of the wristlet, illustrating the internal modules (structures). As mentioned, any appropriate sensor(s) may be included, including any of those mentioned above. In this example, the wristlet includes a motion sensor 01186, which may be a high-precision motion sensor for tracking body movement. Other sensor in this example include a first electrode 01191 and a second electrode 01192 that can be electrically connected to the conducive windows 01151, 01153 on the outer surface. In some variations, the outer surface is the electrode(s). In other variations, the conductive surface extend (e.g., for the lower electrode) around the length of the inner surface of the wristlet, so that contact with at least part of the bare skin of the wrist is likely whenever the device is worn. Similarly, the outer conducive surface of the upper electrode may extend completely around the outer (outward-facing) surface of the wristlet. Additional sensors may be included or omitted. For example, in one variation the wristlet includes only the motion sensor, but not the electrodes.

In some variations, the wristlet also includes a tactile feedback element, vibration motor 01194. This vibration motor may produce an oscillatory frequency to provide feedback to the user from the device. In some variations, the wristlet may also include a button or contact region 01165 allowing the user to manually trigger one or more functions of the wristlet and/or monitoring station, such as transmission of data by ultrasound. The button may be pressed or activated through the protective outer covering of the wristlet and the outer covering may indicate by pattern, color or the like, where the button can be pressed.

The wristlet may also include a processor 01183 for receiving and/or encoding information from the one or more sensors, as well as an ultrasound transducer 01184. As discussed above, the transducer may receive encoded/encrypted information from the processor for transmitting via ultrasound. When multiple sensors are included, the information may be encoded to indicate what data is included.

One or more memory modules (not shown) may also be included for storing recorded information. The memory may be integrated with the processor. In some variations a separate ultrasound detector 01194 may also be used, or the ultrasound transducer 01184 may be competent for both sending and receiving ultrasound signals 01120. Thus two-way communication may be possible by ultrasound between the device and a monitoring station (e.g., smartphone running control logic).

The wristlet may also include a power management system, including a battery 01182, which is typically rechargeable. The battery may be relatively low power (e.g., low voltage such as 1.5V), sufficient to power the electronics and ultrasound transducer. The processor may manage the power, including charging of the battery. The system may indicate (e.g., by vibration of a warning pattern of vibrations) that the battery is low and in need of recharge.

In operation, the wristlet may be worn and used to monitor a subject (e.g., physical activity) and may record and/or wirelessly transmit the sensed values for the subject. For example, motion sensor data may be detected and transmitted by ultrasound to a mobile computing device (e.g., smartphone 01130). As discussed above, the sensed data may be encoded (e.g., as both analog and digital information) and encrypted, which may prevent interference between other devices (e.g., allowing specific keying between devices) and also allowing error correction.

For example, a wristlet device (e.g., activity monitor) may be worn by a subject. As it is worn, the device may record the motion (activity) of the wearer. The device may also include and additional sensor, such as a pair of electrodes. These electrodes may be used to measure an ECG across the patient (e.g., between the patient's arms), when the subject presses down on the outer surface of electrode one. In some variations pressing down may also trigger the device to record the electrical potential for this time period. The recorded electrical signal may include information about pulse and ECG which can be passed on directly or initially analyzed by the processor and then passed on (including passing any analyzed information).

The device may be configured to transmit continuously (E.g., broadcasting via ultrasound) and/or repeatedly the data or it may be configured to handshake with the smartphone (or other receiving station). For example, the wristlet device may be configured to standby until an ultrasound trigger ('ready') is received by the ultrasound transducer/detector (01184/01194). The wristlet may then communicate with the receiving station to transmit, by encoded/encrypted ultrasound as described above, the data collected. The system may be configured to periodically transmit, or to attempt transmit when sufficient data has been collected.

In general, any of the techniques, components and/or subsystems described above may be use or combined with any of the other examples. For example, any of the ECG wristlet devices described herein may include any of the features mentioned above.

Example 3: ECG Detecting Wristwatch

Figure 29:
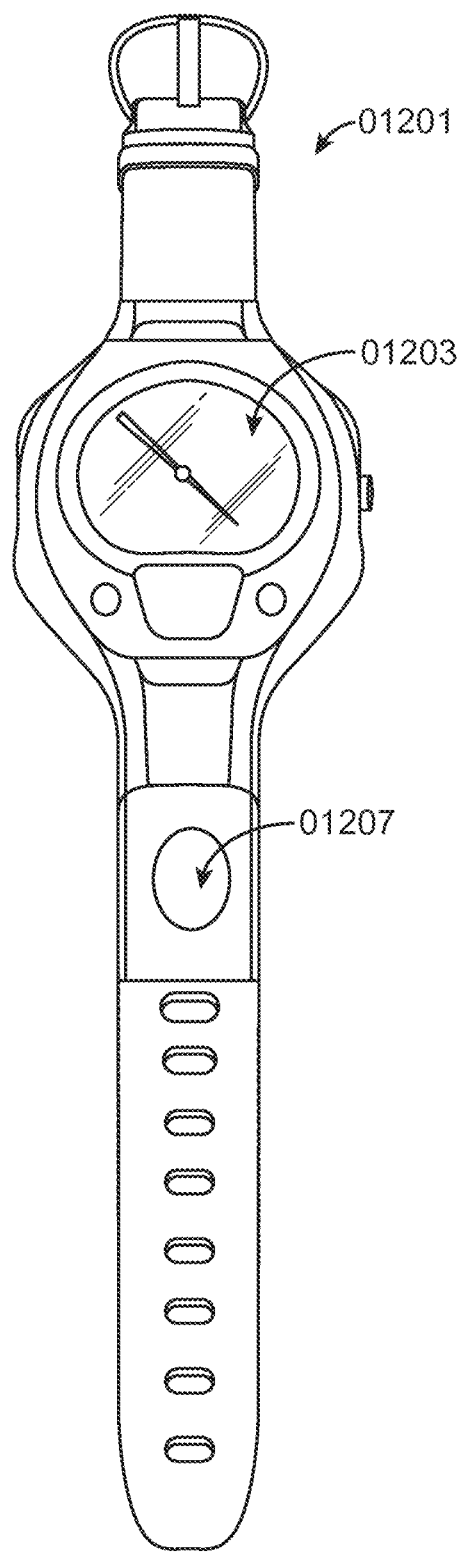
FIG. 29 shows one variation of a wristlet configured as a watch for detecting ECG signals.
Figure 30:
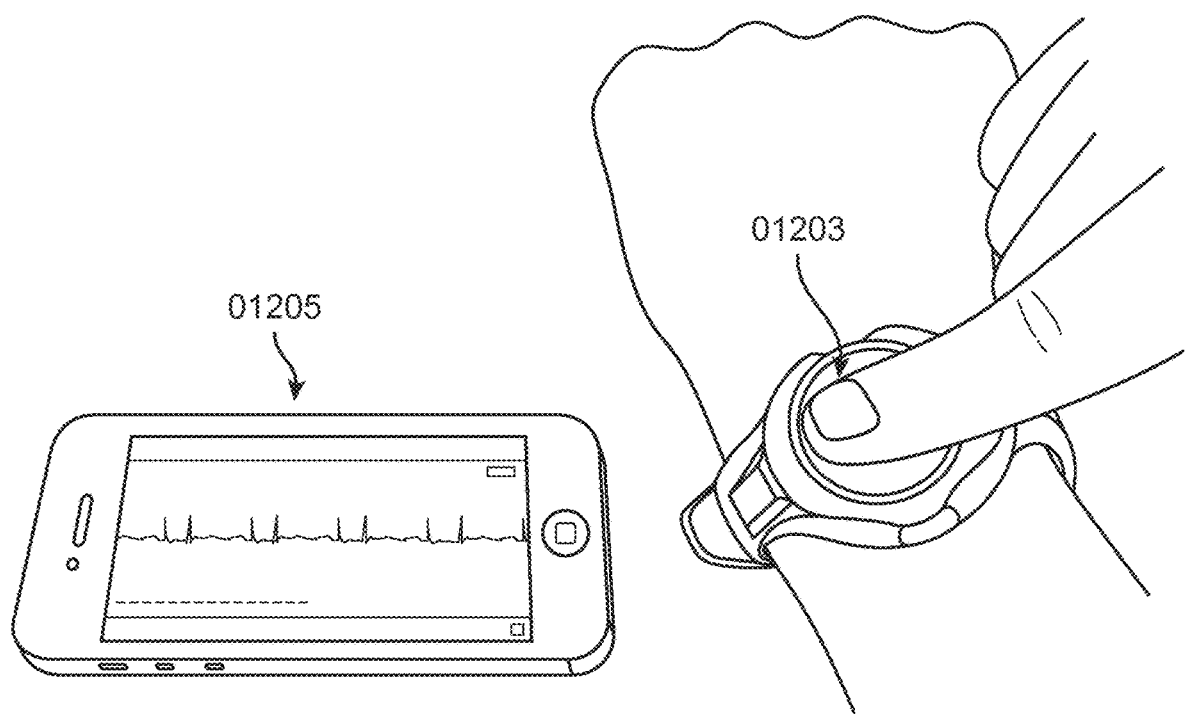
FIG. 30 shows the wristlet of FIG. 29 communicating (via ultrasound) with a mobile telecommunications device to transmit ECG information.

Another variation of an ECG measurement device configured to detect ECG signals and transmit ultrasound signals encoding ECG data is shown in FIGS. 29 and 30. In this example, a watch has been modified to include two electrodes. The first electrode (not visible in FIGS. 29 and 30) is located on the back of the watch ("wristlet"), and contacts the wrist of the person wearing the device. The second electrode 01203 is located on the "face" of the watch 01201, as shown in FIG. 29. The watch may therefor act as a single-lead ECG sensor, recording lead I (left arm/right arm). In some variations, the watch may also include an additional electrode 01207, for example on a side of the watch or strap region, that can be held against the subject's leg (right leg or left leg) to produce an additional/alternative lead(s) (e.g., lead II, lead III, etc.).

The watch may also include one or more controls and/or indicators. For example, the watch may also be configured as a timepiece (showing the time, etc.). The watch may include buttons, dials, etc. to select functions (e.g., turning on/off ECG reading, to begin to transmit ECG information, etc.).

FIG. 30 shows the variation of an ECG device 01203 shown in FIG. 29 transmitting to a mobile telecommunications device 01205. In this example, the mobile telecommunications device is a smartphone (iPhone™) that is configured to act as the receiving station for the ECG watch, and receive ultrasonic transmission of ECG information. Thus, the smartphone is running application software so that the processor of the smartphone causes the audio receiver (microphone) that is sensitive to ultrasound to 'listen' for ultrasound signals. The receiving device (smartphone) may then process the signal and display, in real-time as shown in FIG. 30, the ECG signals as they are being recorded. In this example, the smartphone is continuously receiving, displaying and recording the signal.

As mentioned, the signal may be processed before being displayed and/or stored and/or transmitted. For example, the signal may be filtered to remove artifacts and/or smooth. The signal may also be analyzed to automatically detect cardiac events (e.g., arrhythmias). Processing may be performed prior to ultrasound transmission by the watch, after transmission to a receiving device by the receiving device (e.g., smartphone) or divided between both.

In some variations, the watch may determine/confirm that a receiving device (e.g., smartphone) is ready to receive the information, as discussed above. In some variations, half- or full-duplex may be used. The watch may continuously broadcast the ECG data, or it may only transmit upon indication that the receiver is ready to receive; in such variations the device may store detected ECG data for later transmission.

In the example shown in FIGS. 29 and 30, the system also determines heart rate from the ECG information. Additional information may also be extracted from the signal. As mentioned above, the signal may be transmitted by the device (e.g., wristlet) as digital, analog or hybrid digital/analog ultrasound signals. Further, the signals may be encoded; in some variations, the device includes a key that can be scanned by the smartphone to provide decryption/pairing between the smartphone (receiver) and the device as discussed above.

Although many of the exemplary devices described herein are wearable devices (e.g., wristlets, chest bands, pendants, jewelry, etc.) the principles, modules, sub-systems, and elements described herein may be used for other devices, particularly biological sensor devices. For example, a case or holder for a mobile telecommunications device (e.g., smartphone) may incorporate any of these aspects, such as encoding of the ultrasonic signal, encoding as a hybrid digital/analog ultrasound signal, or the like. Thus in addition to wearable medical sensors, any stand-alone medical sensor may also include any of these features.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements, these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +1-2% of the stated value (or range of values), +/−5% of the stated value (or range of values), +/−10% of the stated value (or range of values), etc. Any numerical range recited herein is intended to include all sub-ranges subsumed therein.

While preferred embodiments of the present disclosure have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. An electrocardiogram (ECG) sensing system comprising:
  a sensor assembly comprising:
    a housing;
    a set of electrodes to measure an ECG of a subject, the set of electrodes including:
      a first electrode to contact a right upper extremity of the subject and a second electrode to contact a left upper extremity of the subject, the first electrode and the second electrode to form a lead I signal; and
      a third electrode to contact a left lower extremity of the subject to form a lead II signal with the first electrode, and to form a lead III signal with the second electrode; and
    a transmitter to:
      encode the lead I-III signals using an encryption key located on the housing; and
      modulate and transmit the lead I-III signals; and
  a mobile computing device removably coupled to the sensor assembly, wherein the sensor assembly is a separate device from the mobile computing device and the housing of the sensor assembly encloses the mobile computing device when it is coupled to the mobile computing device, the mobile computing device comprising:
    a processor;
    a wireless receiver operatively coupled to the processor;
    a display operatively coupled to the processor; and
    a memory operatively coupled to the processor, wherein the memory stores instructions that when executed by the processor cause the processor to:
      receive, with the wireless receiver, a first modulated signal carrying data of a first electric potential that is representative of the lead I signal;
      receive, with the wireless receiver, a second modulated signal carrying data of a second electric potential that is representative of the lead II signal, and wherein the first electric potential and the second electric potential are sensed concurrently;
      receive, with the wireless receiver, a third modulated signal carrying data of a third electric potential that is representative of the lead III signal;
      demodulate the first modulated signal and the second modulated signal;
      generate one or more of lead signals I, II, III, aVR, aVL, or aVF, wherein:
        aVR=(lead I+lead II)/2;
        aVL=lead I−(lead II)/2; and
        aVF=lead II−(lead I)/2; and
      display the one or more lead signals on the display.

2. The ECG sensing system according to claim 1, wherein the instructions when executed cause the processor further to generate each of lead signals I, II, III, aVR, aVL, and aVF.

3. The ECG sensing system according to claim 1, wherein the first modulated signal, the second modulated signal and the third modulated signal are frequency modulated acoustic signals having a carrier frequency in the range of from about 6 kHz to about 25 kHz.

4. The ECG sensing system according to claim 1, wherein the first modulated signal, the second modulated signal and the third modulated signal are digitally modulated in accordance with the Bluetooth® protocol.

5. The ECG sensing system according to claim 1, wherein the sensor assembly further comprises:
  a converter assembly situated in the housing, wherein the converter assembly comprises a microcontroller and the transmitter, and wherein:
  the first electrode is disposed on an exterior surface of the housing, wherein the first electrode is electrically coupled to the converter assembly;
  the second electrode is disposed on the exterior surface of the housing, wherein the second electrode is electrically coupled to the converter assembly;
  the third electrode is disposed on the exterior surface of the housing, wherein the third electrode is electrically coupled to the converter assembly;
  the microcontroller converts the first electric potential, the second electric potential and the third electric potential into, respectively, the first modulated signal carrying the first electric potential, the second modulated signal carrying the second electric potential, and the third modulated signal carrying the third electric potential; and the transmitter transmits the first modulated signal, the second modulated signal and the third modulated signal to the wireless receiver.

6. The ECG sensing system according to claim 5, wherein the housing comprises:
a case to enclose the mobile computing device, the case having a back exterior surface, at least two side exterior surfaces perpendicular to the back exterior surface, and a front region through which the display may be viewed, wherein:
the first electrode is on or adjacent to a first of the at least two side exterior surfaces;
the second electrode is on or adjacent to a second of the at least two exterior side surfaces; and
the third electrode on the back exterior surface.

7. The ECG system according to claim 5, wherein the housing comprises:
a wristlet, the wristlet having a back exterior surface adjacent to a user's wrist when the wristlet is worn, and a top exterior surface opposite to the back exterior surface, wherein:
the first electrode is on back exterior surface;
the second electrode is on the top exterior surface; and
the third electrode is on the top exterior surface electrically isolated from the second electrode.

8. The ECG sensing system according to claim 5, wherein the housing comprises:
a case having a back exterior surface and a top exterior surface, wherein the first electrode is on the top exterior surface, wherein the second electrode is on the top exterior surface, and wherein the third electrode is on the back exterior surface.

9. A method comprising:
receiving a first electric potential between a first electrode on a right upper extremity of a subject and a second electrode on a left upper extremity of the subject, wherein the first electrode and the second electrode are on an exterior surface of a housing of a mobile electrocardiogram (ECG) sensing unit;
receiving a second electric potential between the first electrode and a third electrode on a left lower extremity of the subject, wherein the third electrode is on the exterior surface of the housing of the mobile ECG unit, wherein the first electric potential and the second electric potential are sensed concurrently;
converting, by a microcontroller in the housing of the mobile ECG sensing unit, the first electric potential and the second electric potential into, respectively, a first modulated signal carrying the first electric potential and a second modulated signal carrying the second electric potential;
encoding the first modulated signal and the second modulated signal using an encryption key located on the housing; and
transmitting the first modulated signal and the second modulated signal wirelessly to a receiver of a mobile computing device, the mobile computing device removably coupled to the mobile ECG sensing unit, wherein the sensor assembly is a separate device from the mobile computing device and the housing of the mobile ECG sensing unit encloses the mobile computing device when it is coupled to the mobile computing device;
demodulating the first modulated signal and the second modulated signal with a processor of the mobile computing device;
generating, with the processor, one or more of lead signals I, II, III, aVR, aVL, and aVF, wherein:
lead I is based on the first electric potential;
lead II is based on the second electric potential
lead III=lead II−lead I
aVR=−(lead I+lead II)/2;
aVL=lead I−(lead II)/2; and
aVF=lead II−(lead I)/2; and
displaying the one or more of lead signals I, II, III, aVR, aVL, and aVF on a display screen of the mobile computing device.

10. The method according to claim 9 further comprising:
receiving a third electric potential that is representative of the lead III signal
converting the third electric potential into a third modulated signal carrying the third electric potential wherein lead III is based on the third electric potential.

11. The method according to claim 10, wherein generating the one or more lead signals comprises generating each of lead signals I, II, III, aVR, aVL, and aVF.

12. The method according to claim 10, wherein the first modulated signal, the second modulated signal and the third modulated signal are frequency modulated acoustic signals having a carrier frequency in the range of from about 6 kHz to about 25 kHz.

13. The method according to claim 10, wherein the first modulated signal, the second modulated signal and the third modulated signal are digitally modulated in accordance with a Bluetooth® protocol.

14. An electrocardiogram (ECG) sensing system comprising:
a sensor assembly comprising:
a housing;
a set of electrodes to measure an ECG of a subject, the set of electrodes including:
a first electrode to contact a right upper extremity of the subject and a second electrode to contact a left upper extremity of the subject, the first electrode and the second electrode to form a lead I signal; and
a third electrode to contact a left lower extremity of the subject to form a lead II signal with the first electrode, and to form a lead III signal with the second electrode; and
a transmitter to:
encode the lead I-III signals using an encryption key located on the housing; and
modulate and transmit the lead I-III signals; and
a mobile computing device removably coupled to the sensor assembly, wherein the sensor assembly is a separate device from the mobile computing device and the housing of the sensor assembly encloses the mobile computing device when it is coupled to the mobile computing device, the mobile computing device comprising:
a processor;
a wireless receiver operatively coupled to the processor;
a display screen operatively coupled to the processor; and
a memory operatively coupled to the processor, wherein the memory stores instructions that when executed by the processor cause the processor to:
receive, with the wireless receiver, a first modulated signal carrying data of a first electric potential between a first electrode on a right upper extremity of a subject and a second electrode on a left upper extremity of the subject, wherein the first electric potential is representative of a lead I signal;

receive, with the wireless receiver, a second modulated signal carrying data of a second electric potential that is representative of the lead II signal, and wherein the first electric potential and the second electric potential are sensed concurrently;

demodulate the first modulated signal and the second modulated signal;

generate one or more of lead signals I, II, III, aVR, aVL, or aVF, wherein:
lead III=lead II−lead I;
aVR=−(lead I+lead II)/2;
aVL=lead I−(lead II)/2; and
aVF=lead II−(lead I)/2; and display the one or more lead signals on the display screen.

15. The ECG sensing system according to claim 14 wherein the mobile computing device is further to:
receive, with the wireless receiver, a third modulated signal carrying data of a third electric potential that is representative of the lead III signal.

16. The ECG sensing system according to claim 15, wherein the instructions when executed cause the processor further to generate each of lead signals I, II, III, aVR, aVL, and aVF.

17. The ECG sensing system according to claim 15, wherein the first modulated signal, the second modulated signal and the third modulated signal are frequency modulated acoustic signals having a carrier frequency in the range of from about 6 kHz to about 25 kHz.

18. The ECG sensing system according to claim 15, wherein the first modulated signal, the second modulated signal and the third modulated signal are digitally modulated in accordance with the Bluetooth® protocol.

19. The ECG sensing system according to claim 15, wherein the sensor assembly further comprises:
a converter assembly situated in the housing, wherein the converter assembly comprises a microcontroller and a transmitter and wherein:
the first electrode is disposed on an exterior surface of the housing, wherein the first electrode is electrically coupled to the converter assembly;
the second electrode is disposed on the exterior surface of the housing, wherein the second electrode is electrically coupled to the converter assembly;
the third electrode is disposed on the exterior surface of the housing, wherein the third electrode is electrically coupled to the converter assembly;
the microcontroller converts the first electric potential, the second electric potential and the third electric potential into, respectively, the first modulated signal carrying the first electric potential, the second modulated signal carrying the second electric potential, and the third modulated signal carrying the third electric potential; and
the transmitter transmits the first modulated signal, the second modulated signal and the third modulated signal to the wireless receiver.

20. The ECG sensing system according to claim 19, wherein the housing comprises:
a case to enclose the mobile computing device, the case having a back exterior surface, at least two side exterior surfaces perpendicular to the back exterior surface, and a front region through which the display may be viewed, wherein:
the first electrode is on or adjacent to a first of the at least two side exterior surfaces;
the second electrode is on or adjacent to a second of the at least two exterior side surfaces; and
the third electrode on the back exterior surface.

21. The ECG sensing system according to claim 19, wherein the housing comprises:
a wristlet, the wristlet having a back exterior surface adjacent to a user's wrist when the wristlet is worn, and a top exterior surface opposite to the back exterior surface, wherein:
the first electrode is on back exterior surface;
the second electrode is on the top exterior surface; and
the third electrode is on the top exterior surface electrically isolated from the second electrode.

22. The ECG sensing system according to claim 19, wherein the housing comprises:
a case having a back exterior surface and a top exterior surface, wherein the first electrode is on the top exterior surface, wherein the second electrode is on the top exterior surface, and wherein the third electrode is on the back exterior surface.

23. The ECG sensing system of claim 1, wherein the sensor assembly has a band-type form factor.

24. The method of claim 9, wherein the mobile ECG sensing unit has a band-type form factor.

25. The ECG sensing system of claim 14, wherein the sensor assembly has a band-type form factor.

* * * * *